US012788887B2

(12) United States Patent
Dasbach et al.

(10) Patent No.: US 12,788,887 B2
(45) Date of Patent: Nov. 10, 2026

(54) DRUG DELIVERY DEVICE

(71) Applicant: SANOFI, Paris (FR)

(72) Inventors: Uwe Dasbach, Frankfurt am Main (DE); Katrin Rapp, Frankfurt am Main (DE); Hugo Revellat, Niort (FR); Thomas Mark Kemp, Cambridgeshire (GB); Robbie Wilson, Cambridgeshire (GB)

(73) Assignee: Sanofi, Paris (FR)

( * ) Notice: Subject to any disclaimer, the term of this patent is extended or adjusted under 35 U.S.C. 154(b) by 1208 days.

(21) Appl. No.: 17/046,381

(22) PCT Filed: Apr. 9, 2019

(86) PCT No.: PCT/EP2019/058867
§ 371 (c)(1),
(2) Date: Oct. 9, 2020

(87) PCT Pub. No.: WO2019/197361
PCT Pub. Date: Oct. 17, 2019

(65) Prior Publication Data

US 2021/0196892 A1 Jul. 1, 2021

(30) Foreign Application Priority Data

Apr. 11, 2018 (EP) .................................... 18305433

(51) Int. Cl.
*A61M 5/20* (2006.01)
*A61M 5/28* (2006.01)
(Continued)

(52) U.S. Cl.
CPC .......... *A61M 5/2033* (2013.01); *A61M 5/286* (2013.01); *A61M 5/3158* (2013.01);
(Continued)

(58) Field of Classification Search
CPC .. A61M 5/2033; A61M 5/286; A61M 5/3158; A61M 5/326; A61M 5/3157;
(Continued)

(56) References Cited

U.S. PATENT DOCUMENTS 5,957,895 A * 9/1999 Sage ................. A61M 5/14586 604/185
2012/0123387 A1* 5/2012 Gonzalez .......... A61M 37/0015 604/506
(Continued)

FOREIGN PATENT DOCUMENTS

CN 1913933 2/2007
CN 101827621 9/2010
(Continued)

OTHER PUBLICATIONS

PCT International Preliminary Report on Patentability in International Appln. No. PCT/EP2019/058867, dated Oct. 13, 2020, 10 pages.
(Continued)

*Primary Examiner* — James D Ponton
*Assistant Examiner* — John A Doubrava
(74) *Attorney, Agent, or Firm* — Fish & Richardson P.C.

(57) ABSTRACT

The present disclosure relates to a drug delivery device, comprising a housing adapted to receive a primary package, the housing comprising a distal surface adapted to be placed against an injection site and a proximal surface opposite the distal surface, the proximal surface adapted to be held in the palm of a user's hand during drug delivery, the housing having a flat form-factor in such a manner that a first extension of the housing between the distal surface and the proximal surface is less than at least one extension at right angles to the first extension.

21 Claims, 37 Drawing Sheets

(51) Int. Cl.
*A61M 5/315* (2006.01)
*A61M 5/32* (2006.01)

(52) U.S. Cl.
CPC ..... *A61M 5/326* (2013.01); *A61M 2005/2013* (2013.01); *A61M 2005/206* (2013.01); *A61M 2205/13* (2013.01)

(58) Field of Classification Search
CPC ................ A61M 5/50; A61M 5/14248; A61M 2005/2013; A61M 2005/206; A61M 2005/14252; A61M 2005/14256; A61M 2005/208; A61M 2005/247; A61M 2005/3267; A61M 2205/13
See application file for complete search history.

(56) References Cited

U.S. PATENT DOCUMENTS

| | | | | |
|---|---|---|---|---|
| 2013/0253472 | A1* | 9/2013 | Cabiri | A61M 5/14248 604/154 |
| 2014/0148784 | A1 | 5/2014 | Anderson et al. | |
| 2016/0129194 | A1 | 5/2016 | Brereton et al. | |
| 2016/0228644 | A1 | 8/2016 | Cabiri | |
| 2017/0182243 | A1 | 6/2017 | Cole et al. | |
| 2017/0354785 | A1* | 12/2017 | Gazeley | A61M 5/31536 |
| 2017/0368260 | A1* | 12/2017 | McCullough | A61M 5/20 |
| 2019/0160230 | A1* | 5/2019 | Yudelevich | A61M 5/3232 |

FOREIGN PATENT DOCUMENTS

| | | | |
|---|---|---|---|
| CN | 102497909 | | 6/2012 |
| CN | 102883759 | | 1/2013 |
| CN | 103068424 | | 4/2013 |
| CN | 103118737 | | 5/2013 |
| CN | 103476444 | | 12/2013 |
| CN | 103619378 | | 3/2014 |
| CN | 104984438 | | 10/2015 |
| CN | 105828854 | | 8/2016 |
| CN | 206183752 | | 5/2017 |
| CN | 112218670 | | 1/2021 |
| JP | 2013-500773 | | 1/2013 |
| JP | 2014-502884 | A | 2/2014 |
| JP | 2014-502886 | | 2/2014 |
| JP | 2014-515669 | | 7/2014 |
| JP | 2021-520904 | | 8/2021 |
| KR | 2016-0150645 | | 12/2016 |
| WO | WO 2005/061032 | | 7/2005 |
| WO | WO 2009/019437 | | 2/2009 |
| WO | WO 2011/014514 | | 2/2011 |
| WO | WO 2011/090955 | | 7/2011 |
| WO | WO 2011/133823 | | 10/2011 |
| WO | WO 2011/146166 | | 11/2011 |
| WO | WO 2012/000834 | | 1/2012 |
| WO | WO 2012/085027 | A1 | 6/2012 |
| WO | WO 2012/085030 | | 6/2012 |
| WO | WO 2012/110574 | | 8/2012 |
| WO | WO 2012/110580 | | 8/2012 |
| WO | WO 2012/145752 | | 10/2012 |
| WO | WO 2015/059192 | | 4/2015 |
| WO | WO 2015/087090 | | 6/2015 |
| WO | WO 2015/164649 | | 10/2015 |
| WO | WO 2016/193346 | A1 | 12/2016 |
| WO | WO 2017/062938 | A1 | 4/2017 |
| WO | WO 2017/214405 | | 12/2017 |
| WO | WO 2018/024625 | A1 | 2/2018 |
| WO | WO 2019/197360 | | 10/2019 |

OTHER PUBLICATIONS

PCT International Search Report and Written Opinion in International Appln. No. PCT/EP2019/058867, dated Jun. 13, 2019, 14 pages.

* cited by examiner

DRUG DELIVERY DEVICE

CROSS-REFERENCE TO RELATED APPLICATIONS

The present application is the national stage entry of International Patent Application No. PCT/EP2019/058867, filed on Apr. 9, 2019, and claims priority to Application No. EP 18305433.7, filed on Apr. 11, 2018, the disclosures of which are incorporated herein by reference.

TECHNICAL FIELD

The disclosure generally relates to a drug delivery device.

BACKGROUND

Drug delivery devices (i.e. devices capable of delivering medicaments from a medication container) typically fall into two categories—manual devices and auto-injectors.

In a manual device—the user must provide the mechanical energy to drive the fluid through the needle. This is typically done by some form of button/plunger that has to be continuously pressed by the user during the injection. There are numerous disadvantages to the user from this approach. If the user stops pressing the button/plunger then the injection will also stop. This means that the user can deliver an underdose if the device is not used properly (i.e. the plunger is not fully pressed to its end position). Injection forces may be too high for the user, in particular if the patient is elderly or has dexterity problems.

Auto-injectors are devices which completely or partially replace activities involved in parenteral drug delivery from standard syringes. These activities may include removal of a protective syringe cap, insertion of a needle into a patient's skin, injection of the medicament, removal of the needle, shielding of the needle and preventing reuse of the device. This overcomes many of the disadvantages of manual devices. Injection forces/button extension, hand-shaking and the likelihood of delivering an incomplete dose are reduced. Triggering may be performed by numerous means, for example a trigger button or the action of the needle reaching its injection depth. In some devices the energy to deliver the fluid is provided by a spring.

SUMMARY

An object of the present disclosure is to provide an improved drug delivery device.

The object is achieved by a drug delivery device according to claim 1.

Exemplary embodiments are provided in the dependent claims.

According to the present disclosure a drug delivery device comprises a housing adapted to receive a primary package, the housing comprising a distal surface adapted to be placed against an injection site and a proximal surface opposite the distal surface, the proximal surface adapted to be held in the palm of a user's hand during drug delivery, the housing having a flat form-factor in such a manner that a first extension of the housing between the distal surface and the proximal surface is less than at least one extension at right angles to the first extension. In an exemplary embodiment, the first extension of the housing between the distal surface and the proximal surface is less than any other extension at right angles to the first extension.

In an exemplary embodiment, the distal surface of the housing has a flat outer surface. Alternatively, the distal surface of the housing is bent in an inward direction of the housing or has a concave shape.

In an exemplary embodiment, the proximal surface of the housing is bent in an outward direction of the housing or has a convex shape.

In an exemplary embodiment, the drug delivery device comprises an injection needle configured to be connected or connectable to a primary package received within the housing. In particular, the needle comprises a first tip which is automatically movable relative with respect to the housing between a retracted position hidden within the housing and an extended position extending through the distal surface of the housing.

In an exemplary embodiment, the needle extends from the distal surface perpendicularly.

In an exemplary embodiment, a mounting axis of the primary package is essentially at right angles with respect to the first extension.

In an exemplary embodiment, the distal surface is non-adhesive.

In an exemplary embodiment, the distal surface is rigid.

In an exemplary embodiment, the needle is part of a needle module and has a first tip adapted to extend through the distal surface and a second tip adapted to pierce a septum on a primary package received within the housing.

In an exemplary embodiment, the needle is a single needle bent at approximately 90 degrees. In further exemplary embodiments, the first tip and the second tip of the needle are separate from each other and arranged at approximately 90 degrees to each other and for example connected within a solid block or via a flexible tube.

In an exemplary embodiment, the drug delivery device comprises a trigger adapted to cause the needle to be relatively moved with respect to the housing from the retracted position to the extended position upon operation of the trigger. In an exemplary embodiment, the trigger may comprise at least one of a shroud, at least one button and a body contact sensor. The shroud is for example configured as a needle shroud which is for example movable between an extended position covering the needle, in particular its first tip and a retracted position uncovering the needle, in particular its first tip. In a further embodiment, the body contact sensor and the needle shroud form a single trigger assembly.

In an exemplary embodiment, the at least one button is disposed at the proximal surface or at at least one lateral surface of the housing.

In an exemplary embodiment, the drug delivery device comprises a carrier adapted to mount a primary package. Furthermore, the primary package may be movable substantially in parallel with the distal surface of the housing between a rearward position, in which the second tip is spaced from the septum and a forward position, in which the second tip pierces the septum. For example, the primary package is relatively movable with respect to at least one of the carrier, the trigger and the housing to pierce the septum by the needle. Alternatively, the carrier with the mounted primary package may be relatively movable with respect to at least one of the trigger and the housing to pierce the septum by the needle.

In an exemplary embodiment, the button is adapted to be locked prior to operation of the shroud or body contact sensor preventing operation of the button. Furthermore, the button is adapted to be unlocked for example upon operation of the shroud or body contact sensor allowing operation of the button.

In an exemplary embodiment, the drug delivery device comprises a drive spring adapted to apply a force in a forward direction to a piston of the primary package. In particular, the drug delivery device may further comprise a plunger adapted to propagate the force from the drive spring to the piston.

In an exemplary embodiment, the drug delivery device comprises a primary package containing a medicament. For example, the primary package is formed as a pre-cartridge or a container containing a medicament.

In an exemplary embodiment, a needle return spring is arranged to bias the first tip towards the retracted position.

In an exemplary embodiment, a shroud spring is arranged to bias the shroud in the distal direction against the housing or against the needle module.

In an exemplary embodiment, a needle spring is arranged to bias the needle module in the distal direction against the housing.

In an exemplary embodiment, a carrier spring is arranged to bias the carrier towards the needle module.

In an exemplary embodiment, the needle spring is charged by depression of the shroud into the retracted position.

According to an aspect of the present disclosure, a method of using the drug delivery device described above comprises taking the housing with a hand such that the proximal surface is located within a palm of the hand, placing the distal surface on an injection site, operating the trigger to move the needle to the extended position, holding the drug delivery device on the injection site during an injection time.

According to the present disclosure, a drug delivery device, in particular an auto-injector with a flat form-factor or low profile is provided, in particular adapted to facilitate an injection essentially perpendicular to a mounting axis of a primary pack, e.g. a drug cartridge. Flat form-factor or low profile means that a height of the drug delivery device is substantially less than its width. The flat form-factor of the device provides superior handling and usability as opposed to a conventional pen-shaped auto-injector.

The drug delivery device may be used as a single-use disposable, shroud activated auto-injector, operated by patients for self-administration or by health care professionals to others. The flat-format facilitates optimised ergonomics for longer duration of injections, reduced effort and pain for those with impairments, and reduced susceptibility to unintentional movements during an injection.

The drug delivery device may be adapted to retain the primary pack sealed until pierced at the moment of injection or immediately prior to this.

As opposed to a conventional pen injector, the presently described flat form-factor drug delivery device helps prevent leaking of the medicament, yields a higher stability during longer injection times (e.g. more than 15 s) because it is easier for the user to hold a flat form-factor drug delivery device against the injection site without flinching or altering the orientation than with a conventional pen injector. Long injection times allow for using the drug delivery device with high viscosity drugs which cannot be injected within a short time.

Moreover, the flat format allows for improved discretion during injection allowing users to inject themselves in public. Furthermore, the flat-format has a considerably increased skin contact surface as opposed to conventional pen injectors which results in a reduced contact pressure per unit area.

In an exemplary embodiment, the distal surface may be rigid so as to maintain its shape when placed against an injection site. In another an exemplary embodiment, the distal surface may be flexible.

In an exemplary embodiment, the distal surface is not adhesive, i.e. it does not have an adhesive applied to it. The presently claimed drug delivery device is thus a handheld device whereas conventional patch devices are intended to be adhesively connected to the injection site and not handheld during injection.

In an exemplary embodiment, the distal surface may have anti-skid properties, e.g. due to a surface structure or a coating.

The drug delivery device, as described herein, may be configured to inject a drug or medicament into a patient. For example, delivery could be sub-cutaneous, intra-muscular, or intravenous. Such a device could be operated by a patient or care-giver, such as a nurse or physician, and can include various types of safety syringe, pen-injector, or auto-injector.

The device can include a cartridge-based system that requires piercing a sealed ampule before use. Volumes of medicament delivered with these various devices can range from about 0.5 ml to about 2 ml or 3 ml. Yet another device can include a large volume device ("LVD") or patch pump, configured to adhere to a patient's skin for a period of time (e.g., about 5, 15, 30, 60, or 120 minutes) to deliver a "large" volume of medicament (typically about 2 ml to about 5 ml). In combination with a specific medicament, the presently described devices may also be customized in order to operate within required specifications. For example, the device may be customized to inject a medicament within a certain time period (e.g., about 3 to about 20 seconds for auto-injectors, and about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 3 cP to about 50 cP. Consequently, a drug delivery device will often include a hollow needle ranging from about 25 to about 31 Gauge in size. Common sizes are 27 and 29 Gauge.

The delivery devices described herein can also include one or more automated functions. For example, one or more of needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device.

The one or more automated functions of an auto-injector may be activated via an activation mechanism. Such an activation mechanism can include one or more of a button, a lever, a needle shroud, or other activation component. Activation may be a one-step or multi-step process. That is, a user may need to activate one or more activation mechanism in order to cause the automated function. For example, a user may depress a needle shroud against their body in order to cause injection of a medicament. In other devices, a user may be required to depress a button and retract a needle shield in order to cause injection.

In addition, such activation may activate one or more mechanisms. For example, an activation sequence may activate at least two of needle insertion, medicament injection, and needle retraction. Some devices may also require a specific sequence of steps to cause the one or more automated functions to occur. Other devices may operate with sequence independent steps.

Some delivery devices can include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

Further scope of applicability of the present disclosure will become apparent from the detailed description given hereinafter. However, it should be understood that the detailed description and specific examples, while indicating exemplary embodiments of the disclosure, are given by way of illustration only, since various changes and modifications within the spirit and scope of the disclosure will become apparent to those skilled in the art from this detailed description.

BRIEF DESCRIPTION OF THE FIGURES

Corresponding parts are marked with the same reference symbols in all figures.

DETAILED DESCRIPTION

Figure 1A:
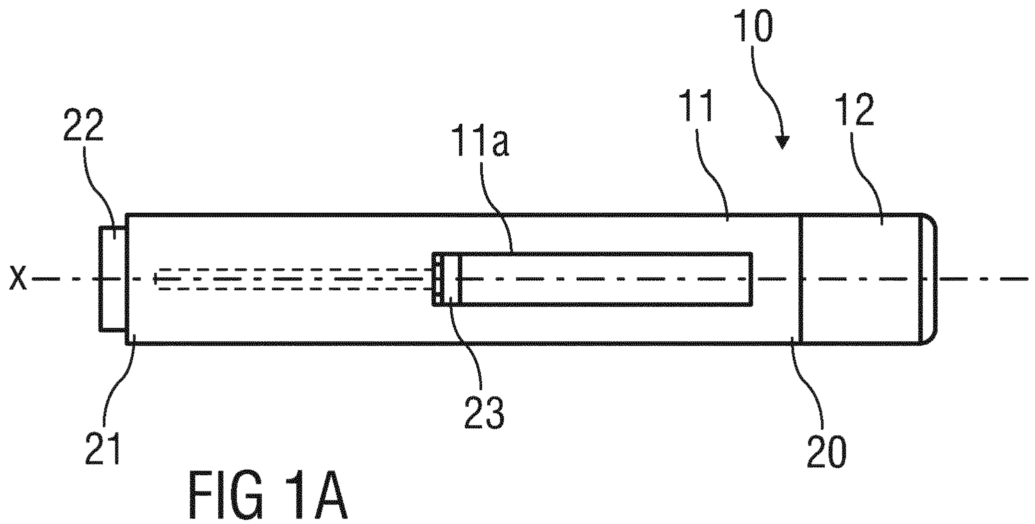
FIG. 1 is a schematic view of an exemplary embodiment of a drug delivery device.
Figure 1B:
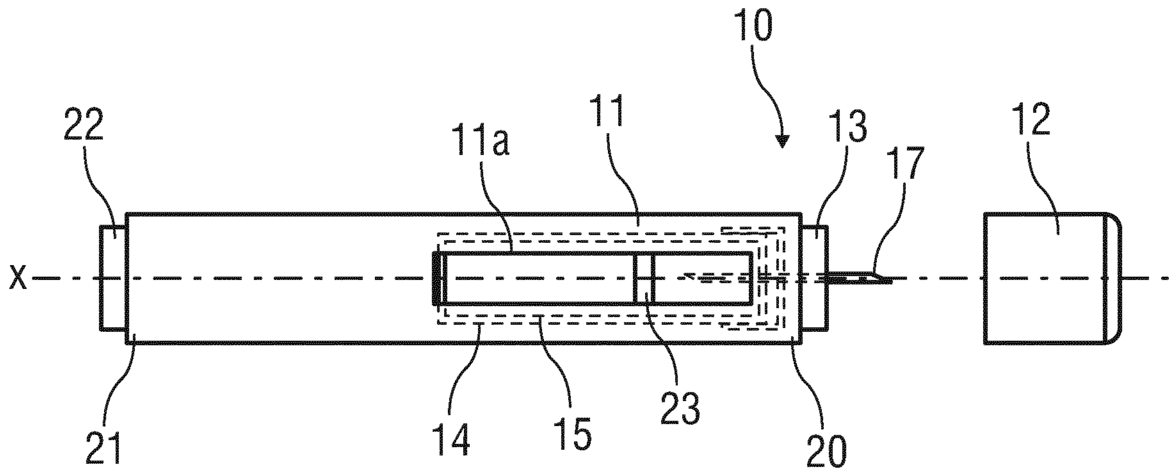

According to some embodiments of the present disclosure, an exemplary drug delivery device 10 is shown in FIGS. 1A and 1B.

Device 10, as described above, is configured to inject a drug or medicament into a patient's body.

Device 10 includes a housing 11 which typically contains a reservoir containing the medicament to be injected (e.g., a primary package 24 or a container or syringe) and the components required to facilitate one or more steps of the delivery process.

Device 10 can also include a cap assembly 12 that can be detachably mounted to the housing 11, in particular on a distal or front end D of the device 10. Typically, a user must remove cap assembly or cap 12 from housing 11 before device 10 can be operated.

As shown, housing 11 is substantially cylindrical and has a substantially constant diameter along the longitudinal axis X. The housing 11 has a distal region 20 and a proximal region 21.

The term "distal" refers to a location that is relatively closer to a site of injection, and the term "proximal" refers to a location that is relatively further away from the injection site.

Device 10 can also include a needle shroud 13 coupled to the housing 11 to permit movement of the shroud 13 relative to the housing 11. For example, the shroud 13 can move in a longitudinal direction parallel to longitudinal axis X. Specifically, movement of the shroud 13 in a proximal direction can permit a needle 17 to extend from distal region 20 of housing 11. Insertion of the needle 17 can occur via several mechanisms. For example, the needle 17 may be fixedly located relative to housing 11 and initially be located within an extended needle shroud 13. Proximal movement of the shroud 13 by placing a distal end of shroud 13 against a patient's body and moving housing 11 in a distal direction will uncover the distal end of needle 17. Such relative movement allows the distal end of needle 17 to extend into the patient's body. Such insertion is termed "manual" insertion as the needle 17 is manually inserted via the patient's manual movement of the housing 11 relative to the shroud 13.

Another form of insertion is "automated," whereby the needle 17 moves relative to housing 11. Such insertion can be triggered by movement of shroud 13 or by another form of activation, such as, for example, a button 22. As shown in FIGS. 1A & 1B, button 22 is located at a proximal or back end P of the housing 11. However, in other embodiments, button 22 could be located on a side of housing 11. In further embodiments, the button 22 has been deleted and is replaced for instance by a shroud trigger mechanism, e.g. provided by pushing the needle shroud 13 inside the housing when the drug delivery device is put onto an injection side.

Other manual or automated features can include drug injection or needle retraction, or both. Injection is the process by which a bung or piston 23 is moved from a proximal location within a container or syringe 24 to a more distal location within the syringe 24 in order to force a medicament from the syringe 24 through needle 17.

In some embodiments, an energy source, e.g. a drive spring 30 is arranged in a plunger 40 and is under compression before device 10 is activated. A proximal end of the drive spring 30 can be fixed within proximal region 21 of housing 11, and a distal end of the drive spring 30 can be configured to apply a compressive force to a proximal surface of piston 23. Following activation, at least part of the energy stored in the drive spring 30 can be applied to the proximal surface of piston 23. This compressive force can act on piston 23 to move it in a distal direction. Such distal movement acts to compress the liquid medicament within the syringe 24, forcing it out of needle 17.

Following injection, the needle 17 can be retracted within shroud 13 or housing 11. Retraction can occur when shroud 13 moves distally as a user removes device 10 from a patient's body. This can occur as needle 17 remains fixedly located relative to housing 11. Once a distal end of the shroud 13 has moved past a distal end of the needle 17, and the needle 17 is covered, the shroud 13 can be locked. Such locking can include locking any proximal movement of the shroud 13 relative to the housing 11.

Another form of needle retraction can occur if the needle 17 is moved relative to the housing 11. Such movement can occur if the syringe within the housing 11 is moved in a proximal direction relative to the housing 11. This proximal movement can be achieved by using a retraction spring (not shown), located in the distal region 20. A compressed retraction spring, when activated, can supply sufficient force to the syringe 24 to move it in a proximal direction. Following sufficient retraction, any relative movement between the needle 17 and the housing 11 can be locked with a locking mechanism. In addition, button 22 or other components of device 10 can be locked as required.

In some embodiments, the housing may comprise a window 11*a* through which the syringe 24 can be monitored.

Figure 2A:
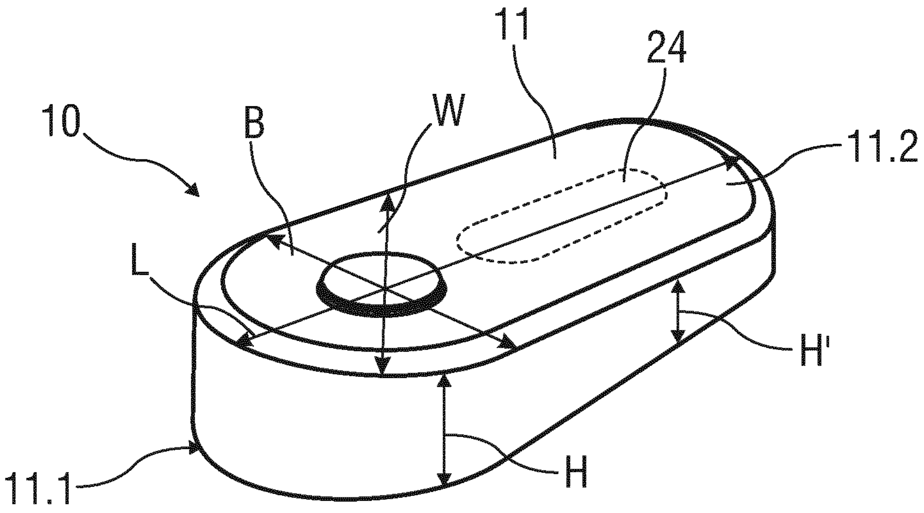
FIG. 2A is a perspective view of an exemplary embodiment of a drug delivery device.

FIG. 2A is a schematic perspective view of an exemplary embodiment of a drug delivery device 10 comprising a housing 11 adapted to contain a primary package 24, e.g. a cartridge or a container containing a medicament. As shown, housing 11 is substantially flat, i.e. it has a distal surface 11.1.

The distal surface 11.1 is adapted to be placed against an injection site. The housing 11 further comprises a proximal surface 11.2 opposite the distal surface 11.1. The proximal surface 11.2 is configured as a gripping surface, e.g. to be held in the palm of a user's hand during drug delivery.

In an exemplary embodiment, the distal surface 11.1 has a flat outer surface. Alternatively, the distal surface 11.1 may be bent in an inward direction of the housing 11 or has a concave shape.

In an exemplary embodiment, the proximal surface 11.2 is bent in an outward direction of the housing 11 or has a convex shape.

The housing 11 has a flat form-factor in such a manner that at least a first extension H of the housing 11 between the distal surface 11.1 and the proximal surface 11.2 is less than at least one extension L at right angles to the first extension H.

In an exemplary embodiment, the first extension H or any other varied first extensions H' of the housing 11 between the distal surface 11.1 and the proximal surface 11.2 is less than any other extension L, B, W at right angles to the first extensions H, H'. In other words: The first extension H represents the height of the device 10. The height of the device 10, in particular the height of the housing 11, may vary. The at least one first extension H and/or H' is or are less than each of the other extensions L, B, W of the device 10, wherein the other extensions L, B, W for instance represent the length, the width and/or a diagonal of the device 10.

In an exemplary embodiment, a mounting axis of the primary package 24 is essentially at right angles with respect to the first extension H or H'.

The distal surface 11.1 may be configured non-adhesive. It allows better user comfort. Furthermore, the distal surface 11.1 is rigid.

Figure 2B:
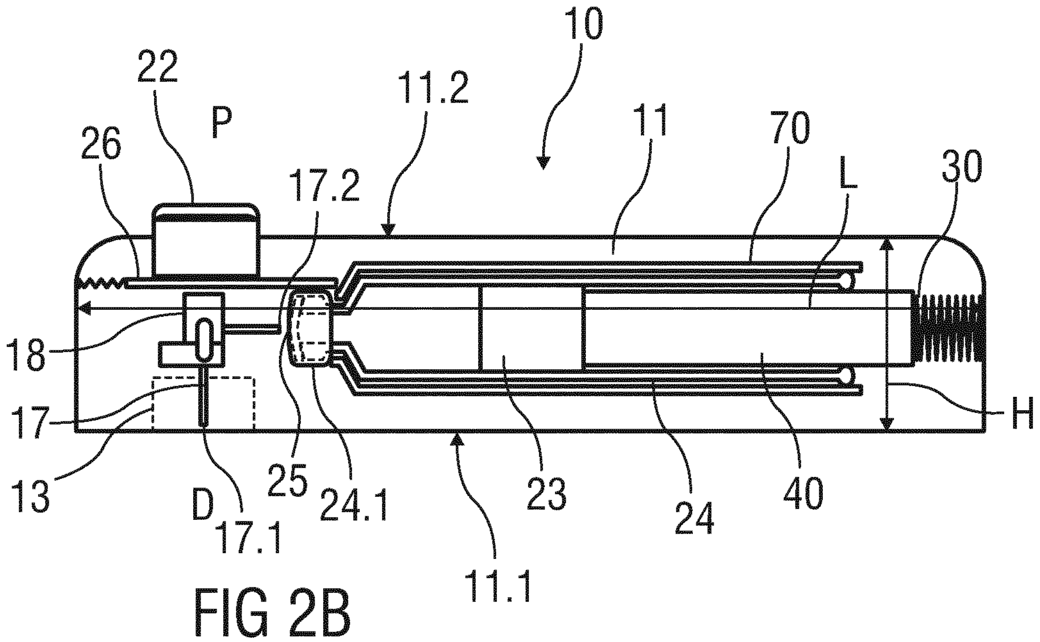
FIGS. 2B to 2D are schematic views of an exemplary embodiment of a drug delivery device in different states.
Figure 2C:
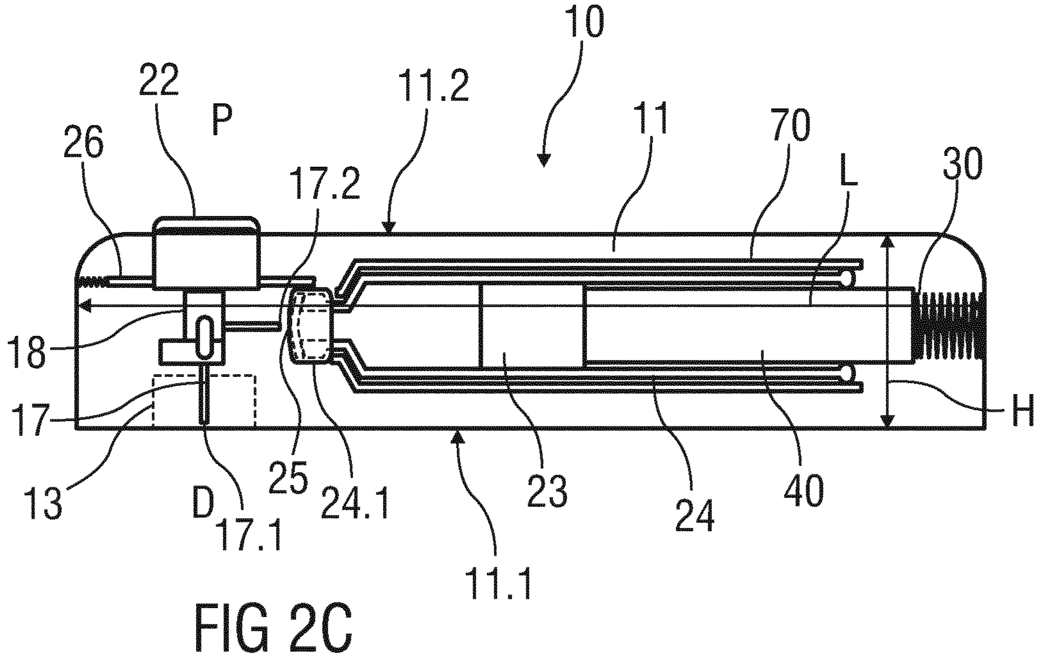
Figure 2D:
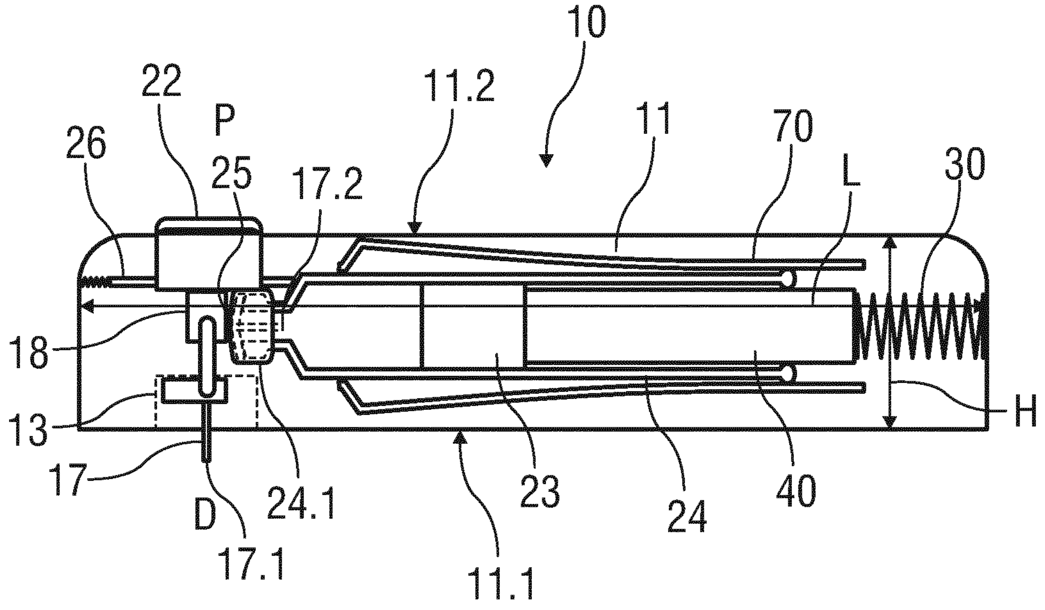

FIGS. 2B to 2D are schematic perspective views of an exemplary embodiment of a drug delivery device 10. A housing 11 of the drug delivery device 10 has a similar flat-form-factor as of the housing 11 in FIG. 2A.

The drug delivery device 10 comprises an injection needle 17. The needle 17 extends with respect to the distal surface 11.1 perpendicularly.

Further, the needle 17 is configured to be connected or connectable to the primary package 24 received and hold within the housing 11. In particular, the needle 17 comprises a first tip 17.1 automatically relatively movable with respect to the housing 11 between a retracted position hidden within the housing 11 (shown in FIG. 2B, 2C) and an extended position extending through the distal surface 11.1 of the housing 11 (shown in FIG. 2D).

In particular, in the extended position, the needle 17 extends from the distal surface 11.1 perpendicularly.

The drug delivery device 10 may be configured as a button-triggered or shroud-triggered device or a sequentially triggered device with a sequence of button-shroud-triggering or shroud-button-triggering.

As a button-triggered device, a button 22 is coupled with a trigger 26 to trigger the drug delivery device 10 (as it is shown in embodiments of FIGS. 2A to 10, 40 to 54).

The drug delivery device 10 may optionally comprise a shroud 13. In an exemplary embodiment, e.g. for a button-triggered device, the shroud 13 is adapted to cover a needle 17 after injection.

In another exemplary embodiment, e.g. of a shroud-triggered device, a shroud 13 may be adapted to cover the needle 17 before and after injection.

As a shroud-triggered device, the trigger 26 may be coupled with the shroud 13 to trigger the drug delivery device 10 (as it is shown for example in embodiments of FIGS. 11 to 39, 55 to 68).

The drug delivery device 10 comprises the housing 11 adapted to contain a primary package 24, e.g. a cartridge or a container.

The distal surface 11.1 extends in parallel with a longest axis of the drug delivery device 10. Further, the distal surface 11.1 extends substantially in parallel with a longitudinal axis of the primary package 24. The distal surface 11.1 is intended to be directed towards an injection site during injection and adapted to rest on the injection site. The housing 11 may be configured to resemble a computer mouse.

The term "distal" refers to a location that is relatively closer to a site of injection, and the term "proximal" refers to a location that is relatively further away from the injection site.

Device 10 can also include a needle shroud 13 coupled to the housing 11 to permit movement of the shroud 13 relative to the housing 11. For example, the shroud 13 can move in a proximal direction P or in a distal direction D. Specifically, movement of the shroud 13 in a proximal direction can permit a needle 17 to extend from the distal surface 11.1 of housing 11.

The term "forward" refers to a location that is relatively close to the needle 17 along the longest axis of the drug delivery device 10, and the terms "rear" or "rearward" refer to a location that is relatively further away from the needle 17 along the longest axis of the drug delivery device 10.

Insertion of the needle 17 can occur via several mechanisms. For example, the needle 17 may be fixedly located relative to housing 11 and initially be located within an extended needle shroud 13. Proximal movement of the shroud 13 by placing a distal end of shroud 13 against a patient's body and moving housing 11 in a distal direction will uncover the distal end of needle 17. Such relative movement allows the distal end of needle 17 to extend into the patient's body. Such insertion is termed "manual" insertion as the needle 17 is manually inserted via the patient's manual movement of the housing 11 relative to the shroud 13.

Another form of insertion is "automated," whereby the needle 17 moves relative to housing 11. Such insertion can be triggered by movement of shroud 13 or by another form of activation, such as, for example, a button 22. As shown in FIG. 2A to 2D, button 22 is located at a proximal surface 11.2 of the housing 11. However, in other embodiments, button 22 could be located on a side of housing 11. In further embodiments, the button 22 has been deleted and is replaced for instance by a shroud trigger mechanism, e.g. provided by pushing the needle shroud 13 inside the housing when the drug delivery device is put onto an injection side.

Other manual or automated features can include drug injection or needle retraction, or both. Injection is the process by which a bung or piston 23 is moved from a rearward location within a primary package 24, container or syringe to a more forward location within the primary package 24 in order to force a medicament from the primary package 24 through needle 17.

In some embodiments, an energy source, e.g. a drive spring may be arranged and under compression before device 10 is activated. One end of the drive spring can be fixed within the housing 11, and another end of the drive spring can be configured to apply a compressive force to a surface of piston 23. Following activation, at least part of the energy stored in the drive spring can be applied to the piston 23. This compressive force can act on piston 23 to move it to displace the liquid medicament from the primary package 24.

Following injection, the needle 17 can be retracted within shroud 13 or housing 11. Retraction can occur when shroud 13 moves distally as a user removes device 10 from a patient's body. This can occur as needle 17 remains fixedly located relative to housing 11. Once a distal end of the shroud 13 has moved past a distal end of the needle 17, and the needle 17 is covered, the shroud 13 can be locked. Such locking can include locking any proximal movement of the shroud 13 relative to the housing 11.

Another form of needle retraction can occur if the needle 17 is moved relative to the housing 11. Following sufficient retraction, any relative movement between the needle 17 and the housing 11 can be locked with a locking mechanism. In addition, button 22 or other components of device 10 can be locked as required.

The needle 17 is part of a needle module 18 and has a first tip 17.1 adapted to extend from the distal surface 11.1 and a second tip 17.2 extending essentially in parallel with the distal surface 11.1 within the housing 10 towards the primary package 24 and adapted to pierce a septum 25 arranged on a forward end 24.1 of the primary package 24 to establish a fluid communication between the needle 17 and a cavity within the primary package 24 filled with the medicament. The primary package 24 may be adapted to be moved substantially in parallel with the distal surface 11.1 towards the needle module 18 to allow the second tip 17.2 to pierce the septum 25.

In an exemplary embodiment, the needle 17 may comprise a single needle 17 bent at approximately 90 degrees. In another exemplary embodiment, the needle module 18 may comprise a solid block 19 and the needle 17 may comprise two separate needle tips 17.1, 17.2 arranged at 90 degrees to each other and connected within the solid block 19. In yet another exemplary embodiment, the two separate needle tips 17.1, 17.2 are arranged at 90 degrees to each other and connected via a flexible connector, e.g. a tubing.

The shroud 13 may be configured as a trigger to initiate movement of the primary package 24 towards the needle module 18 and movement of the needle 17 in the distal direction D to extend from the distal surface 11.1.

In an exemplary embodiment, a button 22 is provided, e.g. on the proximal surface 11.2 to initiate movement of the primary package 24 towards the needle module 18 and movement of the needle 17 in the distal direction D to extend from the distal surface 11.1. In this case, the shroud 13 may be used as a safety interlock, allowing operation of the button 22 only when the shroud 13 is depressed into the housing 11 in the proximal direction P. In another embodiment, operation of the trigger button 22 may be possible regardless of the position of the shroud 13 but the drug delivery device 10 may be configured to ignore operation of the trigger button 22 unless the shroud 13 is depressed into the housing first. In yet another embodiment, initiation of movement of the primary package 24 towards the needle module 18 and movement of the needle 17 in the distal direction D to extend from the distal surface 11.1 may require depression of the shroud 13 and operation of the button 22 regardless of the order of these actions.

In yet another embodiment, a button 22 may not be provided and movement of the primary package 24 towards the needle module 18 and movement of the needle 17 in the distal direction D to extend from the distal surface 11.1 may be initiated only be depression of the shroud 13.

A plunger 40 is arranged to apply a force on the piston 23, e.g. driven by a drive spring.

Figure 3:
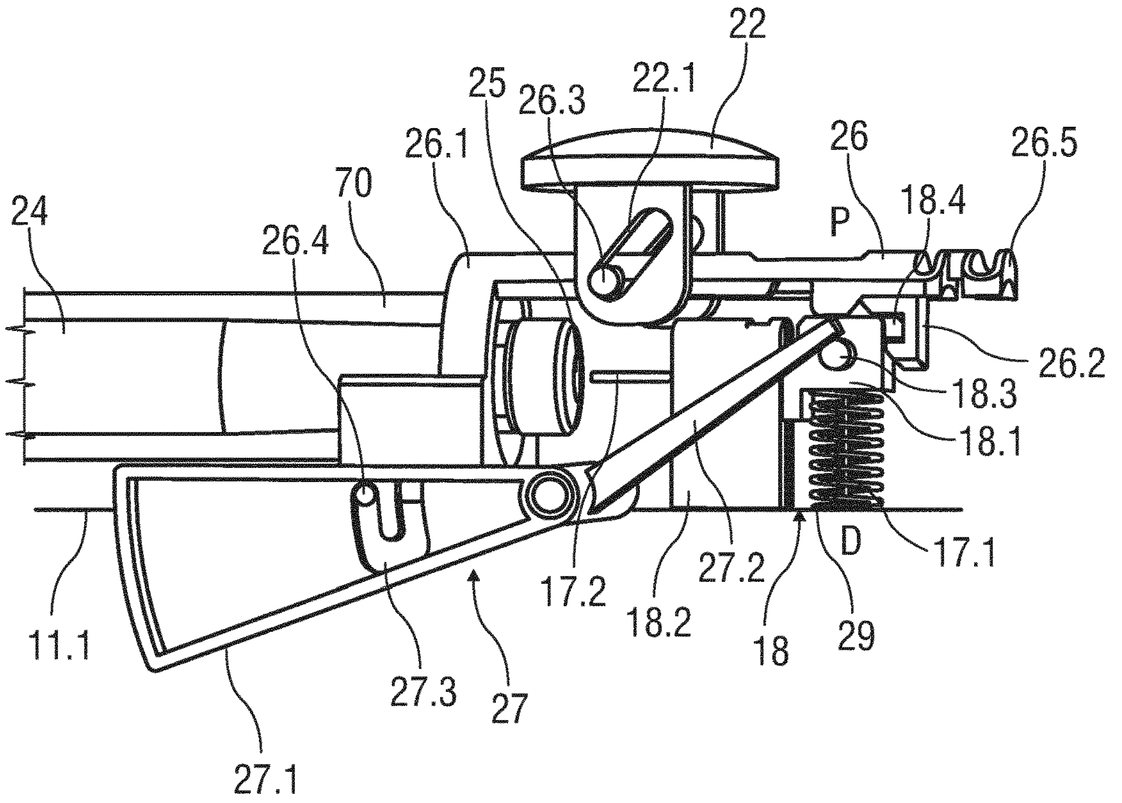
FIG. 3 is a schematic detail view of an exemplary embodiment of a drug delivery device.
Figure 4:
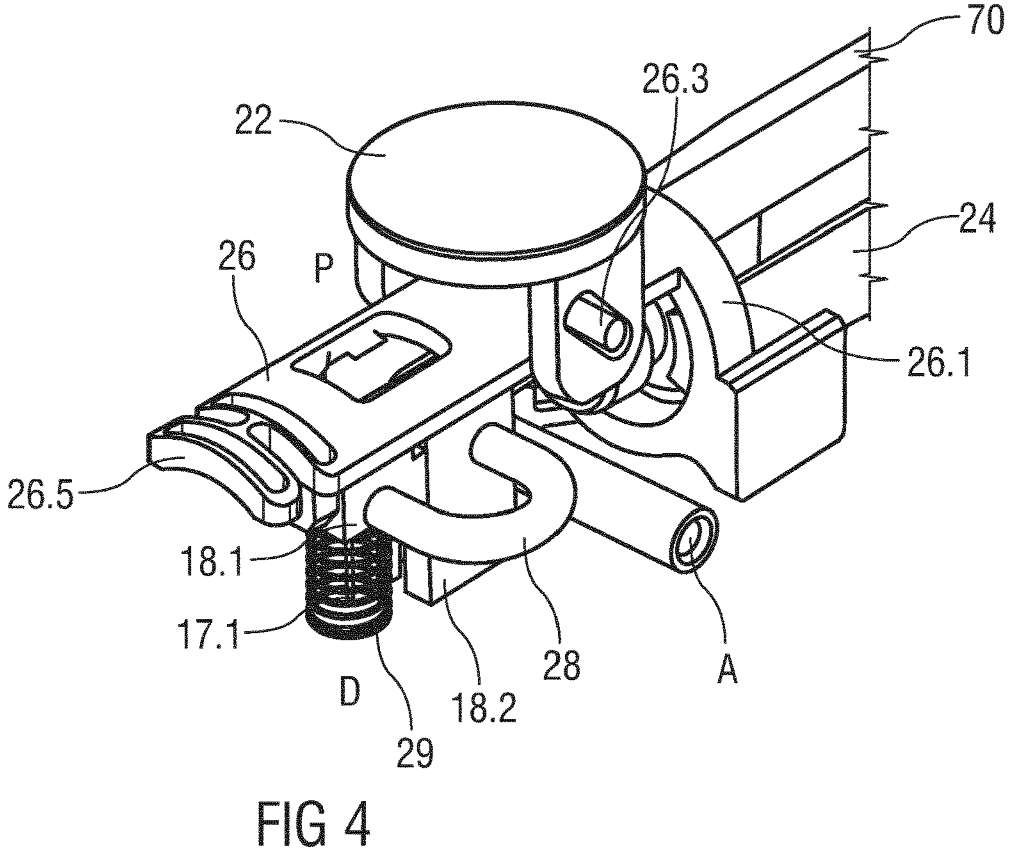
FIG. 4 is a schematic detail view of an exemplary embodiment of a drug delivery device.

FIGS. 3 and 4 are schematic detail views of an exemplary embodiment of a drug delivery device 10.

The primary package 24 is guided within a collar 26.1 of a trigger chassis 26 which is slidable in the forward direction between a locking position and a release position. A body contact sensor 27 is pivoted about an axis A in the housing 11, e.g. a transversal axis, such that a contact part 27.1 of the body contact sensor 27 may extend from the distal surface 11.1 and pivot about the axis A to be depressed into the housing 11 behind or flush with the distal surface 11.1. A needle module 18 having a needle 17 with a first tip 17.1 and a second tip 17.2 is provided, the first tip 17.1 adapted to be extended from the distal surface 11.1 and the second tip adapted to point towards the primary package 24 to pierce a septum 25 thereof. The needle module 18 comprises a first sub-module 18.1 holding the first tip 17.1 and a second sub-module 18.2 holding the second tip 17.2. The second sub-module 18.2 is fixed in position within the housing 11 whereas the first sub-module 18.1 is movable from a retracted position in the distal direction D into an extended position and vice versa in the proximal direction P. A fluid communication between the first tip 17.1 and the second tip 17.2 is established by a flexible tube 28, e.g. a silicone tube. A needle return spring 29 is arranged to bias the first sub-module 18.1 with the first tip 17.1 of the needle 17 in the proximal direction P, i.e. into the housing 11.

The first sub-module 18.1 comprises at least one pin-shaped protrusion 18.3 adapted to be engaged by a resilient arm 27.2 of the body contact sensor 27 such that, when the contact part 27.1 of the body contact sensor 27 is depressed in the proximal direction P, the arm 27.2 is resiliently deformed to bias the first sub-module 18.1 in the distal direction D.

A hook 26.2 on the trigger chassis 26 is adapted to engage a rib 18.4 on the first sub-module 18.1 preventing movement of the first sub-module 18.1 out of the retracted position when the trigger chassis 26 is in the locking position. A button 22 is coupled to the trigger chassis 26 in such a manner that depression of the button 22 in the distal direction D moves the trigger chassis 26 from the locking position to the release position. For this purpose, the button 22 may comprise at least one angled cam surface 22.1 engaging a respective button pin 26.3 on the trigger chassis 26. The trigger chassis 26 may further comprise an interlock pin 26.4 engaging a U-shaped slot 27.3 in the body contact sensor 27 in such a manner that movement of the trigger chassis 26 from the locking position to the release position is only possible upon prior depression of the contact part 27.1 in the proximal direction P into the housing 11.

A spring element 26.5 may be provided to bias the trigger chassis 26 rearward toward the locking position. The spring element 26.5 may be integrally shaped with the trigger chassis 26 or be arranged as a separate spring. The spring element 26.5 may be adapted to bear against the housing 11.

A carrier 70 may arranged within the housing 11 to contain the primary package 24 and to allow movement thereof essentially in parallel with the distal surface 11.1 towards the needle module 18.

Figure 5:
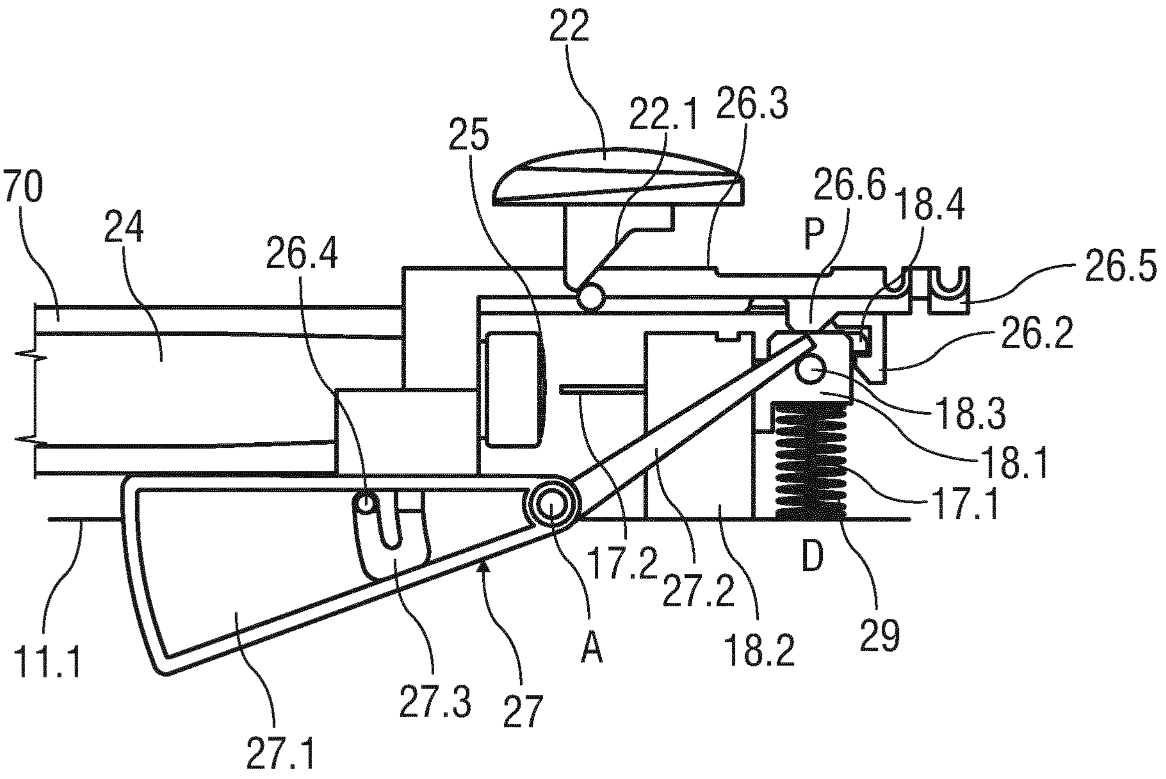
FIG. 5 is a schematic view of the drug delivery device prior to use.

FIG. 5 is a schematic view of the drug delivery device 10 prior to use. The primary package 24 is spaced from the second tip 17.2. The first sub-module 18.1 is in the retracted position so the first tip 17.1 is hidden behind the distal surface 11.1. The trigger chassis 26 is in the locking position so that the hook 26.2 engages the rib 18.4 preventing movement of the first sub-module 18.1. The contact part 27.1 extends from the distal surface 11.1 in the distal direction D and the interlock pin 26.4 is engaged in a rear leg of the U-shaped slot 27.3 such that the trigger chassis 26 cannot be moved. The needle return spring 29 is essentially relaxed. In this state, the mechanism rests in an unloaded state with the exception of the drive spring (not shown). The primary package 24 is prevented from being pushed forward by a collar interface 100 between the carrier 70 and the collar 26.1.

Figure 5A:
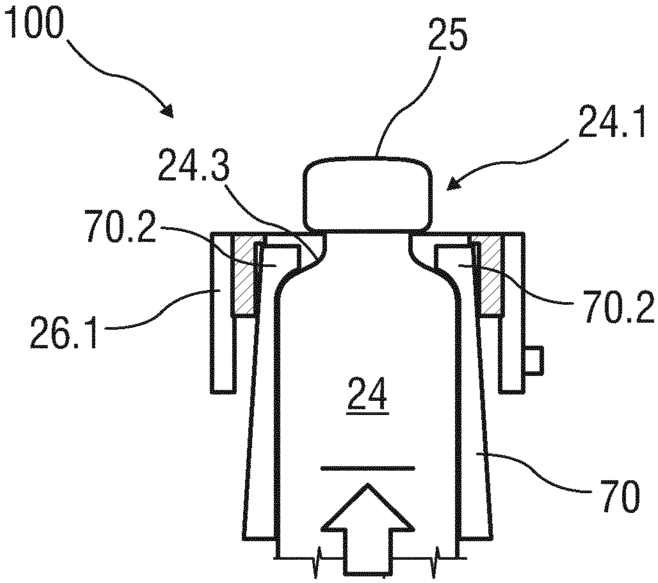
FIG. 5A is a schematic detail view of a collar interface.

FIG. 5A shows details of the collar interface 100. The primary package 24 is held within the carrier 70 by two or more resilient clamps 70.2 on the carrier 70 engaging a neck 24.3 of the primary package 24 near its forward end 24.1. The clamps 70.2 are located within and outwardly supported by the collar 26.1 such that the clamps 70.2 are prevented from being deflected away from the primary package 24 so the primary package 24 cannot move forward relative to the carrier 70.

Figure 6:
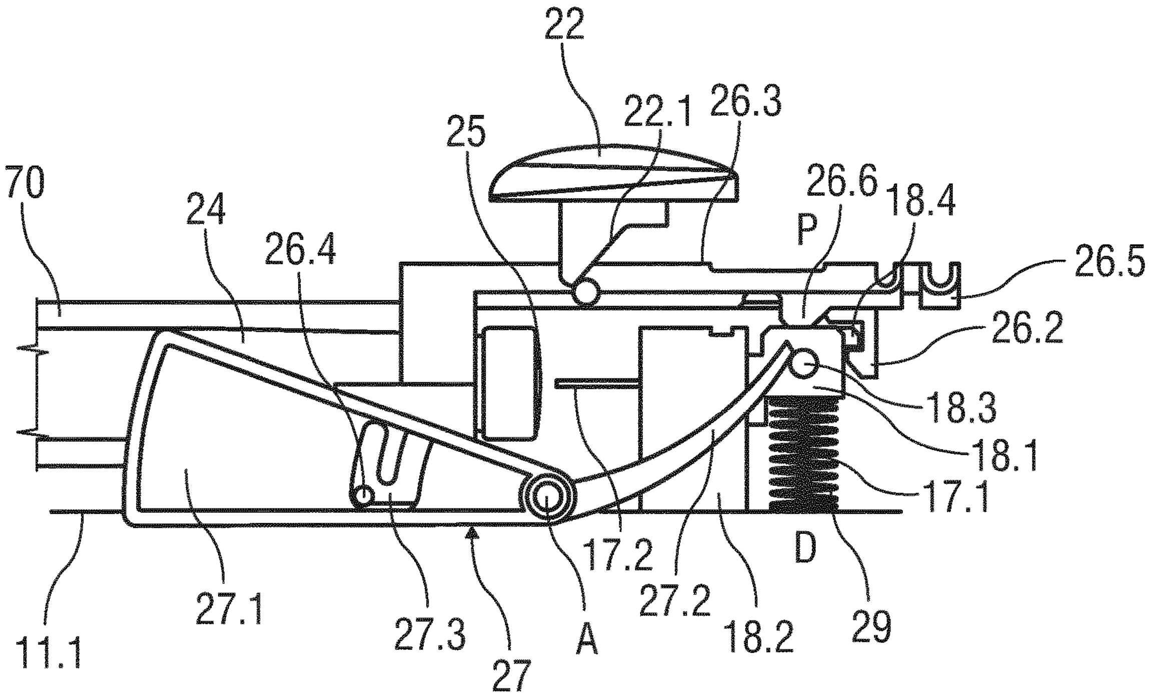
FIG. 6 is a schematic view of the drug delivery device placed with a distal surface on an injection site.

FIG. 6 is a schematic view of the drug delivery device 10 placed with the distal surface 11.1 on an injection site. The contact part 27.1 is depressed into the housing 11 behind the distal surface 11.1 pivoting about the axis A. This resiliently deforms the arm 27.2 placing a pre-load in the distal direction D onto the first sub-module 18.1. However, the first sub-module 18.1 is prevented from moving by the hook 26.2 of the trigger chassis 26. The interlock pin 26.4 has moved down the U-shaped slot 27.3 allowing forward movement of the trigger chassis 26 which is, however, biased rearward by the spring element 26.5.

Figure 7:
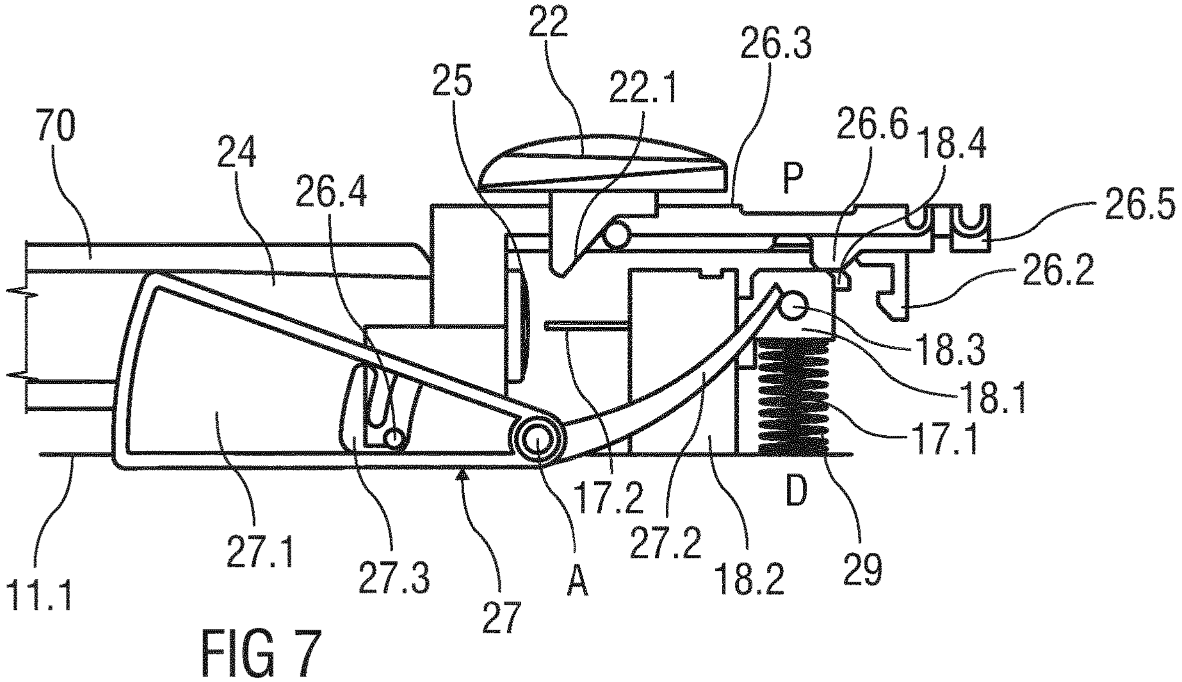
FIG. 7 is a schematic view of the drug delivery device upon depression of a button.
Figure 7A:
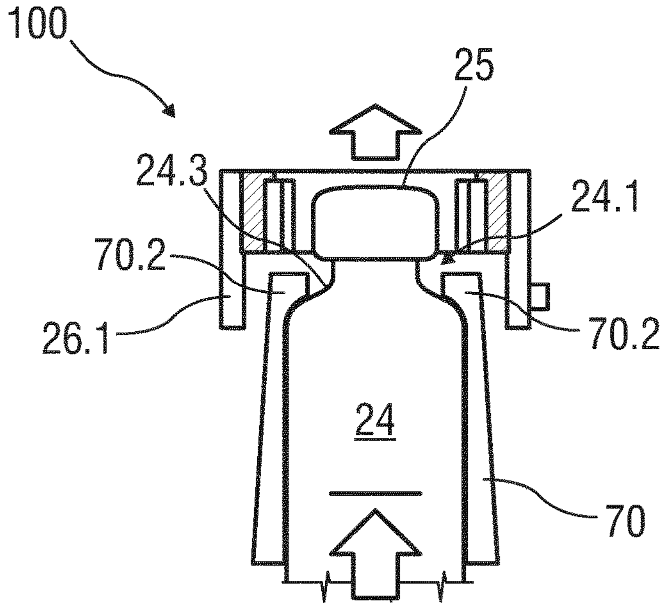
FIG. 7A is a schematic detail view of the collar interface.

FIG. 7 is a schematic view of the drug delivery device 10 upon depression of the button 22 in the distal direction D. The cam surface 22.1 engages the button pin 26.3 and moves the trigger chassis 26 forward into the release position so that the hook 26.2 releases the rib 18.4. Furthermore, movement of the trigger chassis 26 into the release position releases the collar interface 100. FIG. 7A shows that the collar 26.1 is moved forward relative to the carrier 70 such that the collar 26.1 does no longer outwardly support the resilient clamps 70.2 so that the primary package 24 may be moved forward relative to the carrier 70 deflecting the resilient clamps 70.2.

Figure 8:
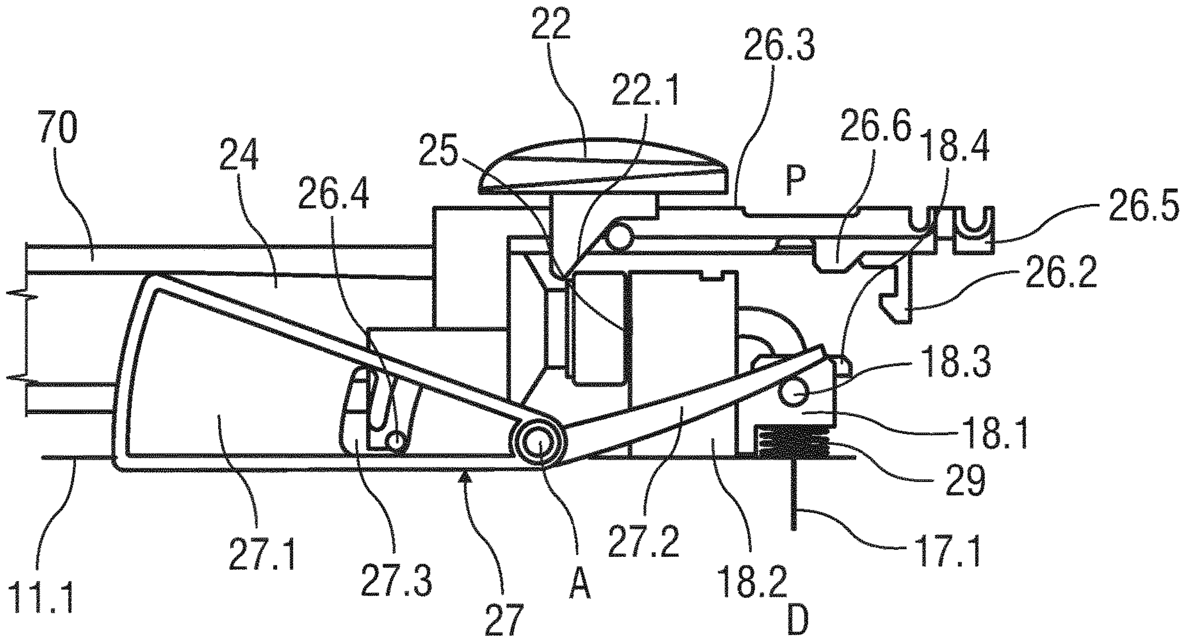
FIG. 8 is a schematic view of the drug delivery device after depression of the button.
Figure 8A:
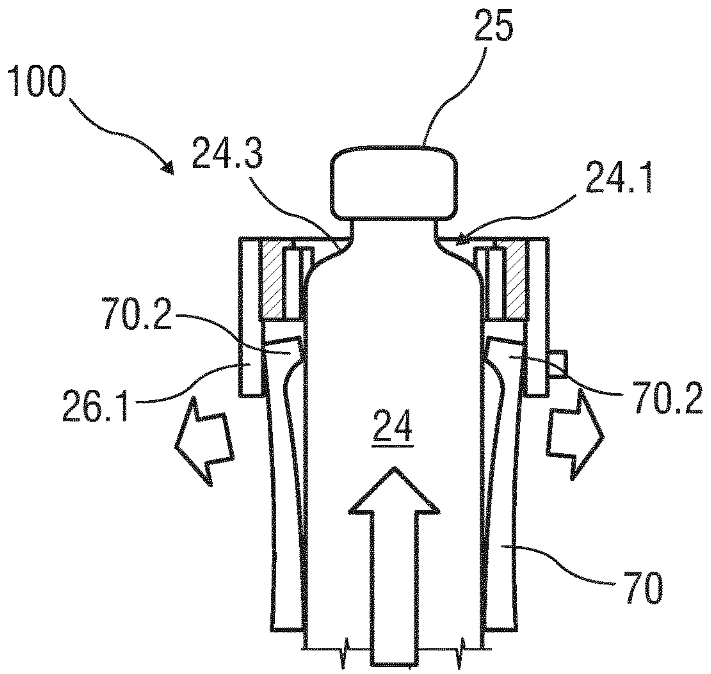
FIG. 8A is a schematic detail view of the collar interface.

FIG. 8 is a schematic view of the drug delivery device 10 after depression of the button 22. The first sub-module 18.1 is moved in the distal direction D forced by the pre-load of the arm 27.2 thus extending the first tip 17.1 of the needle 17 from the distal surface 11.1 into the injection site and pre-loading the needle return spring 29. Simultaneously, the primary package 24 moves forward under load from the drive spring (not shown) such that the second tip 17.2 pierces the septum 25 allowing the drive spring to dispense the dose. FIG. 8A shows the primary package 24 having been moved forward relative to the carrier 70 deflecting the resilient clamps 70.2 which are no longer outwardly supported by the collar 26.1 as the collar 26.1 has been moved forward relative to the carrier 70.

Figure 9:
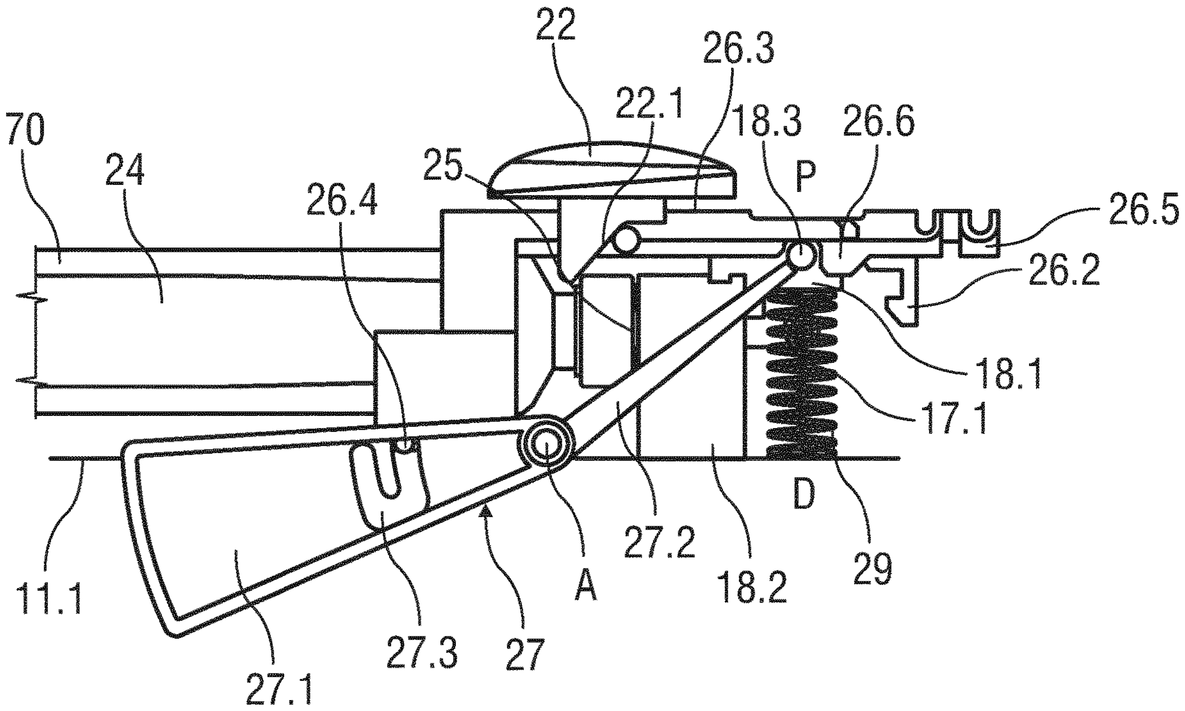
FIG. 9 is a schematic view of the drug delivery device after removal from the injection site.

FIG. 9 is a schematic view of the drug delivery device 10 after removal from the injection site. The contact part 27.1 is no longer depressed so the needle return spring 29 moves the first sub-module 18.1 in the proximal direction P into a second retracted position with the distal tip 17.1 hidden within the housing 11. The second retracted position is proximal from the retracted position as a proximal stop 26.6 on the trigger chassis 26 on which the first sub-module 18.1 abuts when the trigger chassis 26 is in the locking position has been removed due to the movement of the trigger chassis 26 into the release position. In the second retracted position, the protrusion 18.3 on the first sub-module 18.1 disengages the arm 27.2.

Figure 10:
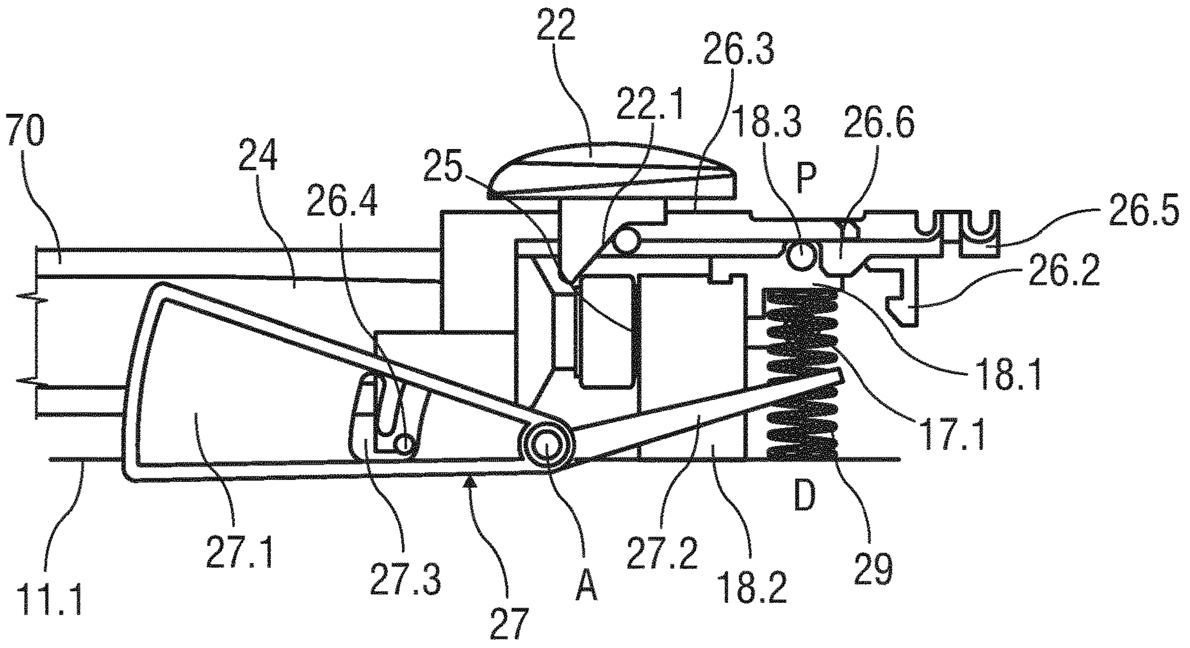
FIG. 10 is a schematic view of the drug delivery device upon depression of a contact part after removal from the injection site.

FIG. 10 is a schematic view of the drug delivery device 10 upon another depression of the contact part 27.1 after removal from the injection site. As the arm 27.2 is no longer coupled to the protrusion 18.3, the contact part 27.1 may be depressed without re-exposing the first tip 17.1 rendering the drug delivery device 10 safe and single use only.

Figure 11:
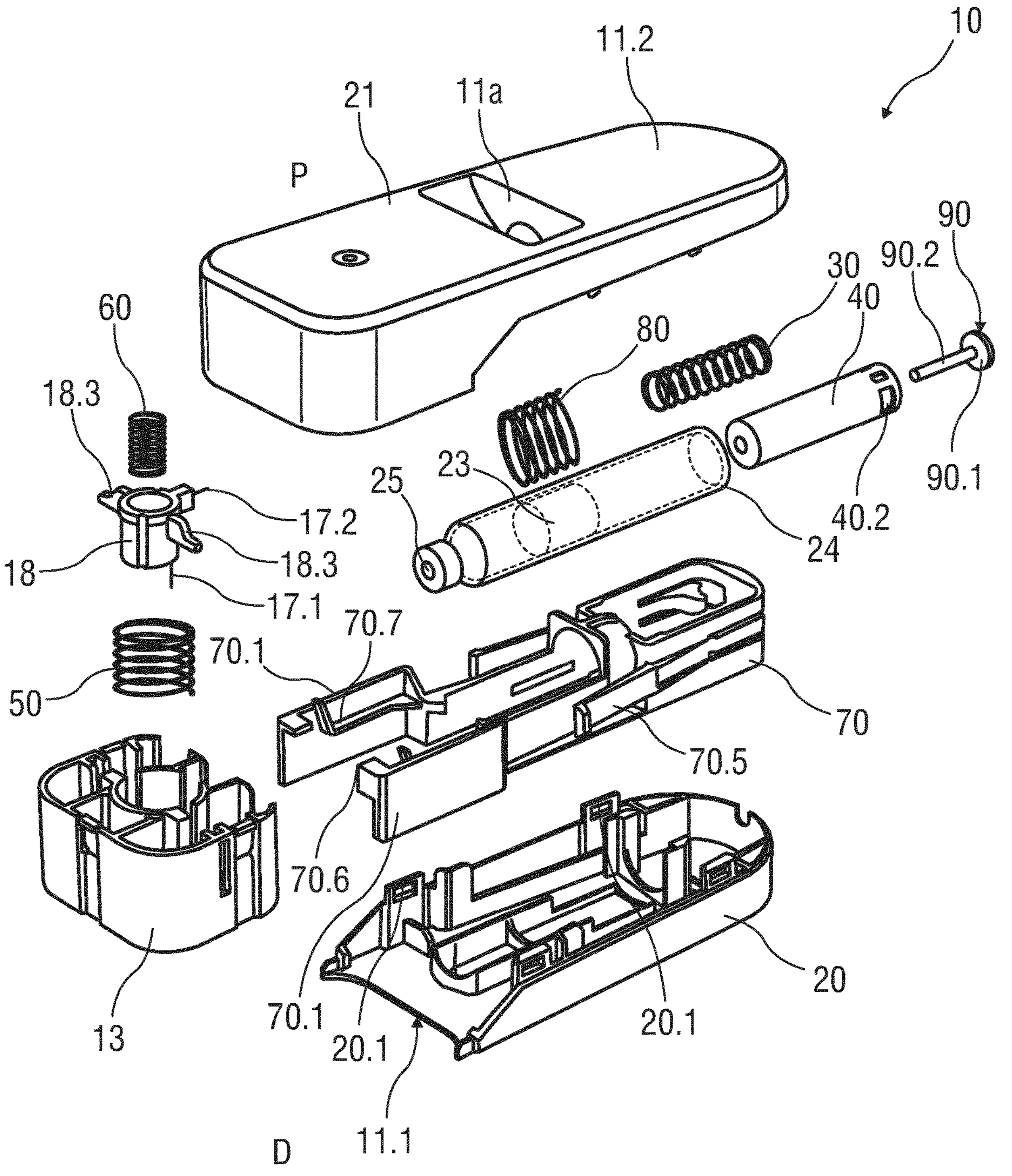
FIG. 11 is a schematic exploded view of another exemplary embodiment of a drug delivery device.

FIG. 11 is a schematic exploded view of another exemplary embodiment of a drug delivery device 10 configured essentially like the one shown in FIG. 2.

The housing 11 comprises a distal region 20 and a proximal region 21, the distal region 20 having the distal surface 11.1 intended to be placed on the injection site. Mutually complementary snap-lock connectors 20.1 (not shown on proximal region) may be provided on the distal region 20 and the proximal region 21 to keep them locked together when assembled.

A shroud spring 50 is arranged to bias the shroud 13 in the distal direction D against the housing 11 or against the needle module 18. A needle spring 60 is arranged to bias the needle module 18 in the distal direction D against the housing 11. The needle module 18 comprises one or more, in particular two, guide protrusions 18.3 adapted to be received in slots 13.1 of the shroud 13 to keep the second tip 17.2 of the needle 17 oriented towards the primary package 24.

A carrier 70 is arranged within the housing 11 to contain the primary package 24 and to allow movement thereof essentially in parallel with the distal surface 11.1 towards the needle module 18. Movement of the primary package 24 towards the needle module 18 may be achieved either by moving the primary package 24 within the carrier 70 or by moving the carrier 70 with the contained primary package 24.

The carrier 70 may comprise one or two forward arms 70.1 adapted to be received within the shroud 13. A respective retention shelf 70.6 is provided on at least one or each forward arm 70.1 adapted to engage one of the guide protrusions 18.3 to prevent movement of the needle module 18 in the distal direction D. Furthermore, at least one or each forward arm 70.1 may comprise an essentially L-shaped guide channel 70.7 adapted to guide the movement of the guide protrusion 18.3 after having been released from the retention shelf 70.6 upon forward movement of the carrier 70. The guide channel 70.7 has a longitudinal section 70.8 essentially in parallel with the distal surface 11.1 to prevent the needle module 18 from returning in the proximal direction P after having been advanced in the distal direction D. A proximal section 70.9 may be provided on the guide channel 70.7 essentially pointing in the proximal direction P. In an exemplary embodiment, the proximal section 70.9 deviates from the proximal direction P in the forward direction such that the proximal section 70.9 is arranged at an angle of between 100 degrees and 120 degrees, in particular about 110 degrees relative to the longitudinal section 70.8.

A drive spring 30 is arranged to bias the plunger 40 to displace the piston 23 within the primary package 24 to deliver a dose. In an exemplary embodiment, the drive spring 30 is arranged within the plunger 40. A carrier spring 80 is arranged to bias the carrier 70 towards the needle module 18. The carrier spring 80 is rearwardly grounded in the distal region 20 of the housing 11 and forwardly bears against the carrier 70.

A noise component 90 may be arranged to provide an audible feedback when the drug has been at least nearly fully expelled from the primary package 24. The noise component 90 comprises a rod adapted to be received within the drive spring 30.

FIGS. 12 to 19 are schematic views of the drug delivery device 10 during assembly.

Figure 12:
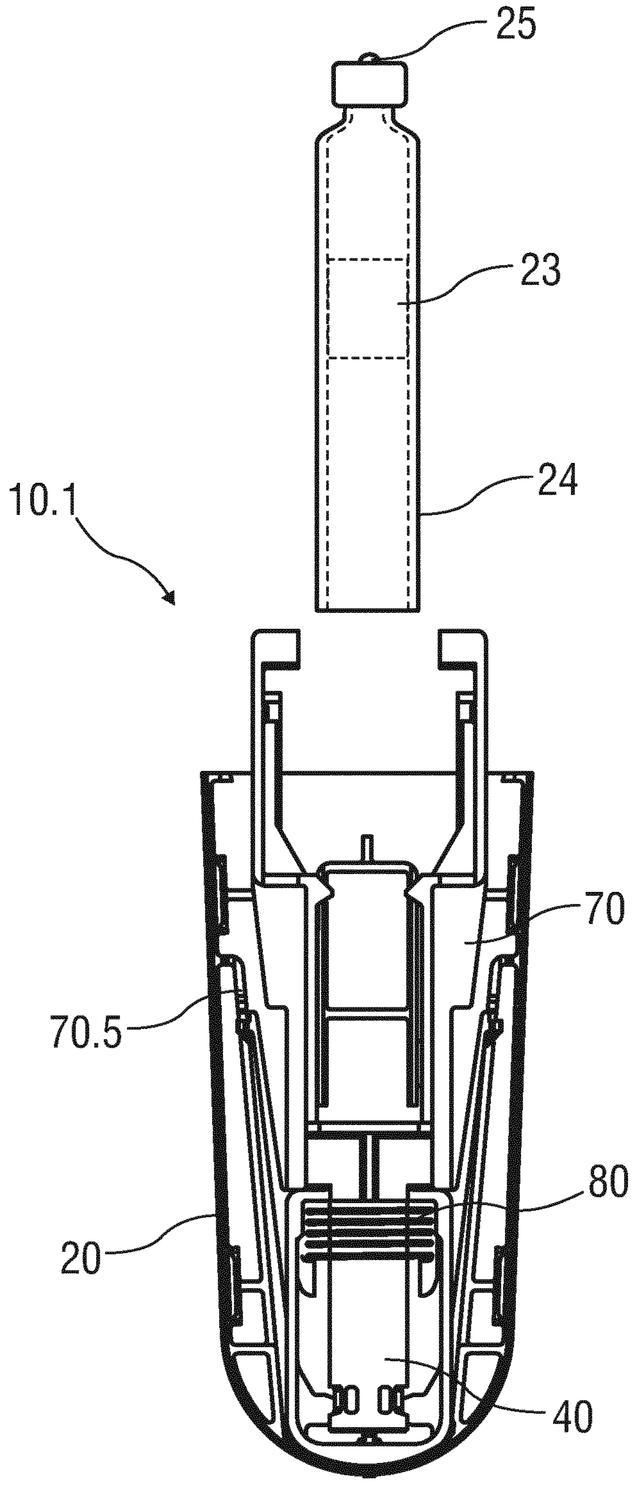
FIG. 12 is a schematic view of a drive subassembly.
Figure 13:
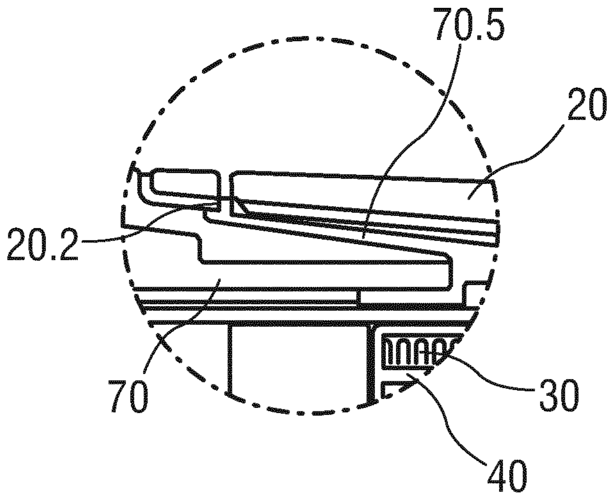
FIG. 13 is a schematic detail view of the drive subassembly.
Figure 14:
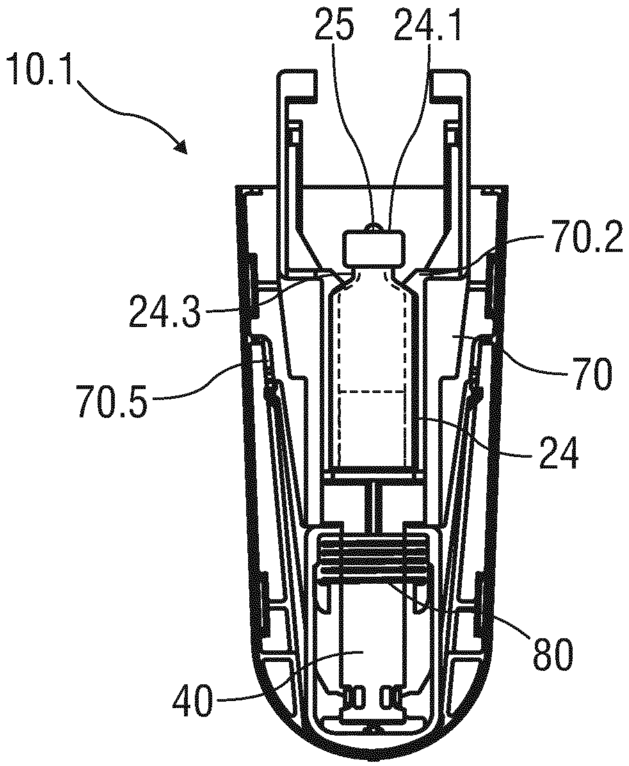
FIG. 14 is a schematic detail view of the drive subassembly with a primary package inserted into a carrier.

In FIG. 12, a drive subassembly 10.1 is shown comprising the distal region 20, the carrier 70, the plunger 40, the carrier spring 80, the drive spring 30 (not visible) and the noise component 90 (not visible). FIG. 13 is a detail view of the drive subassembly 10.1. One or more, in particular two, retention arms 70.5 are provided on the carrier 70 biased outwards toward the distal region 20 of the housing 11 and engage a locking shoulder 20.2 on the distal region 20 to prevent forward movement of the carrier 70 (see detail view). The primary package 24 is prepared to be inserted into the carrier 70 with a rear end 24.2 ahead. In FIG. 14, the primary package 24 has been inserted into the carrier 70. The primary package 24 is held within the carrier 70 by a pair of clamps 70.2 on the carrier 70 engaging a neck 24.3 of the primary package 24 near its forward end 24.1.

Figure 15:
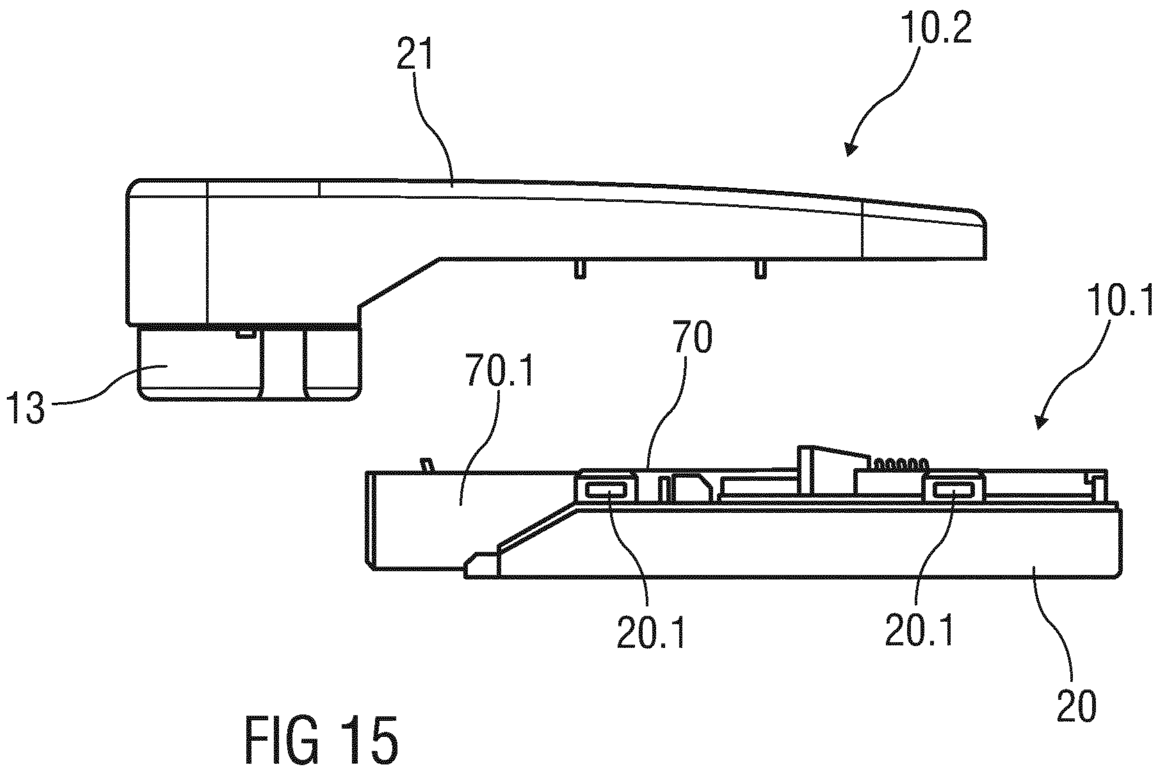
FIG. 15 is a schematic view of the drive subassembly and a control subassembly prior to assembly.

FIG. 15 shows the drive subassembly 10.1 and a control subassembly 10.2 comprising the proximal region 21 with the shroud 13, the needle module 18 (not shown), the needle spring 60 (not shown) and the shroud spring 50 (not shown), wherein the drive subassembly 10.1 and the control subassembly 10.2 are separate from each other.

Figure 16:
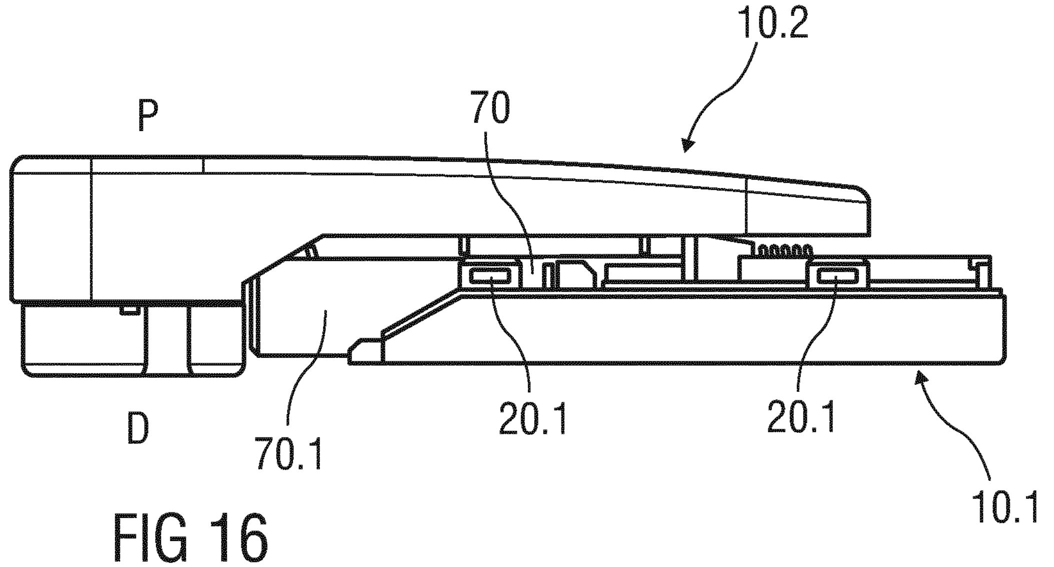
FIG. 16 is a schematic view of the drive subassembly and the control subassembly during assembly.
Figure 17:
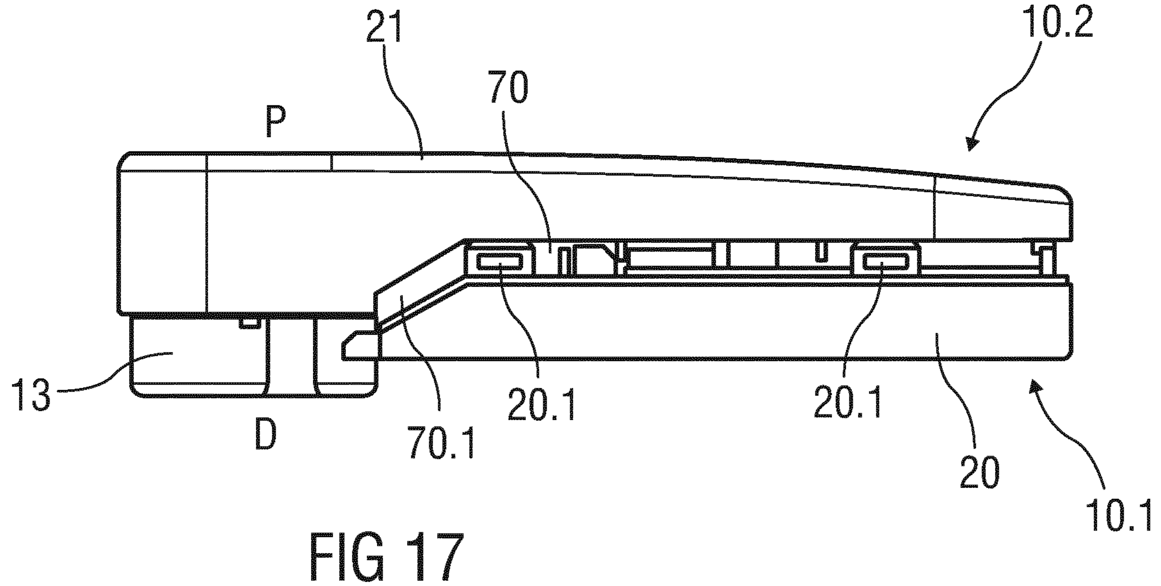
FIG. 17 is a schematic view of the drive subassembly and the control subassembly during assembly.

FIG. 16 shows the drive subassembly 10.1 and control subassembly 10.2 being approached to each other, i.e. the control subassembly 10.2 is moved in the distal direction D towards the drive subassembly 10.1, wherein the forward arms 70.1 of the carrier 70 are spaced from the shroud 13. In FIG. 17, the drive subassembly 10.1 is being moved towards the shroud 13 such that the forward arms 70.1 enter the shroud 13.

Figure 18:
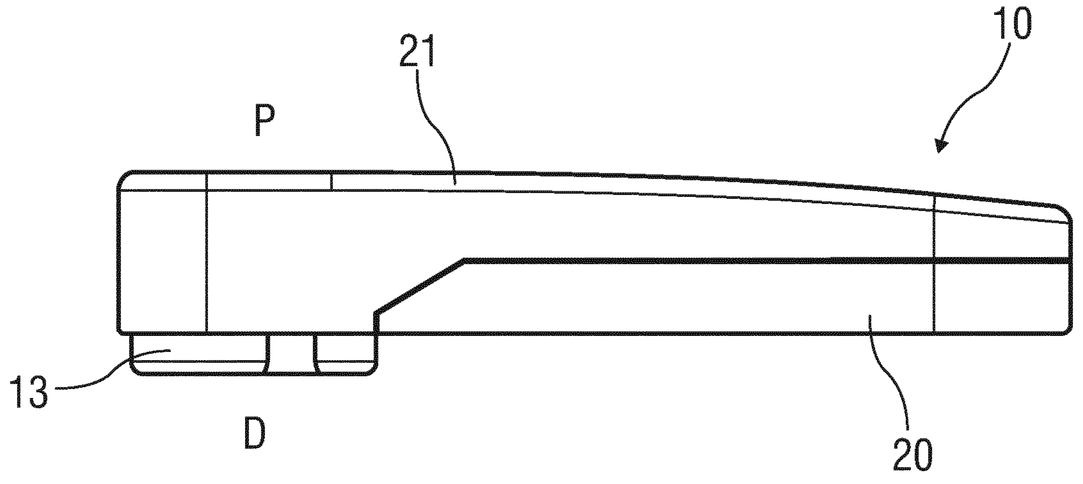
FIG. 18 is a schematic view of the drive subassembly and the control subassembly at the end of assembly.
Figure 19:
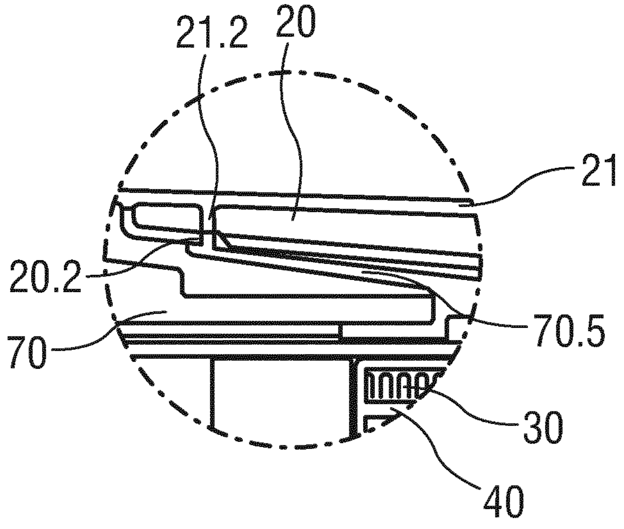
FIG. 19 is a schematic detail view of the drug delivery device at the end of assembly.

In FIG. 18, the control subassembly 10.2 is moved further in the distal direction D towards the drive subassembly 10.1 such that the distal region 20 and the proximal region 21 abut each other and get locked to each other by the snap-lock connectors 20.1. The detail view of FIG. 19 shows that at this point, the retention arms 70.5 are released from the locking shoulder 20.2 by respective ribs 21.2 on the proximal region 21 of the housing 11 displacing the retention arms 70.5 inwards out of engagement with the locking shoulder 20.2. Forward movement of the carrier 70 is prevented by the carrier 70 and the shroud 13 being mutually retained by a hook 13.2 on the shroud 13 as will be shown below. The drug delivery device 10 is thus ready to be used.

FIGS. 20 to 35 are schematic views of the drug delivery device 10 in different states prior to and during use.

Figure 20:
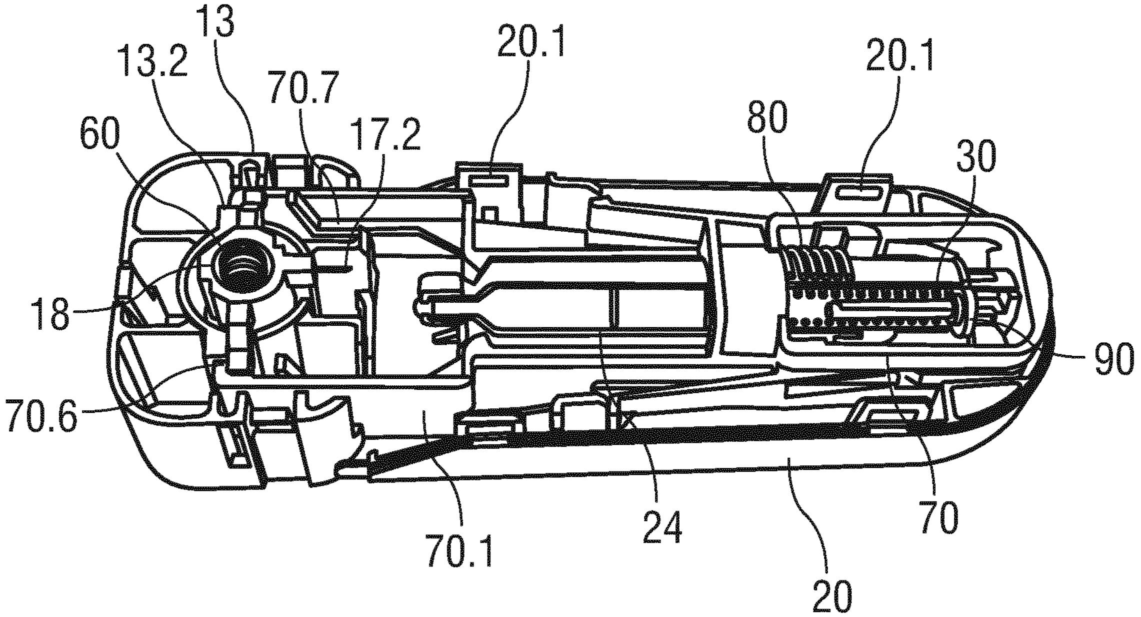
FIG. 20 is a schematic view of the drug delivery device prior to use.
Figure 21:
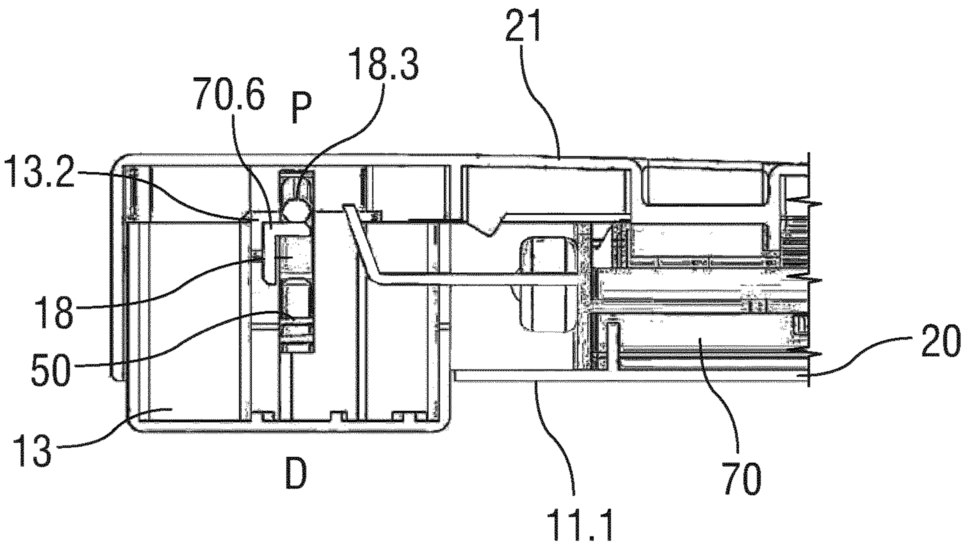
FIG. 21 is a schematic detail view of the drug delivery device prior to use.
Figure 22:
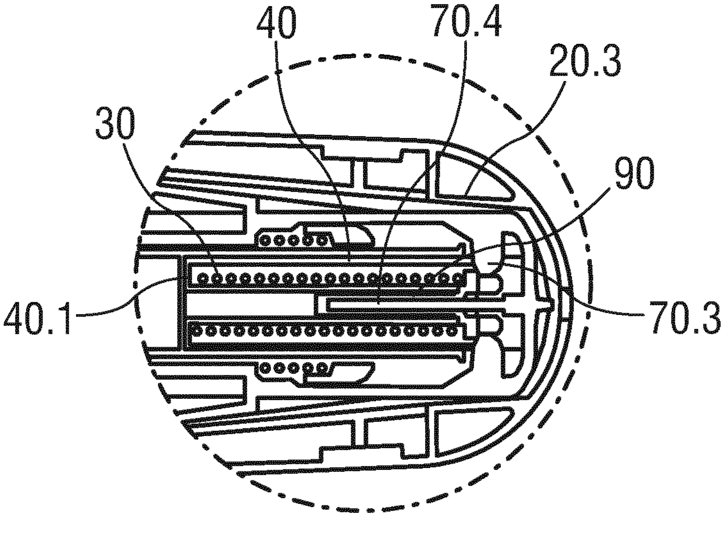
FIG. 22 is a schematic detail view of the drug delivery device prior to use.

In FIG. 20, the drug delivery device 10 is shown in a state prior to use. FIGS. 21 and 22 are respective detail views. The carrier 70 and the shroud 13 may be mutually retained by a hook 13.2 on the shroud 13. The plunger 40 comprises an outer sleeve 40.3 and an inner sleeve 40.4. The drive spring 30 is disposed within the outer sleeve 40.3 but outside the inner sleeve 40.4. The drive spring 30 is compressed between an internal plunger face 40.1 in the forward direction and a flange 90.1 on the noise component 90 in the rearward direction. The flange 90.1 is prevented from moving rearward by one or more resilient carrier clips 70.3 on the carrier 70 which are outwardly supported by casework 20.3 within the distal region 20 of the housing 11. The carrier clips 70.3 may be angled such that the load from the drive spring 30 through the flange 90.1 creates a slight lateral force on the carrier clips 70.3 biasing them outward to disengage the flange 90.1. The noise component 90 comprises a hollow noise rod 90.2 arranged within the inner sleeve 40.4 of the plunger 40. A carrier rod 70.4 is provided on the rear end of the carrier 70 directed in the forward direction into the hollow noise rod 90.2 of the noise component 90. The noise rod 90.2 is split along its length forming two or more resilient arms 90.3 biased outwards. As long as the arms 90.3 are within the inner sleeve 40.4 they are prevented from moving outwards. Forward ends 90.4 of the arms 90.3 comprise an inwardly directed protrusion engaging the carrier rod 70.4 such that the noise rod 90.2 cannot move in the rearward direction relative to the carrier 70 prior to outward deflection of the arms 90.3. The carrier clips 70.3 engage the flange 90.1 through lateral apertures 40.2 in the plunger 40 preventing the plunger 40 from advancing forward.

Figure 23:
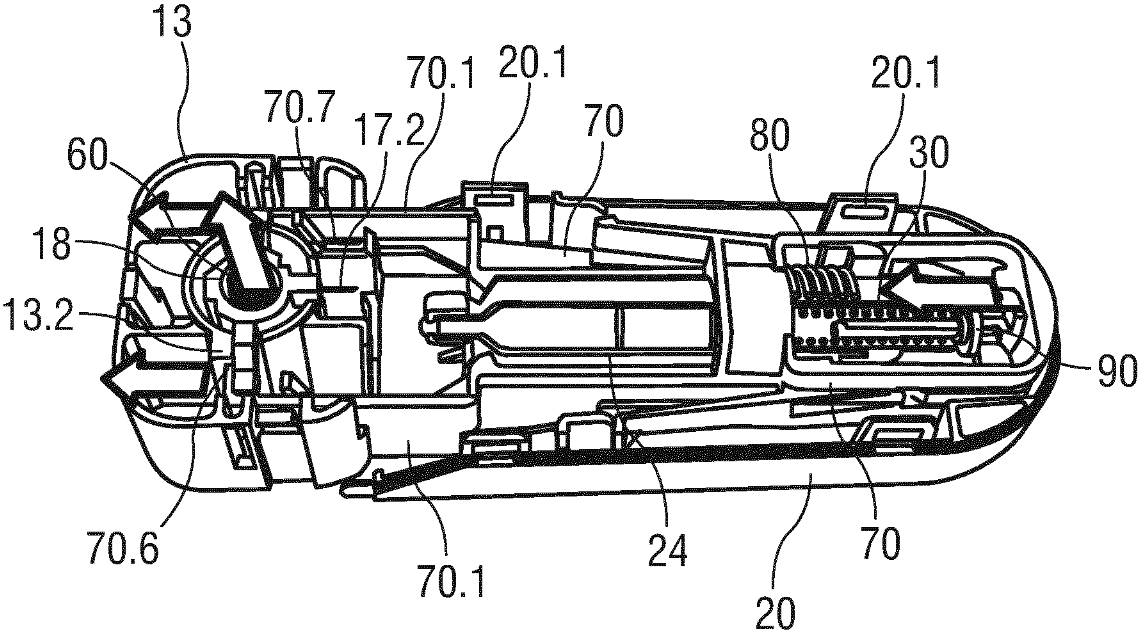
FIG. 23 is a schematic view of the drug delivery device during depression of a shroud.
Figure 24:
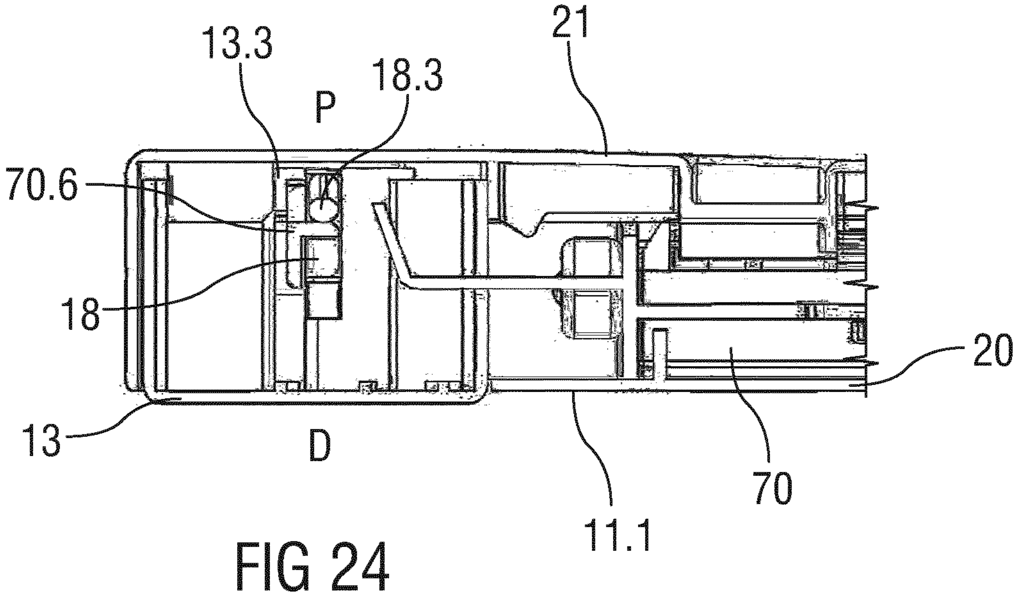
FIG. 24 is a schematic detail view of the drug delivery device during depression of a shroud.

In FIG. 23, the shroud 13 is being depressed, i.e. by the distal surface 11.1 being pushed against an injection site. FIG. 24 is a respective detail view. Due to this depression, the hooks 13.2 release the forward arms 70.1 allowing the carrier 70 to move forwards, pushed by the carrier spring 80. The retention arms 70.5 do not prevent movement of the carrier 70 in this state as they have been unlocked during final assembly of the drug delivery device 10 by respective ribs 21.2 on the proximal region 21 of the housing 11 displacing the retention arms 70.5 inwards out of engagement with the locking shoulder 20.2.

Figure 25:
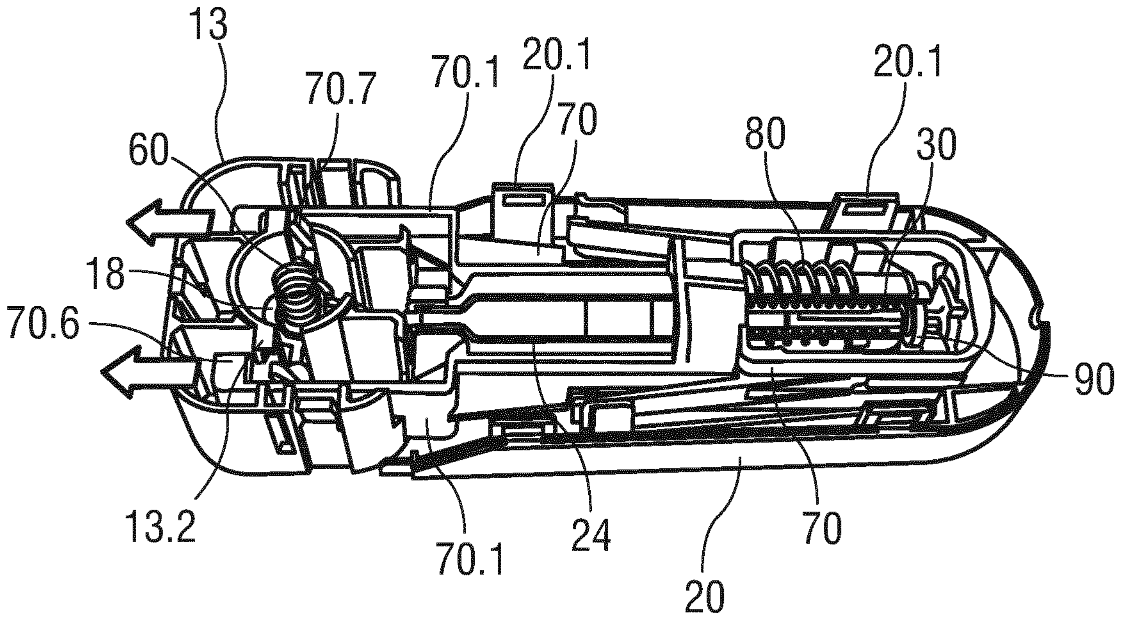
FIG. 25 is a schematic view of the drug delivery device during forward movement of the carrier.
Figure 26:
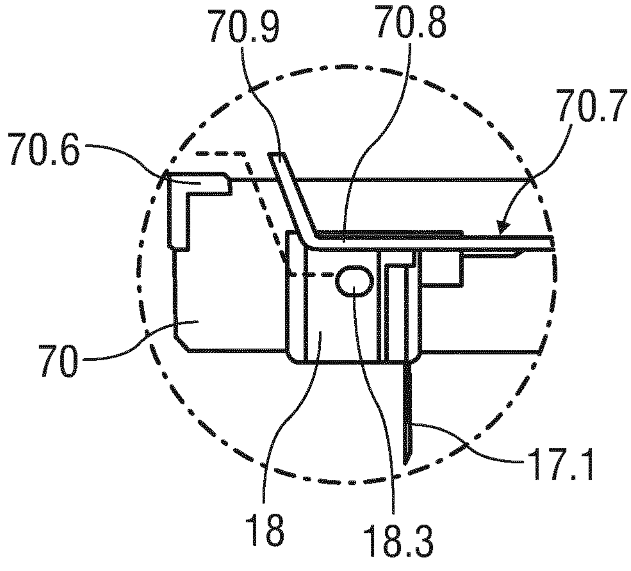
FIG. 26 is a schematic detail view of the drug delivery device during forward movement of the carrier.

FIG. 25 shows the drug delivery device 10 during forward movement of the carrier 70. The detail view of FIG. 26 shows that the forward movement of the carrier 70 releases the needle module 18 from the retention shelf 70.6 on the carrier 70 allowing the guide protrusions 18.3 on the needle module 18 to enter the guide channel 70.7 so that the needle module 18 is moved in the distal direction D driven by the needle spring 60 so the distal tip 17.1 of the needle extends from the shroud 13 and can be inserted into the injection site. The proximal section 70.9 on the guide channel 70.7 restrains further forward movement of the carrier 70 by engaging the guide protrusions 18.3 until the needle 17 has reached an insertion depth. At this point, the carrier 70 moves further forward such that the guide protrusion 18.3 is engaged by the longitudinal section 70.8 which prevents the needle 17 from returning in the proximal direction P. The shroud spring 50 acts between the shroud 13 and a primarily cylindrical distally protruding feature on the inner surface of the proximal region 21 of the housing 11. At the point of needle insertion, this feature from the proximal region 21 sits coplanar to the guide protrusions 18.3 on the needle module 18, ensuring that the shroud spring 50 never prevents insertion nor affects position of the needle 17. This allows for a small and compact needle spring 60.

Figure 27:
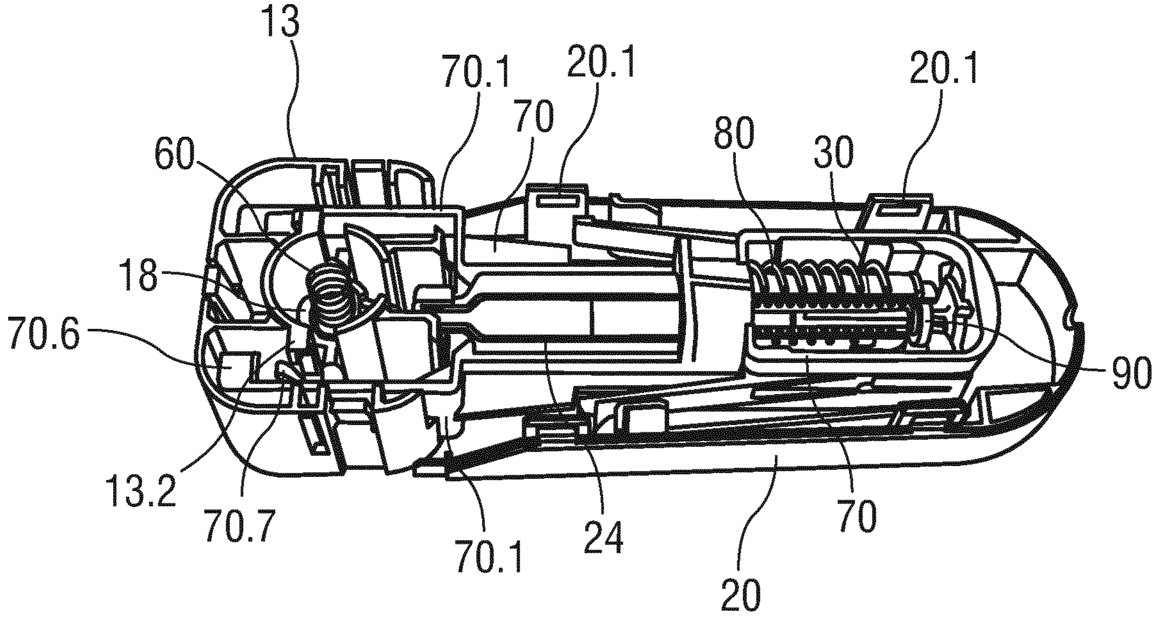
FIG. 27 is a schematic view of the drug delivery device with the carrier having been moved forward.
Figure 28:
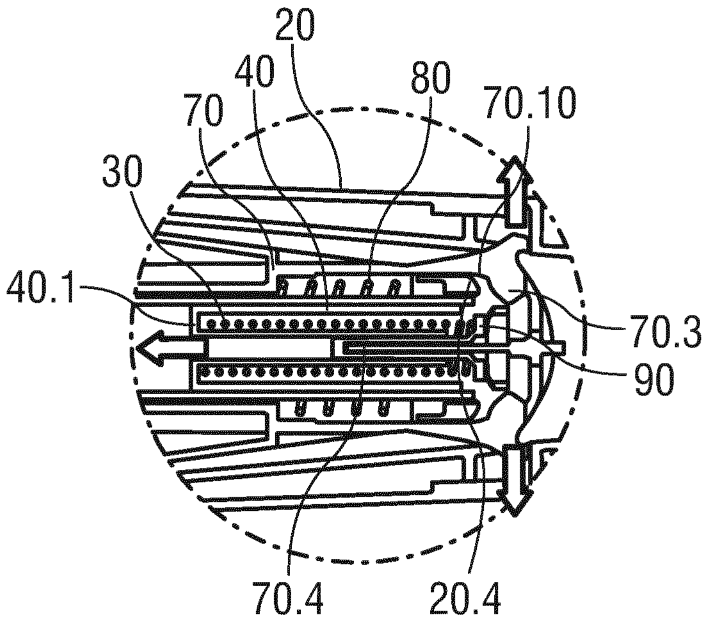
FIG. 28 is a schematic detail view of the drug delivery device with the carrier having been moved forward.

In FIG. 27, the carrier 70 has been moved forward with the primary package 24 which is fixed to the carrier 70 to such an extent that the second tip 17.2 of the needle 17 pierces the septum 25 establishing a fluid communication between the cavity within the primary package 24 and the needle 17. The detail view of FIG. 28 shows that due to the movement of the carrier 70 the carrier clips 70.3 are no longer outwardly supported by the casework 20.3 and deflect outwards forced by the drive spring 30 such that the carrier clips 70.3 disengage the apertures 40.2 and thus unlock the plunger 40 which is advanced forward by the drive spring 30 to deliver the drug. The forward ends 90.4 of the arms 90.3 of the noise rod 90. 2 resolve the force of the drive spring 30 via the carrier rod 70.4 which they cannot disengage due to the inner sleeve 40.4 of the plunger 40 preventing outward deflection of the arms 90.3. If the carrier clips 70.3 should fail to deflect due to the force from the drive spring 30, one or more ramps 20.4, 70.10 on the housing 11, e.g. on the distal region 20, and on the carrier 70 may be configured to deflect the carrier clips 70.3 when the carrier 70 is being moved further forward.

Figure 29:
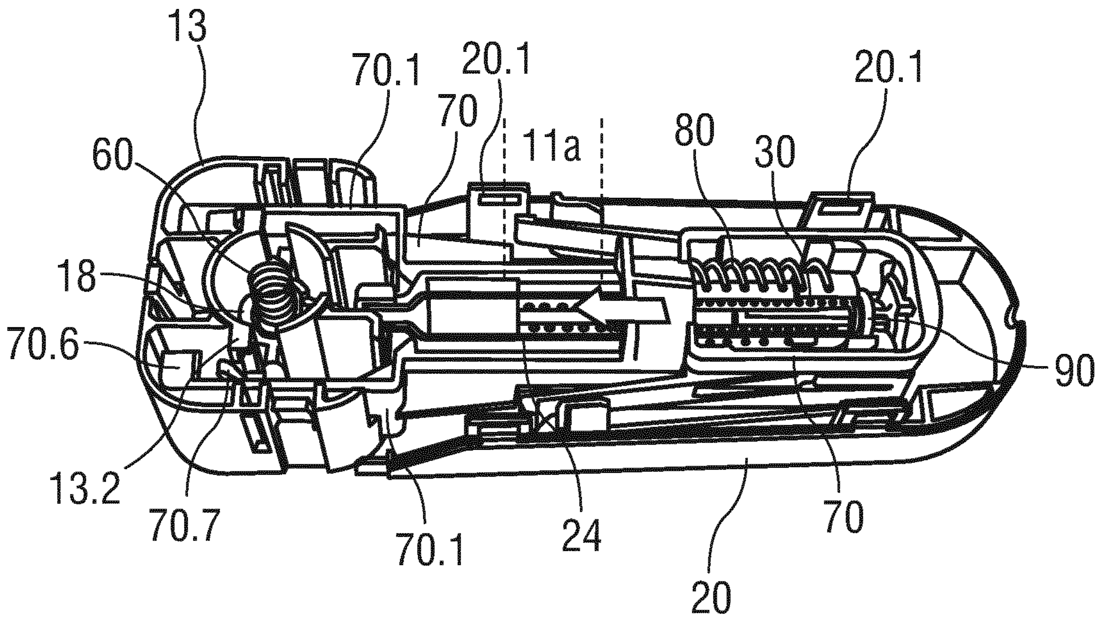
FIG. 29 is a schematic view of the drug delivery device during forward movement of a plunger.
Figure 30:
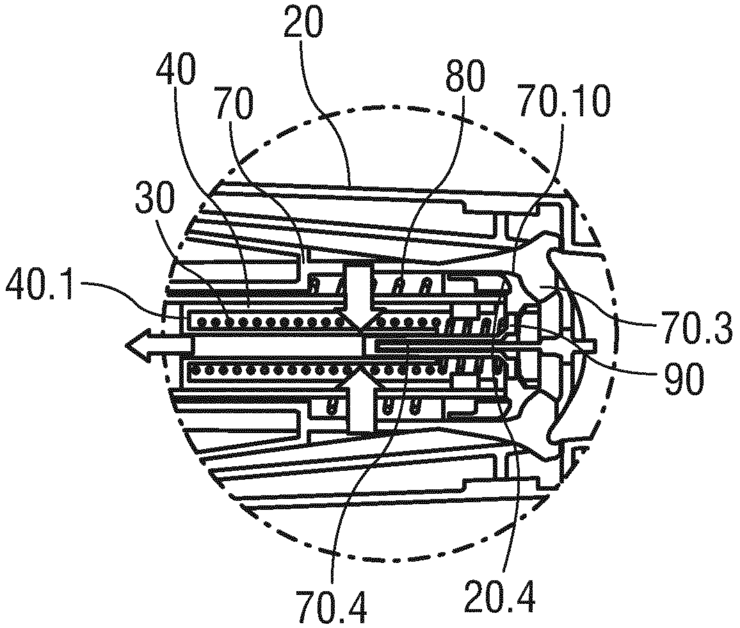
FIG. 30 is a schematic detail view of the drug delivery device during forward movement of the plunger.

FIG. 29 shows the plunger 40 being advanced in the forward direction. FIG. 30 is a respective detail view. During this movement, the plunger 40, which may have an eye-catching colour, e.g. yellow, appears in the window 11*a* whose position is shown at 11*a*.

Figure 31:
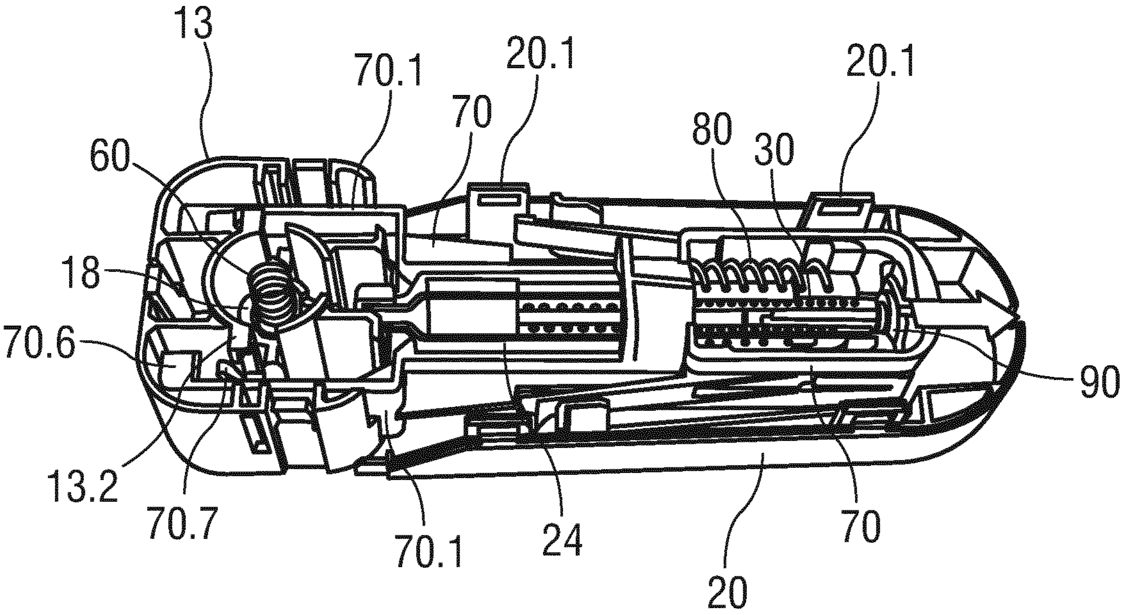
FIG. 31 is a schematic view of the drug delivery device with the plunger having been moved forward.
Figure 32:
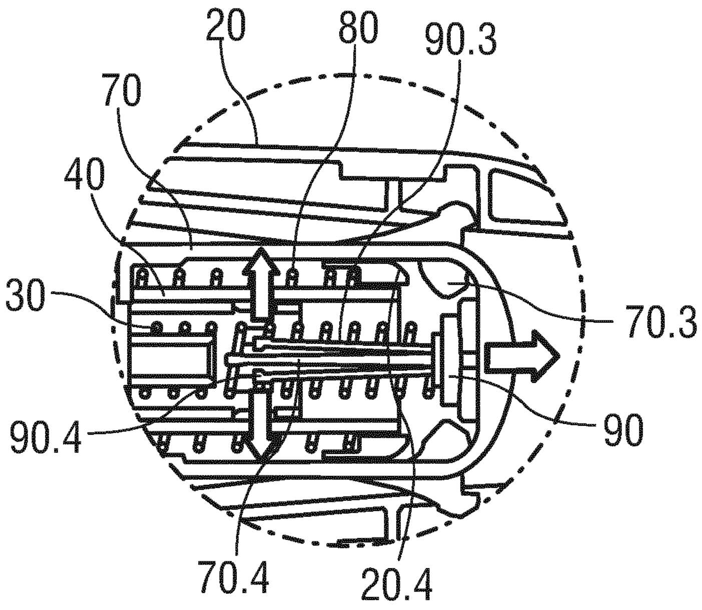
FIG. 32 is a schematic detail view of the drug delivery device with the plunger having been moved forward.

FIG. 31 and the respective detail view of FIG. 32 show the plunger 40 having been fully advanced forward to expel the drug. This has removed the inner sleeve 40.4 of the plunger 40 from the arms 90.3 of the noise rod 90.2 so they deflect outward and their forward ends 90.4 disengage the carrier rod 70.4. The noise component 90 is thus released to be moved in the rearward direction driven by the residual force of the drive spring 30 and impact a rear end of the carrier 70 thus creating a click noise indicating the end of dose.

Figure 33:
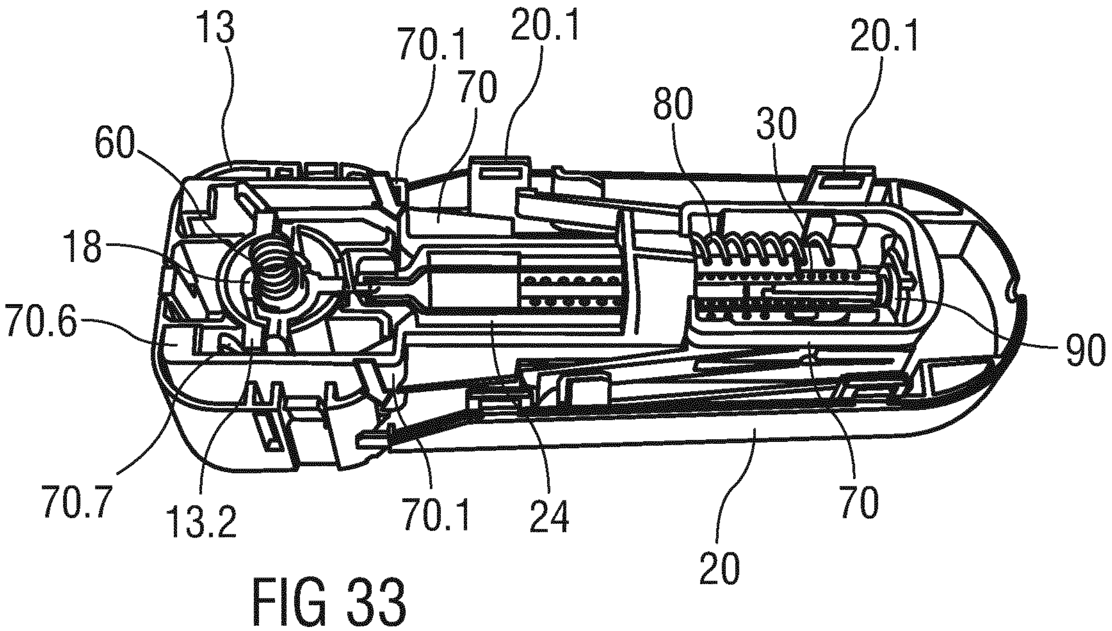
FIG. 33 is a schematic view of the drug delivery device removed from the injection site.
Figure 34:
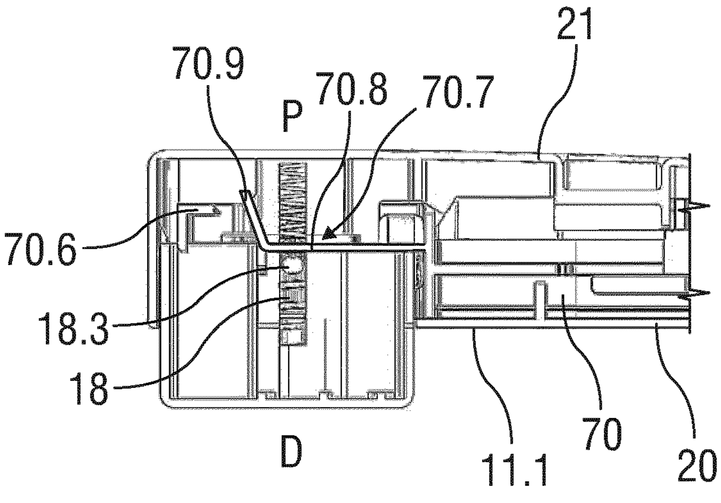
FIG. 34 is a schematic detail view of the drug delivery device removed from the injection site.
Figure 35:
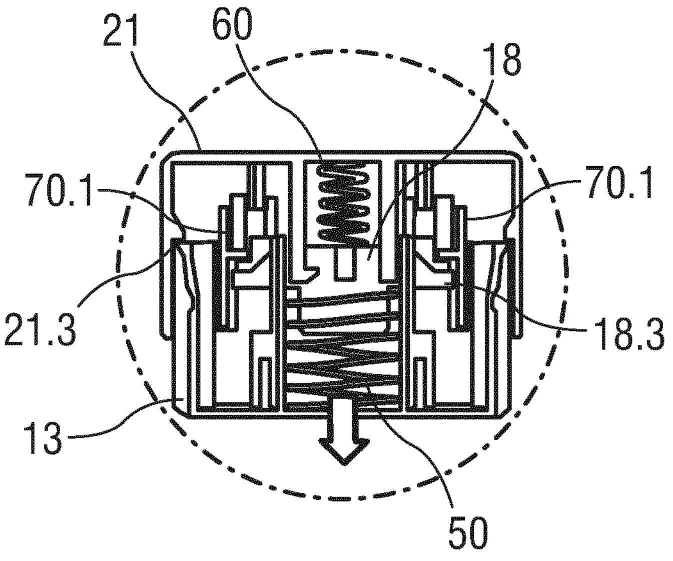
FIG. 35 is a schematic detail view of the drug delivery device removed from the injection site.

In FIG. 33, the drug delivery device 10 is removed from the injection site. FIGS. 34 and 35 are respective detail views. The shroud 13 is moved in the distal direction D driven by the shroud spring 50. In this state, the shroud 13 extends further from the distal surface 11.1 than prior to use due to the retention shelf 70.6 of the carrier 70 no longer engaging the hook 13.2 to be able to cover the still extended needle 17. The retention shelf 70.6 may be broader than the sections 70.8, 70.9 of the guide channel 70.7 in a transversal direction perpendicular to the longest axis of the drug delivery device 10 and perpendicular to an axis defined by the distal direction D and the proximal direction P thus allowing the retention shelf 70.6 to engage the hook 13.2 while the guide channel 70.7 does not interact with the hook 13.2.

One or more clips 21.3 on the housing 11, e.g. on the proximal region 21 thereof, engage the shroud 13 to prevent it from returning in the proximal direction P from this position.

Figure 36:
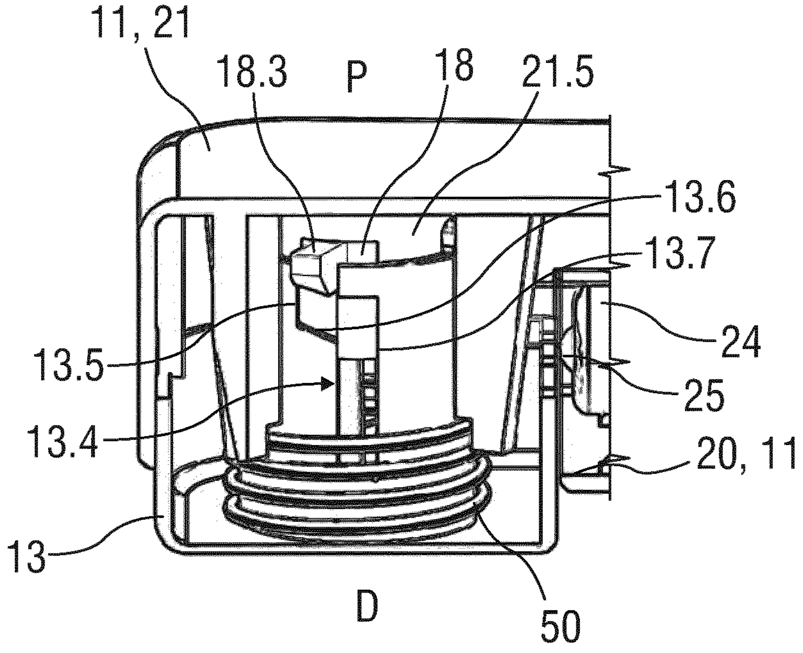
FIG. 36 is a schematic detail view of another exemplary embodiment of the drug delivery device.

FIG. 36 is a schematic detail view of another embodiment of the drug delivery device 10.

A shroud 13 is slidably disposed in the housing 11 between an extended position and a retracted position. In the extended position the shroud 13 extends from the distal surface 11.1. A needle module 18 having a needle 17 with a first tip (not shown) and a second tip (not shown) is provided, the first tip adapted to be extended from the distal surface 11.1 and the second tip adapted to point towards a primary package 24 to pierce a septum 25 thereof. The needle module 18 is movable from a retracted position in the distal direction D into an extended position and vice versa in the proximal direction P. The shroud 13 is adapted to cover the first tip when both are in their extended positions.

A needle spring 60 is arranged to bias the needle module 18 with the first tip of the needle 17 in the distal direction D towards the extended position.

The needle module 18 comprises at least one protrusion 18.3 adapted to engage a ramped surface 21.4 (best seen in FIG. 39) on the housing 11, e.g. on the proximal region 21. The ramped surface 21.4 may be part of a tube 21.5 extending within the housing 11, e.g. from the proximal region 21, in the distal direction D. The tube 21.5 may be adapted to retain the needle module 18 which may have a corresponding cylindrical shape such that it can rotate within the tube 21.5. A needle spring (not shown) is provided to bias the needle module 18 in the distal direction D. When the needle module 18 is in the retracted position, the bias of the needle spring and the protrusion 18.3 engaging the ramped surface 21.4 subject the needle module 18 to a torque in a first rotational direction R1 to disengage the protrusion 18.3 from the ramped surface 21.4. The shroud 13 comprises an inner sleeve 13.3 having a cylindrical shape telescoped with the tube 21.5. The inner sleeve 13.3 comprises a slot 13.4 having a proximal section 13.5 extending in the proximal direction P and the distal direction D and aligned with the ramped surface 21.4 of the tube 21.5, a circumferential section 13.6 distally adjacent the proximal section 13.5 and extending in the first rotational direction R1, and a distal section 13.7 distally adjacent the circumferential section 13.6 extending in the distal direction D and not aligned with the proximal section 13.5. When the shroud 13 is in the extended position, the protrusion 18.3 is within the proximal section 13.5 and cannot move in the first rotational direction R1 such that despite the torque it cannot disengage the ramped surface 21.4 such that the needle module 18 which is in its retracted position is prevented from moving in the distal direction D. The circumferential section 13.6 may comprise a ramped surface which may align with the ramped surface 21.4 on the housing 11.

A shroud spring 50 is arranged to bias the shroud 13 in the distal direction D towards the extended position against the housing 11.

Figure 37:
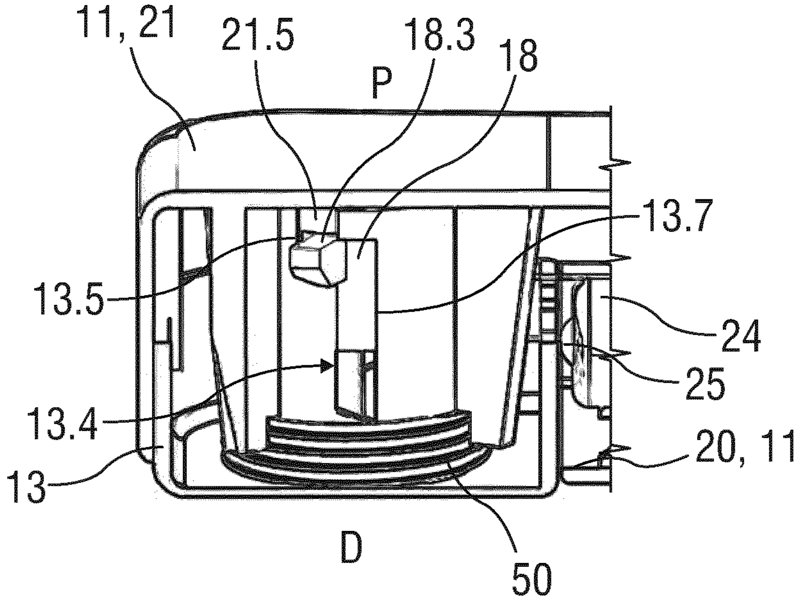
FIG. 37 is a schematic detail view of the drug delivery device with a shroud depressed in a retracted position.

FIG. 37 is a schematic detail view of the drug delivery device 10 with the shroud 13 depressed in the retracted position. This may be achieved by pushing the drug delivery device 10 with the distal surface 11.1 on an injection site. As the shroud 13 is being depressed, the shroud spring 50 is pre-loaded and the protrusion 18.3 travels down the proximal section 13.5 of the slot 13.4 until arriving in the circumferential section 13.6. This allows the protrusion 18.3 to move in the first rotational direction R1 along the circumferential section 13.6 and disengage the ramped surface 21.4 due to the torque on the needle module 18. As the protrusion 18.3 reaches the distal section 13.7 of the slot 13.4 during this movement, the needle module 18 is free to move in the distal direction D towards the extended position.

Figure 38:
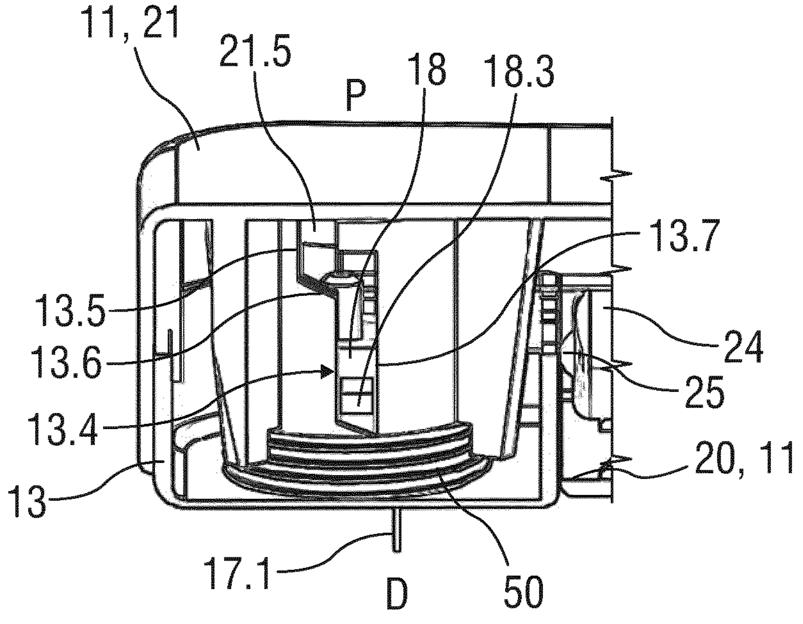
FIG. 38 is a schematic detail view of the drug delivery device with a needle module in an extended position.

FIG. 38 is a schematic detail view of the drug delivery device 10 with the needle module 18 in the extended position. The first tip 17.1 of the needle 17 can be seen to extend beyond the distal surface 11.1 to be inserted into the injection site. A distal end of the distal section 13.7 may define a stop for the protrusion 18.3 thus also defining a needle insertion depth.

The protrusion 18.3 may also be adapted to engage a carrier release interface (e.g. the one shown in FIG. 42) to release a carrier holding the primary package 24 at the end of the extension movement of the needle module 18 to allow the primary package 24 to move forward to pierce the septum 25 by the second tip of the needle and to displace the drug from the primary package 24, driven by a drive spring 30.

Figure 39:
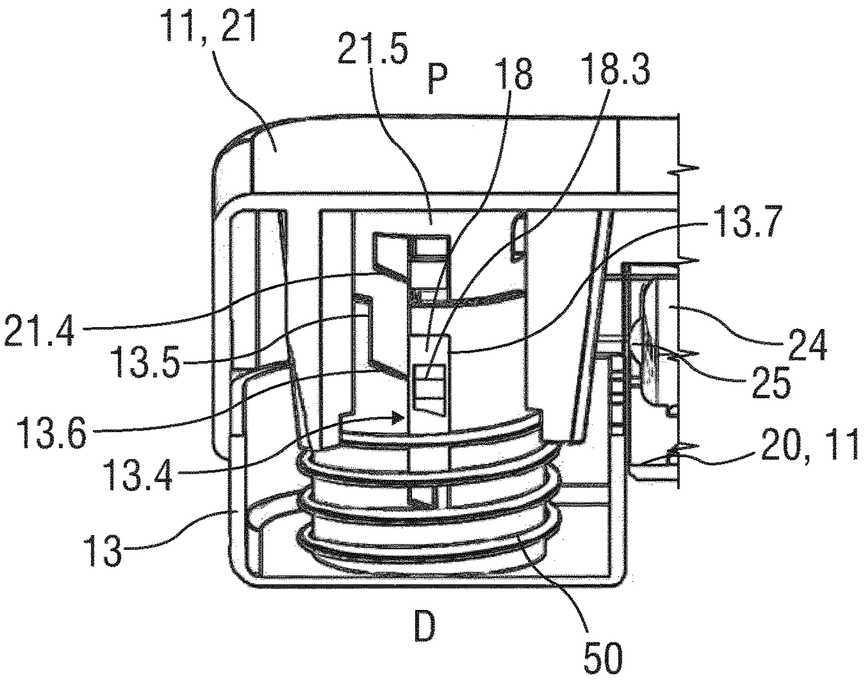
FIG. 39 is a schematic detail view of the drug delivery device having been removed from the injection site.

FIG. 39 is a schematic detail view of the drug delivery device 10 having been removed from the injection site. This allows the shroud 13 to move into a second extended position driven by the shroud spring 50 to cover the extended first tip 17.1 of the needle. The second extended position may be distal from the extended position of the shroud 13. The extended position may be defined by the carrier arms. The second extended position may be defined via locking clips and hard stops against the casework. Lock features similar to the one or more clips 21.3 on the housing 11, e.g. on the proximal region 21 thereof described above, may be provided to engage the shroud 13 to prevent it from returning in the proximal direction P from this position. The needle module 18 may be retained via annular snap features within the tube 21.5.

Figure 40:
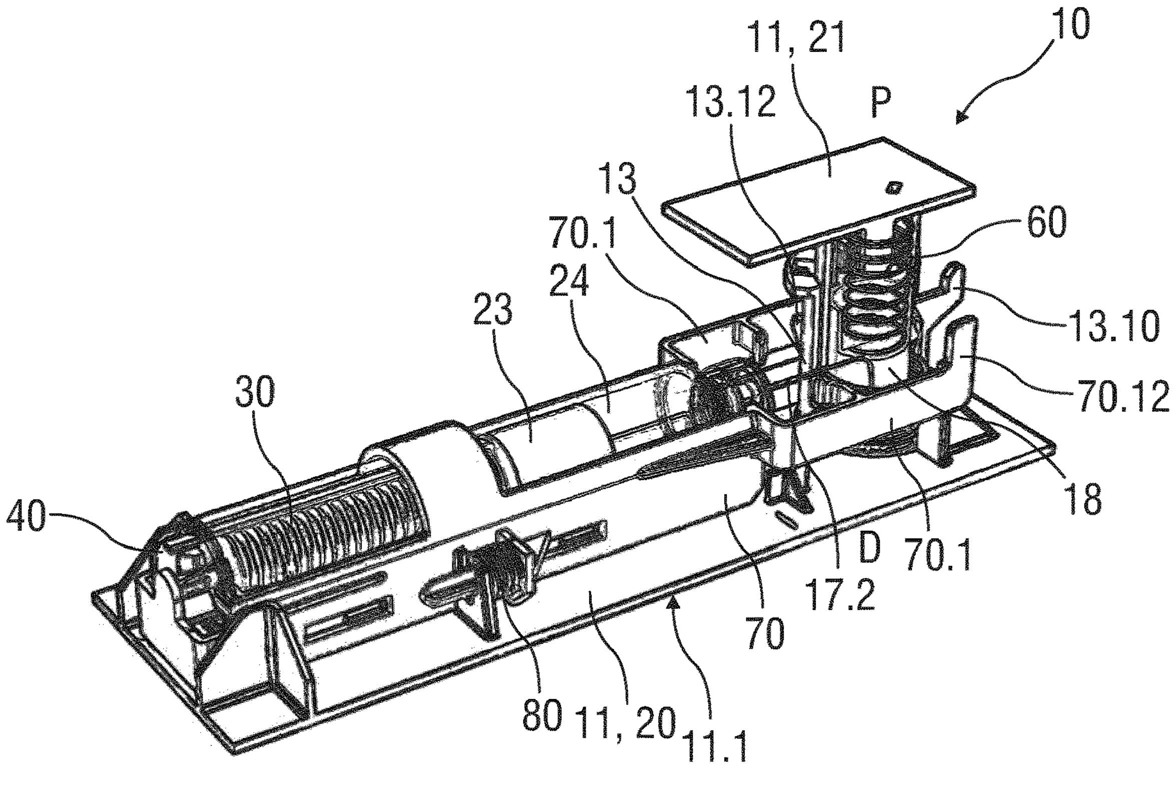
FIG. 40 is a schematic view of another exemplary embodiment of the drug delivery device.
Figure 41:
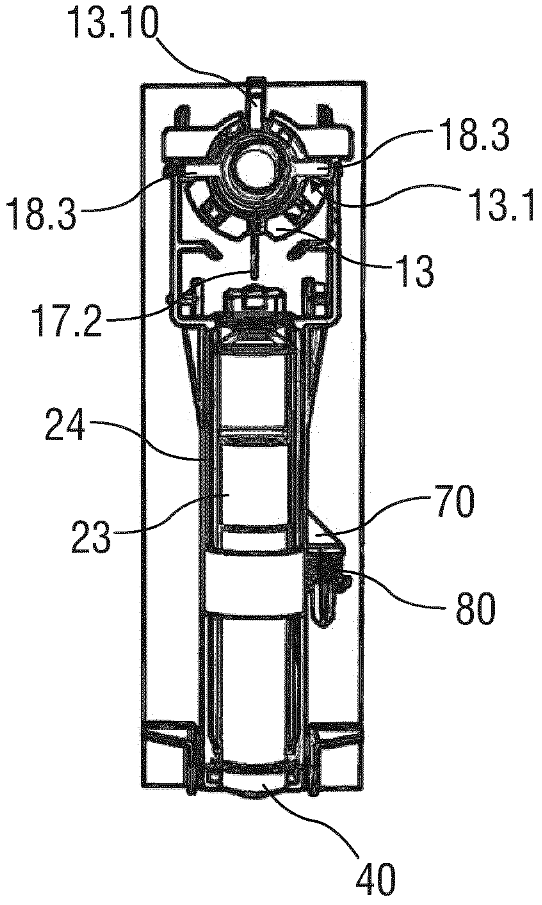
FIG. 41 is another schematic view of the drug delivery device.
Figure 42:
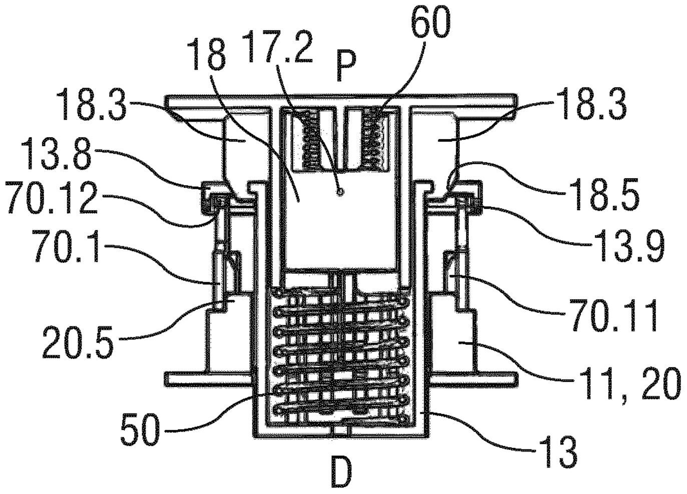
FIG. 42 is a schematic detail view of the drug delivery device.

FIGS. 40 and 41 are schematic views of another exemplary embodiment of a drug delivery device 10. FIG. 42 is a respective detail view.

The drug delivery device 10 may be configured essentially like the one shown in FIG. 2.

The housing 11 comprises a distal region 20 and a proximal region 21, the distal region 20 having the distal surface 11.1 intended to be placed on the injection site. Mutually complementary snap-lock connectors (not shown) may be provided on the distal region 20 and the proximal region 21 to keep them locked together when assembled.

A shroud spring 50 is arranged to bias the shroud 13 in the distal direction D against the housing 11. A needle spring 60 is arranged to bias the needle module 18 in the distal direction D against the housing 11. The needle module 18 comprises one or more, in particular two, guide protrusions 18.3 adapted to be received in slots 13.1 of the shroud 13 to keep the second tip 17.2 of the needle 17 oriented towards the primary package 24.

A carrier 70 is arranged within the housing 11 to contain the primary package 24 and to allow movement thereof essentially in parallel with the distal surface 11.1 towards the needle module 18. Movement of the primary package 24 towards the needle module 18 may be achieved either by moving the primary package 24 within the carrier 70 or by moving the carrier 70 with the contained primary package 24.

The carrier 70 may comprise one or two resilient forward arms 70.1 adapted to engage the shroud 13 and adapted to be deflected outwards away from the shroud 13. In FIGS. 40 to 42 the carrier 70 is shown in a rearward position in which the septum 25 of the primary package 24 is spaced from the second tip 17.2 of the needle 17.

A drive spring 30 is arranged to bias the plunger 40 to displace the piston 23 within the primary package 24 to deliver a dose. In an exemplary embodiment, the drive spring 30 is arranged within the plunger 40. A carrier spring 80 is arranged to bias the carrier 70 towards the needle module 18. The carrier spring 80 is rearwardly grounded in the distal region 20 of the housing 11 and forwardly bears against the carrier 70. In an exemplary embodiment, the carrier spring 80 may be arranged laterally from the carrier 70.

The forward arms 70.1 of the carrier 70 comprise a front surface 70.11 adapted to abut a stop 20.5 on the housing 11, e.g. on the distal region 20 thereof, such that the carrier 70 is prevented from moving forward when in the rearward position. Proximal protrusions 70.12 are provided on the forward arms 70.1 adapted to abut a respective transversal beam 13.8 on the shroud 13 when the carrier 70 is in the rearward position thus limiting extension of the shroud 13 from the distal surface 11.1. A lateral stop 13.9 may be provided on each transversal beam 13.8 adapted to laterally abut the proximal protrusion 70.12 preventing outward deflection of the forward arm 70.1 so the front surface 70.11 cannot disengage the stop 20.5. The protrusions 18.3 of the needle module 18 comprise a respective ramp 18.5 adapted to engage the forward arms 70.1 to deflect them outward upon movement of the needle module 18 in the distal direction D to disengage the front surface 70.11 from the stop 20.5.

A noise component 90 may be arranged to provide an audible feedback when the drug has been at least nearly fully expelled from the primary package 24. The noise component 90 may have the form of a rod adapted to be received within the drive spring 30.

A flexible clip 13.10 on the shroud 13 is adapted to abut the needle module 18 to prevent it from moving in the distal direction D when in the retracted position. The abutment may be removed by outwardly deflecting the flexible clip 13.10 to release the needle module 18.

FIGS. 43 to 49 are schematic views of the drug delivery device 10 in different states prior to and during use.

Figure 43:
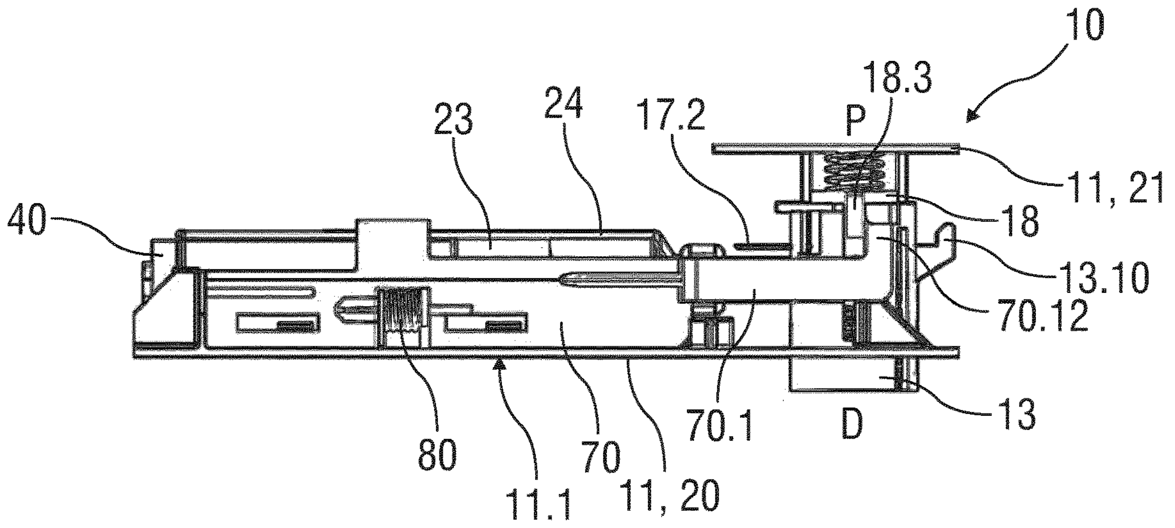
FIG. 43 is a schematic view of the drug delivery device prior to use.

In FIG. 43, the drug delivery device 10 is shown in a state prior to use. The carrier 70 and the shroud 13 are mutually retained so that the shroud 13 is in a retracted position and the carrier 70 is in the rearward position. The needle module 18 is retained in the retracted position by the flexible clip 13.10.

Figure 44:
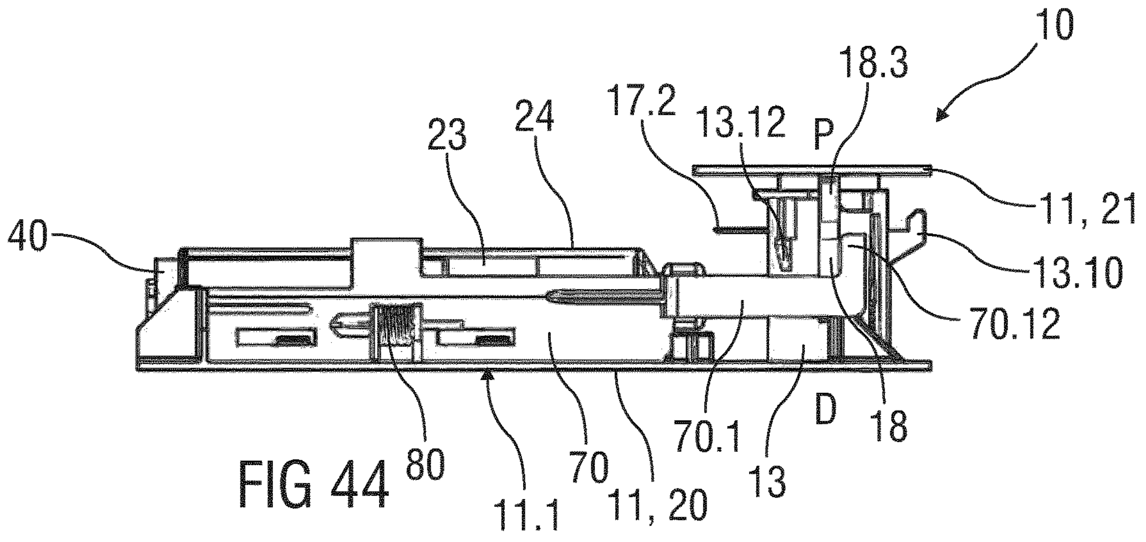
FIG. 44 is a schematic view of the drug delivery device upon depression of the shroud.

In FIG. 44, the shroud 13 is being depressed and moved into a retracted position, i.e. by the distal surface 11.1 being pushed against an injection site. Due to this depression, the lateral stops 13.9 are removed from the proximal protrusions 70.12 on the forward arms 70.1 so the forward arms 70.1 can be deflected outwards. The flexible clip 13.10 may be outwardly deflected, e.g. using a button (not shown), to release the needle module 18. The button may be arranged on the housing 11 such that it only couples with the flexible clip 13.10 when the shroud 13 is in the retracted position such that operation of the button prior to depression of the shroud 13 does not release the needle module 18. If the button was already depressed prior to depression of the shroud 13, a chamfer 13.11 on the flexible clip 13.10 may allow release of the needle module 18 regardless of the sequence of operation of the shroud 13 and button.

Figure 45:
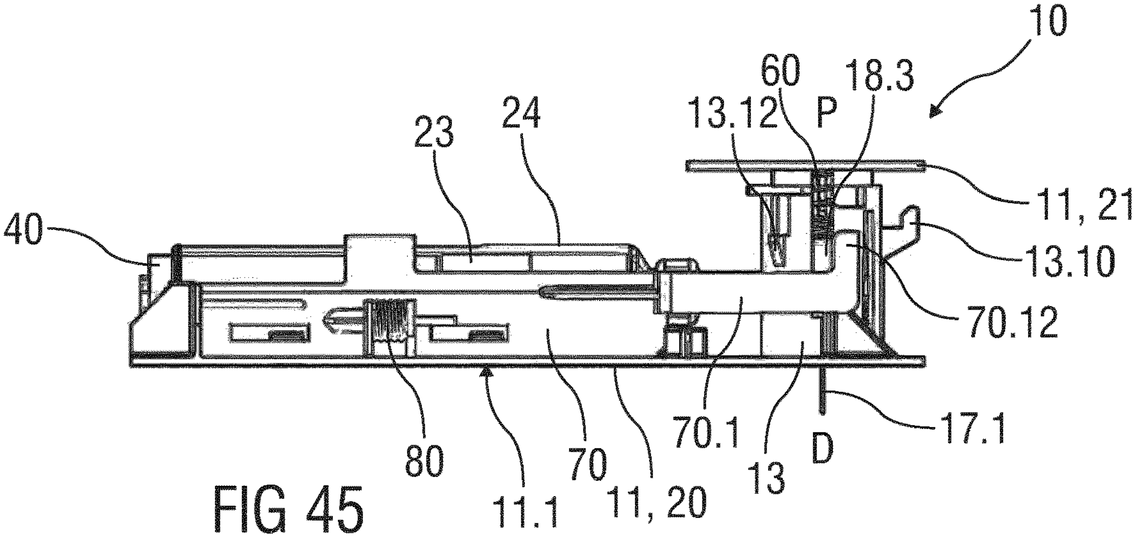
FIG. 45 is a schematic view of the drug delivery device with a needle module in an extended position.

FIG. 45 shows the drug delivery device 10 with the needle module 18 released and advanced in the distal direction D into an extended position driven by the needle spring 60.

The first tip 17.1 of the needle 17 thus extends from the distal surface 11.1. During movement of the needle module 18 in the distal direction D, the ramps 18.5 on the protrusions 18.3 have engaged the forward arms 70.1 and deflected them outward to disengage the front surface 70.11 from the stop 20.5. The carrier 70 is thus no longer prevented from moving forward.

Figure 46:
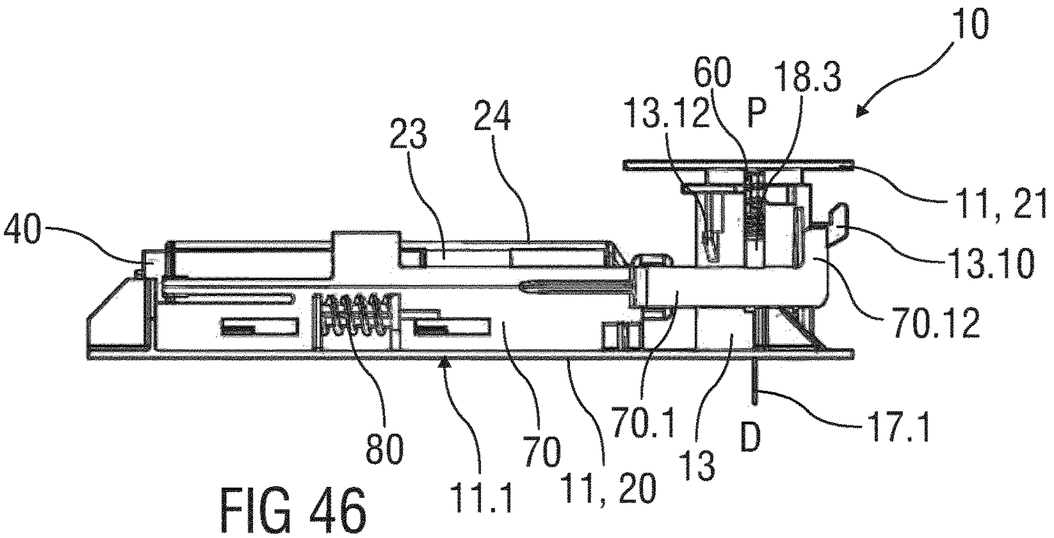
FIG. 46 is a schematic view of the drug delivery device with the carrier having moved forward.

FIG. 46 shows the drug delivery device 10 with the carrier 70 having moved forward driven by the carrier spring 80. The primary package 24 which is fixed to the carrier 70 has also moved forward to such an extent that the second tip 17.2 of the needle 17 pierces the septum 25 establishing a fluid communication between the cavity within the primary package 24 and the needle 17. The plunger 40 may be released as shown above in FIG. 28.

Figure 47:
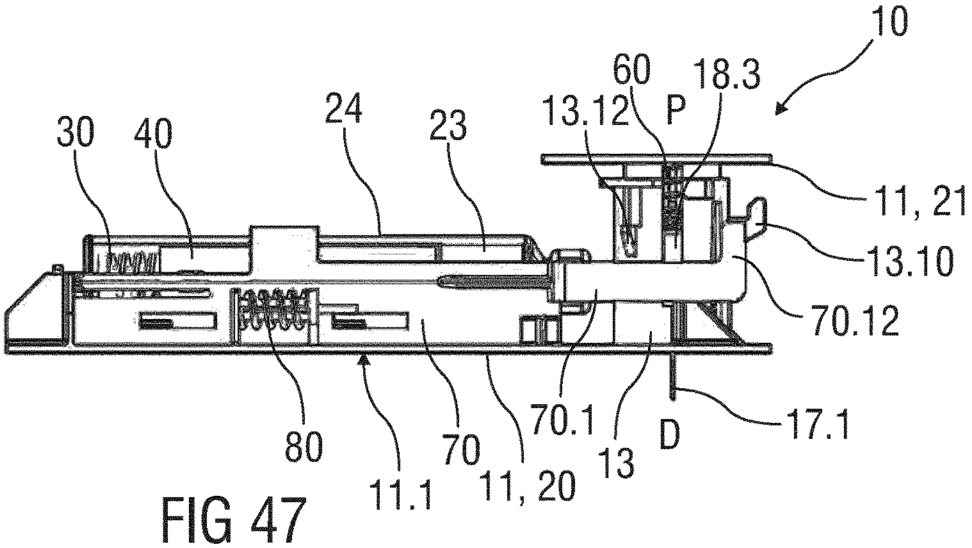
FIG. 47 is a schematic view of the drug delivery device with the plunger being moved forward.

FIG. 47 shows the plunger 40 being advanced in the forward direction. During this movement, the plunger 40, which may have an eye-catching colour, e.g. yellow, may appear in the window **11*a***.

Figure 48:
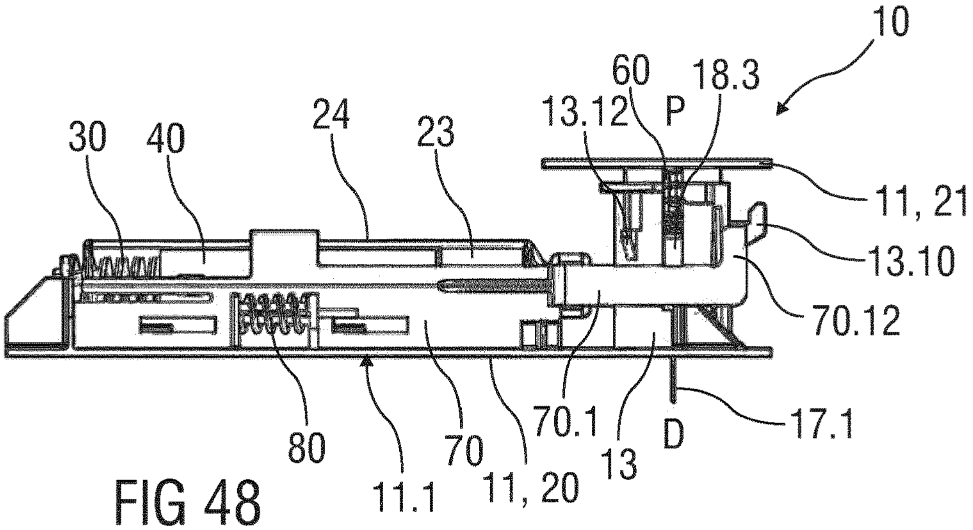
FIG. 48 is a schematic view of the drug delivery device with the plunger having been moved forward.

FIG. 48 shows the plunger 40 having been fully advanced forward to expel the drug. An end of dose noise may be generated as described above and shown in FIG. 32.

Figure 49:
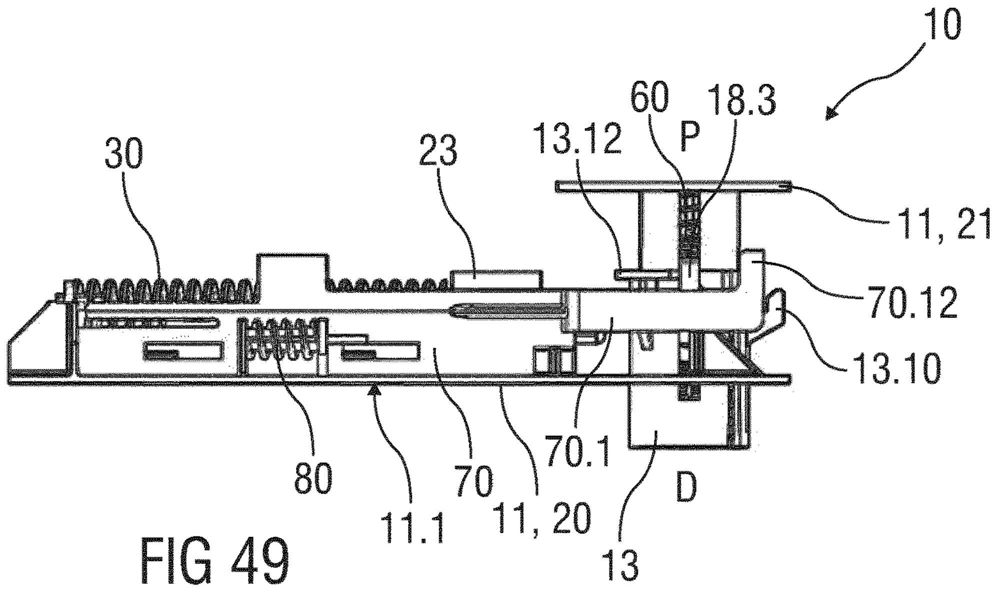
FIG. 49 is a schematic view of the drug delivery device removed from the injection site.

In FIG. 49, the drug delivery device 10 is removed from the injection site. The shroud 13 is moved in the distal direction D driven by the shroud spring 50. In this state, the shroud 13 extends further from the distal surface 11.1 than prior to use due to the proximal protrusions 70.12 on the forward arms 70.1 having been moved forward so they do not interact with the transversal beam 13.8 at this point.

One or more shroud lock clips 13.12 on the shroud 13 engage the housing 11, e.g. the distal region 20 or proximal region 21 thereof, to prevent the shroud 13 from returning in the proximal direction P from this position.

Figure 50:
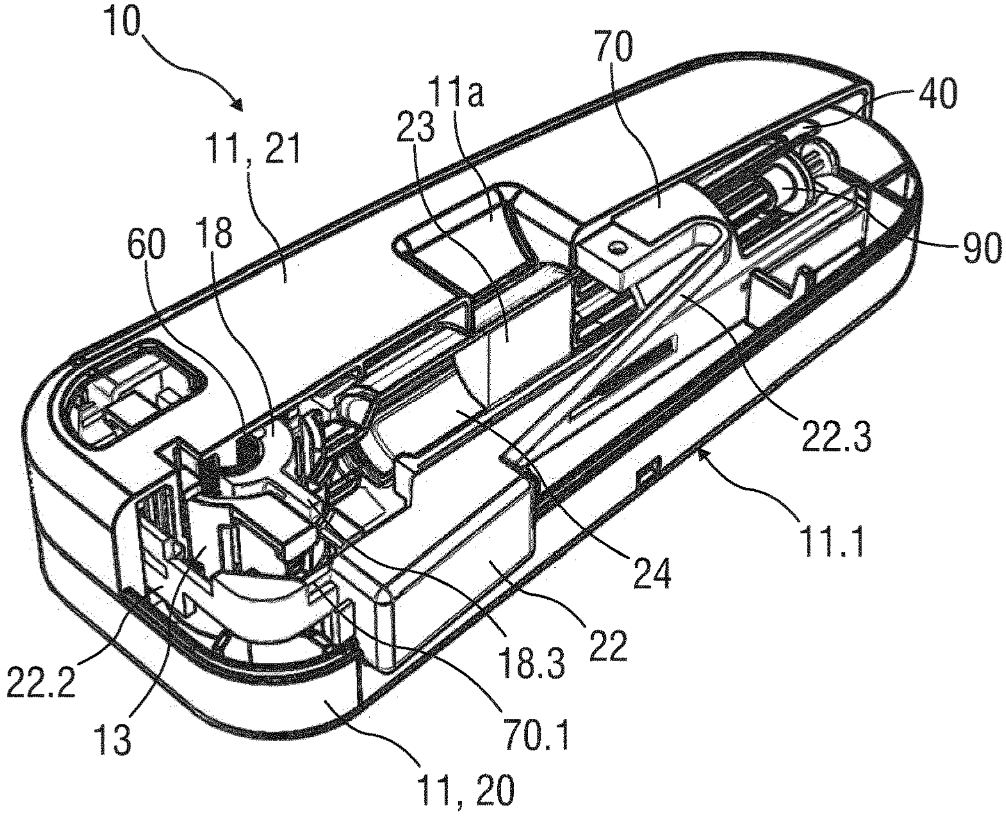
FIG. 50 is a schematic view of another exemplary embodiment of a drug delivery device.
Figure 51:
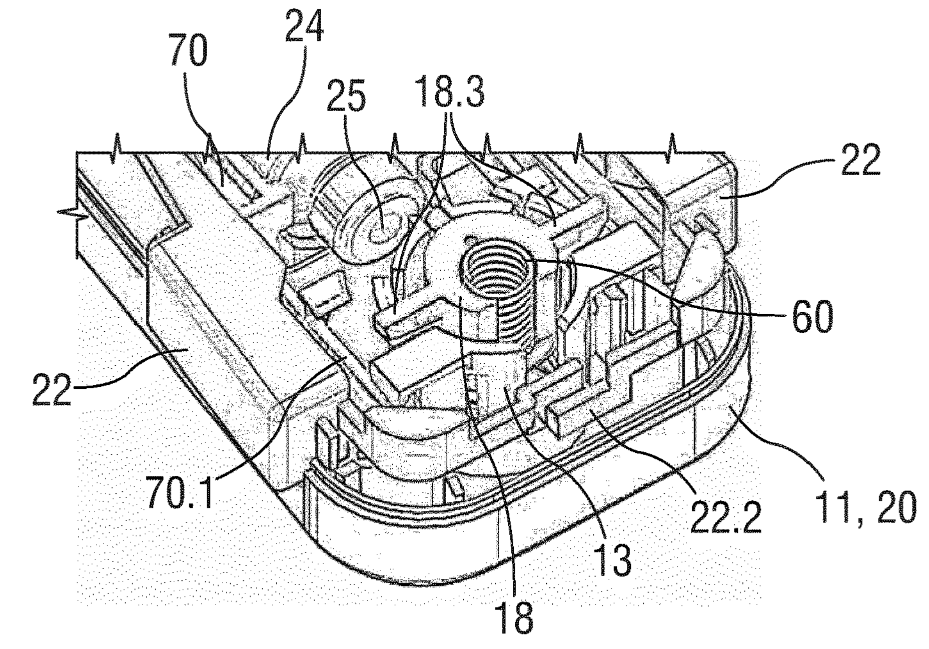
FIG. 51 is a schematic detail view of the drug delivery device.
Figure 52:
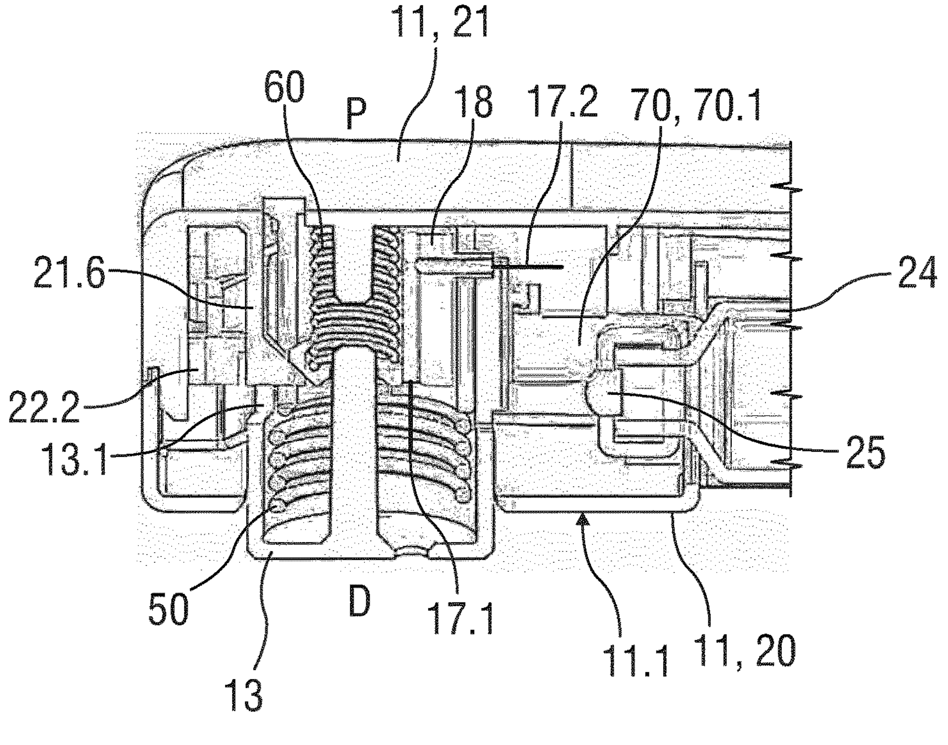
FIG. 52 is a schematic detail view of the drug delivery device.

FIG. 50 is a schematic view of another exemplary embodiment of a drug delivery device 10. FIGS. 51 and 52 are respective detail views. The drug delivery device 10 may be configured essentially like the one shown in FIGS. 40 to 49 but with a different mechanism to retain the needle module 18.

The housing 11 comprises a distal region 20 and a proximal region 21, the distal region 20 having the distal surface 11.1 intended to be placed on the injection site. Mutually complementary snap-lock connectors (not shown) may be provided on the distal region 20 and the proximal region 21 to keep them locked together when assembled.

A shroud spring 50 is arranged to bias the shroud 13 in the distal direction D against the housing 11. A needle spring 60 is arranged to bias the needle module 18 in the distal direction D against the housing 11. The needle module 18 comprises one or more, in particular two, guide protrusions 18.3 adapted to be received in slots of the shroud 13 to keep the second tip 17.2 of the needle 17 oriented towards the primary package 24.

A carrier 70 is arranged within the housing 11 to contain the primary package 24 and to allow movement thereof essentially in parallel with the distal surface 11.1 towards the needle module 18. Movement of the primary package 24 towards the needle module 18 may be achieved either by moving the primary package 24 within the carrier 70 or by moving the carrier 70 with the contained primary package 24.

The carrier 70 may comprise one or two resilient forward arms 70.1 adapted to engage the shroud 13 and adapted to be deflected outwards away from the shroud 13. The carrier 70 is shown in a rearward position in which the septum of the primary package 24 is spaced from the second tip of the needle 17.

A drive spring (not shown) is arranged to bias the plunger 40 to displace the piston 23 within the primary package 24 to deliver a dose. In an exemplary embodiment, the drive spring is arranged within the plunger 40. A carrier spring (not shown) is arranged to bias the carrier 70 towards the needle module 18. The carrier spring is rearwardly grounded in the housing 11 and forwardly bears against the carrier 70. In an exemplary embodiment, the carrier spring may be arranged laterally from the carrier 70.

A noise component 90 may be arranged to provide an audible feedback when the drug has been at least nearly fully expelled from the primary package 24. The noise component 90 may have the form of a rod adapted to be received within the drive spring 30.

One or two buttons 22 may be provided, in particular laterally on the housing 11 to release the needle module 18 upon operation. A spring element 22.3 may be provided to bias the buttons 22 to extend from the housing 11.

Figure 52A:
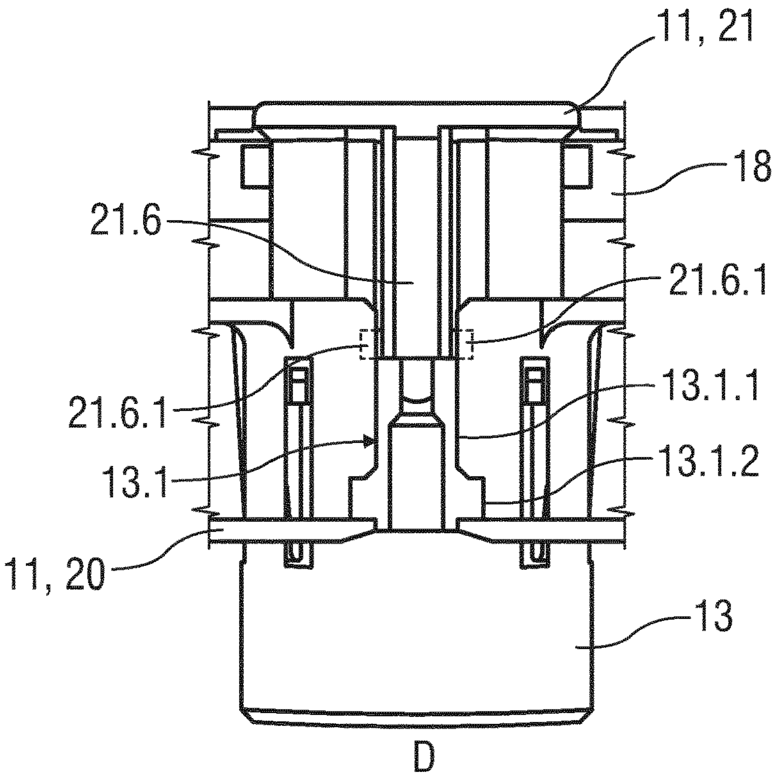
FIG. 52A is a schematic detail view of the drug delivery device.
Figure 52B:
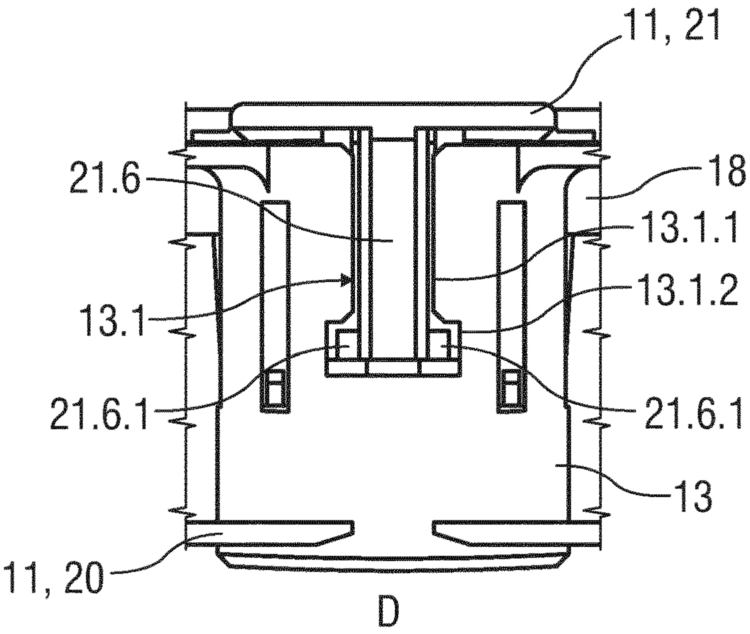
FIG. 52B is a schematic detail view of the drug delivery device.
Figure 52C:
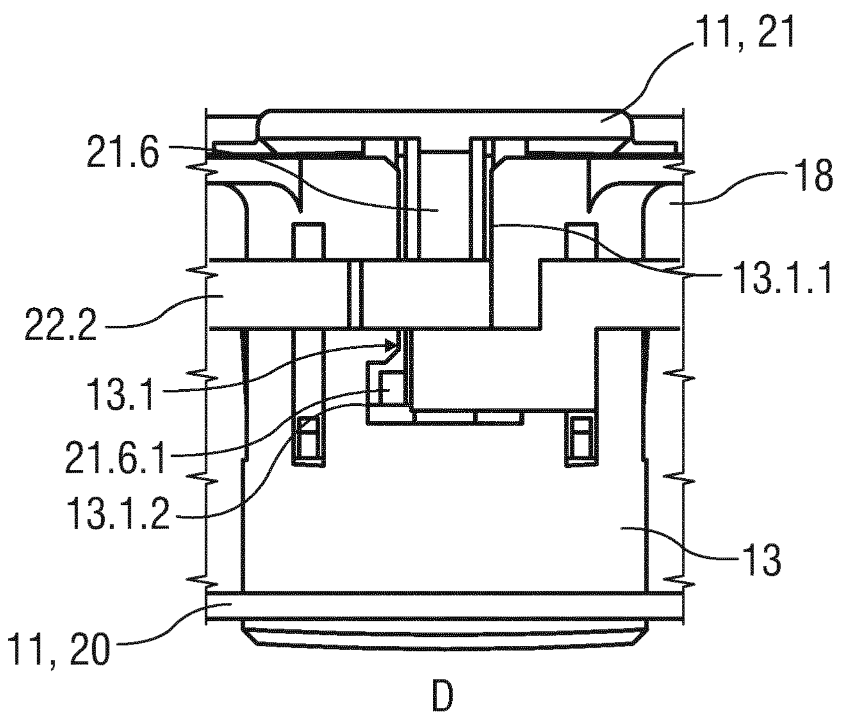
FIG. 52C is a schematic detail view of the drug delivery device.
Figure 52D:
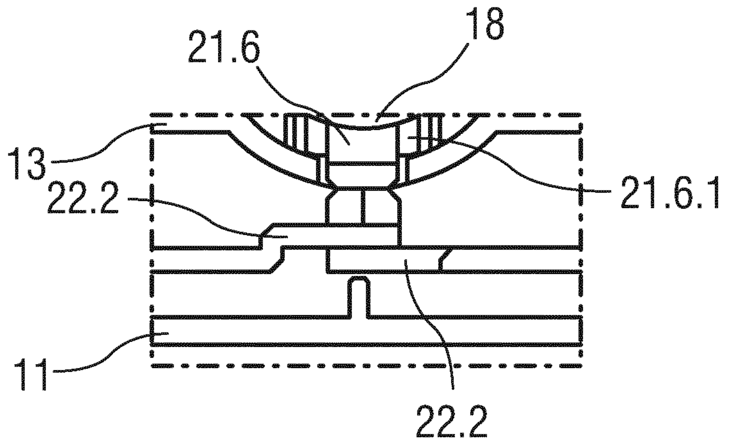
FIG. 52D is a schematic detail view of the drug delivery device.

The needle module 18 is held in a retracted position by a needle retainer clip 21.6 protruding from the proximal region 21 of the housing 11 within the housing 11 in the distal direction D through a slot 13.1 in the shroud 13, the needle retainer clip 21.6 and/or the needle module 18 having one or more ramps adapted to outwardly deflect the needle retainer clip 21.6 under a force from the needle spring 60 to disengage the needle module 18 from the needle retainer clip 21.6 to allow the needle module 18 to move in the distal direction D into an extended position in which the first tip 17.1 of the needle 17 extends beyond the distal surface 11.1. Each of the buttons 22 comprises a transversal beam 22.2, one or both of them adapted to outwardly support the needle retainer clip 21.6 when the buttons 22 are not depressed such that the needle retainer clip 21.6 cannot be outwardly deflected to release the needle module 18. Depression of the buttons 22 removes the outward support from the needle retainer clip 21.6 such that the needle module 18 may be released to move into the extended position. FIG. 52A is another detail view of the drug delivery device 10 wherein the buttons 22 are not shown for clarity. It can be seen that the slot 13.1 is T-shaped having a longitudinal portion 13.1.1 and a transversal portion 13.1.2 being wider than the longitudinal portion 13.1.1 and located at the distal end thereof. The needle retainer clip 21.6 comprises at least one stepped surface 21.6.1 on its distal end running along an inner diameter face of the shroud 13. The stepped surface 21.6.1 may be inwardly offset relative to the rest of the needle retainer clip 21.6. The stepped surface 21.6.1 matches the transversal portion 13.1.2 of the slot 13.1 when the shroud 13 is at least almost fully depressed or fully depressed as shown in FIG. 52B. Prior to full or almost full depression of the shroud 13, the stepped surface 21.6.1 is not aligned with the transversal portion 13.1.2 but located within the longitudinal portion 13.1.1 such that the stepped surface 21.6.1 abuts the inner diameter face of the shroud 13 preventing the retainer clip 21.6 from being deflected outwards thus also preventing release of the needle module 18. FIGS. 52C and 52D are further detail views corresponding to FIG. 52B but also showing the buttons 22. It can be seen that even if the shroud 13 is fully depressed allowing the stepped surface 21.6.1 to pass through the transversal portion 13.1.2 of the slot 13.1 the transversal beams 22.2 of the buttons 22 still prevent outward deflection of the retainer clip 21.6. In another embodiment, the transversal portion 13.1.2 may not be located at the distal end of the longitudinal slot 13.1 but somewhere between the proximal and distal ends thereof and the stepped surface 21.6.1 may be accordingly positioned to match the transversal portion 13.1.2 upon full or almost full depression of the shroud 13.

Figure 53:
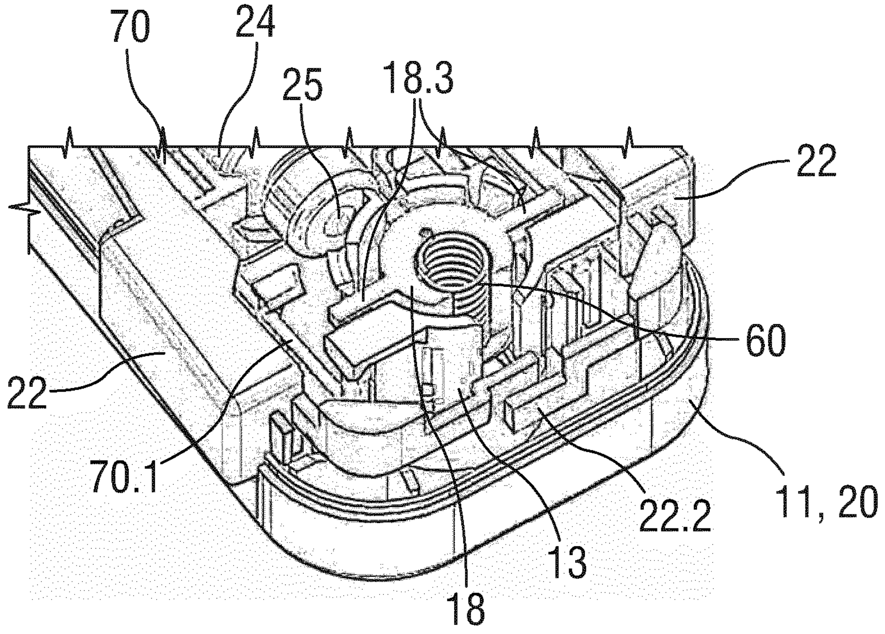
FIG. 53 is a schematic detail view of the drug delivery device with the shroud being depressed.
Figure 54:
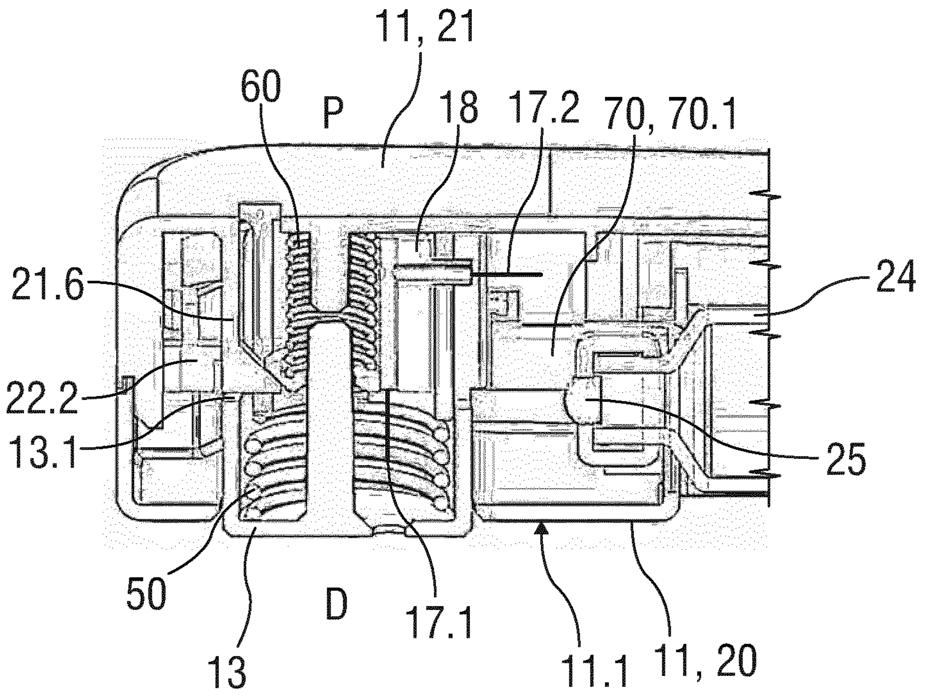
FIG. 54 is a schematic detail view of the drug delivery device with the shroud being depressed.

In FIGS. 53 and 54, the shroud 13 is being depressed and moved into the retracted position, i.e. by the distal surface 11.1 being pushed against an injection site. The shroud 13 and buttons 22 can be depressed in any order to release the needle module 18. As the shroud 13 is depressed and moved in the proximal direction P it aligns the stepped surface 21.6.1 with the transversal portion 13.1.2 allowing the stepped surface 21.6.1 to pass through the transversal portion 13.1.2. The buttons 22 can then be depressed to release the needle module 18 to move into the extended position in which the first tip 17.1 of the needle 17 extends beyond the distal surface 11.1. It is also possible to depress the buttons 22 first and then to depress the shroud 13 to release the needle module 18. Subsequently, the drug delivery device 10 may behave as the one shown in FIGS. 40 to 49.

Figure 55:
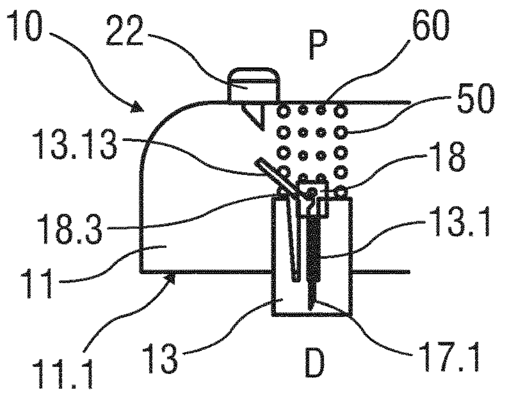
FIG. 55 is a schematic detail view of an exemplary embodiment of a drug delivery device.

FIG. 55 is a schematic view of another exemplary embodiment of a needle retaining mechanism for a drug delivery device 10 configured essentially like the one shown in FIG. 2 or one of the other embodiments described herein.

A shroud spring 50 is arranged to bias the shroud 13 in the distal direction D against the housing 11 or against the needle module 18. A needle spring 60 is arranged to bias the needle module 18 in the distal direction D against the housing 11. The needle module 18 comprises one or more, in particular two, guide protrusions 18.3 adapted to be received in slots 13.1 of the shroud 13. A resilient catch arm 13.13 may be arranged on the shroud 13 to block access of the slot 13.1 so that the guide protrusion 18.3 cannot enter the slot 13.1 and the needle module 18 is prevented from advancing in the distal direction D. The catch arm 13.13 is adapted to be deflected to allow the protrusion 18.3 to access the slot 13.1. A button 22 is arranged on the housing 11 to engage the catch arm 13.13 when the shroud 13 is moved into a retracted position, e.g. by the distal surface 11.1 being pushed against an injection site. If the button 22 is depressed when the shroud 13 is in the retracted position, the catch arm 13.13 is deflected and unblocks access of the protrusion 18.13 into the slot 13.1.

In FIG. 55, the shroud 13 is in the extended position; the catch arm 13.13 is relaxed and blocks access to the slot 13.1. The button 22 is not depressed and spaced from the catch arm 13.13.

Figure 56:
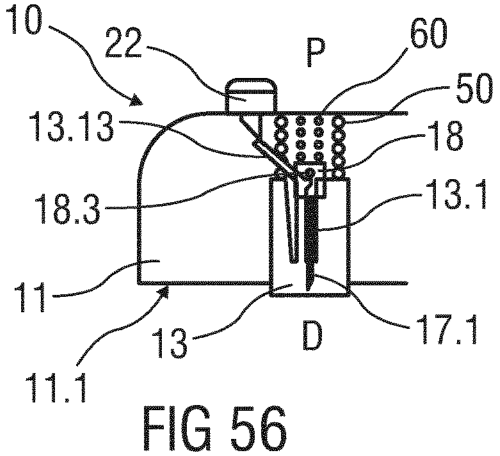
FIG. 56 is a schematic detail view of the drug delivery device with the shroud moved into the retracted position.

In FIG. 56, the shroud 13 is moved in the proximal direction P into the retracted position against the bias of the shroud spring 50. As the guide protrusion 18.3 abuts the catch arm 13.13, the needle module 18 is also moved in the proximal direction P thus pre-loading the needle spring 60. The catch arm 13.13 has been moved to abut or almost abut the button 22.

If the drug delivery device 10 is removed from the injection site at this point, the shroud 13 and all the other components will return to the position as shown in FIG. 55.

Figure 57:
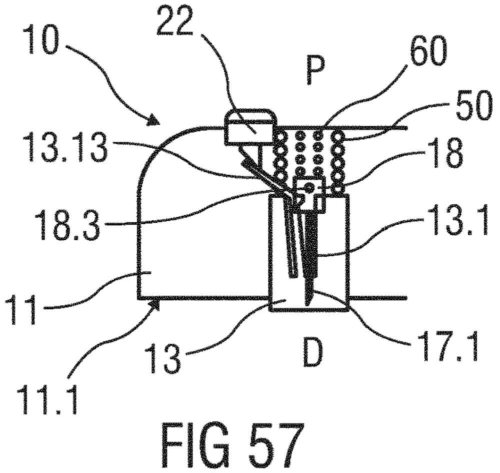
FIG. 57 is a schematic detail view of the drug delivery device with a button depressed.

If the button 22 is depressed in the state as shown in FIG. 56, the button 22 laterally deflects the catch arm 13.13 so that the catch arm 13.13 unblocks access of the protrusion 18.13 into the slot 13.1 as shown in FIG. 57.

Figure 58:
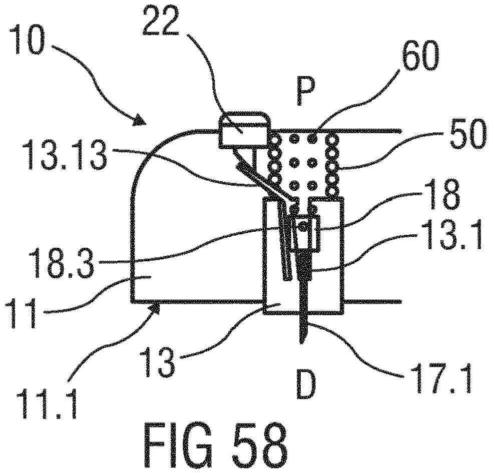
FIG. 58 is a schematic detail view of the drug delivery device with a needle module in an extended position.

The protrusion 18.13 enters the slot 13.1 and the needle module 18 moves in the distal direction D driven by the needle spring 60 so that the first tip 17.1 of the needle 17 extends beyond the distal surface 11.1 as shown in FIG. 58.

Figure 59:
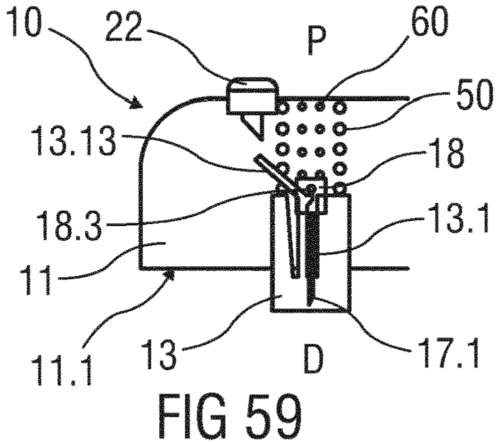
FIG. 59 is a schematic detail view of the drug delivery device removed from the injection site.

As the drug delivery device 10 is removed from the injection site as shown in FIG. 59, the shroud 13 returns in the distal direction D driven by the shroud spring 50 while the needle module 18 remains in position, e.g. due to distally abutting on the housing 11. The first tip 17.1 of the needle 17 is thus again covered within the shroud 13, the catch arm 13.13 disengages the button 22 so that the catch arm 13.13 can relax. The protrusion 18.3 travels up the slot 13.1 briefly deflecting the catch arm 13.13 which then again relaxes and blocks access of the protrusion 18.3 to the slot 13.1. The shroud 13 can be locked in this position by other means, e.g. as shown in one of the other embodiments described herein or by motion of the primary package 24 or the carrier 70.

In this embodiment, the needle spring 60 can initially be relaxed or only slightly charged. The needle spring 60 is charged by depression of the shroud 13 into the retracted position.

Figure 60:
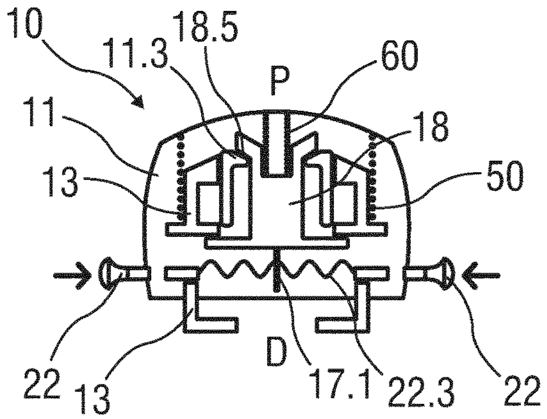
FIG. 60 is a schematic detail view of an exemplary embodiment of a drug delivery device.

FIG. 60 is a schematic view of another exemplary embodiment of a needle retaining mechanism for a drug delivery device 10 configured essentially like the one shown in FIG. 2 or one of the other embodiments described herein.

A shroud spring 50 is arranged to bias the shroud 13 in the distal direction D against the housing 11 or against the needle module 18. A pre-loaded needle spring 60 is arranged to bias the needle module 18 in the distal direction D against the housing 11. The needle module 18 comprises one or more, in particular two, ramps 18.5 adapted to engage respective resilient clips 11.3 on the housing 11. The resilient clips 11.3 are outwardly supported by the shroud 13 when the shroud 13 is in an extended position so that the resilient clips 11.3 cannot deflect. This prevents the needle module 18 from moving in the distal direction D.

One or two laterally arranged buttons 22 are interlocked with the shroud 13 preventing the shroud 13 from moving in the proximal direction P from the extended position prior to depression of the buttons 22. One or more spring elements 22.3 may be provided to bias the buttons 22 to extend from the housing 11.

Figure 61:
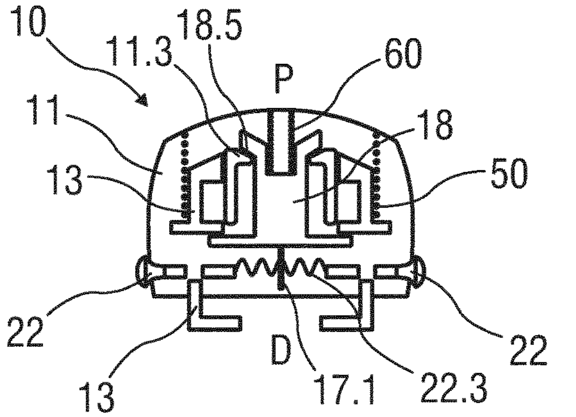
FIG. 61 is a schematic detail view of the drug delivery device with the shroud depressed.

FIG. 61 shows the drug delivery device 10 with the buttons 22 depressed removing the interlock of the buttons 22 with the shroud 13. If the buttons 22 are released in this state they will return into their position extending from the housing 11 as in FIG. 60.

Figure 62:
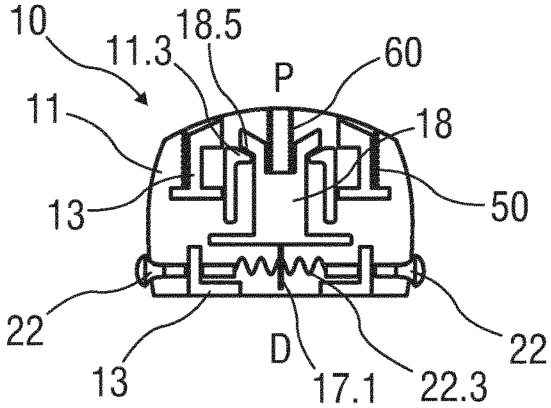
FIG. 62 is a schematic detail view of the drug delivery device with the shroud depressed.

If, in the position of FIG. 61, the shroud 13 is depressed in the proximal direction P, e.g. by pushing the distal surface 11.1 against an injection site, the outward support of the resilient clips 11.3 by the shroud 13 is removed as shown in FIG. 62.

Figure 63:
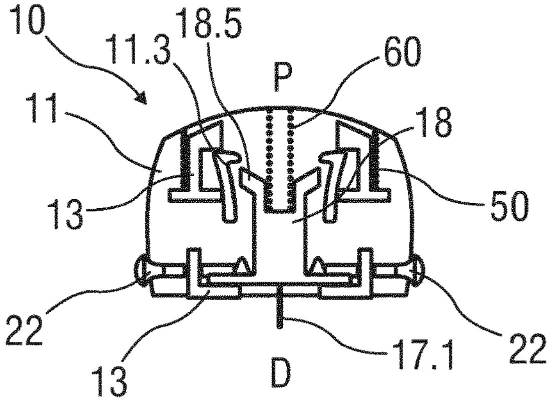
FIG. 63 is a schematic detail view of the drug delivery device with the needle module in the extended position.

The ramps 18.5 will thus outwardly deflect the resilient clips 11.3 under force from the needle spring 60 so the ramps 18.5 disengage the resilient clips 11.3 allowing the needle module 18 to move in the distal direction D into an extended position so that the first tip 17.1 of the needle 17 extends beyond the distal surface 11.1 as shown in FIG. 63.

Figure 64:
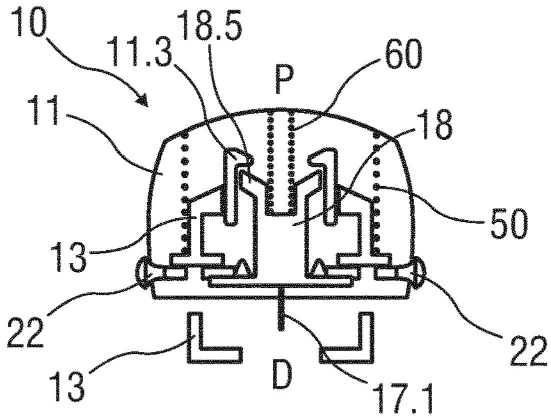
FIG. 64 is a schematic detail view of the drug delivery device removed from the injection site.

As the drug delivery device 10 is removed from the injection site, the shroud 13 returns in the distal direction D driven by the shroud spring 50 while the needle module 18 remains in position, e.g. due to distally abutting on the housing 11 as shown in FIG. 64. The first tip 17.1 of the needle 17 is thus again covered within the shroud 13. The shroud 13 can be locked in this position by other means, e.g. as shown in one of the other embodiments described herein or by motion of the primary package 24 or the carrier 70.

Figure 65:
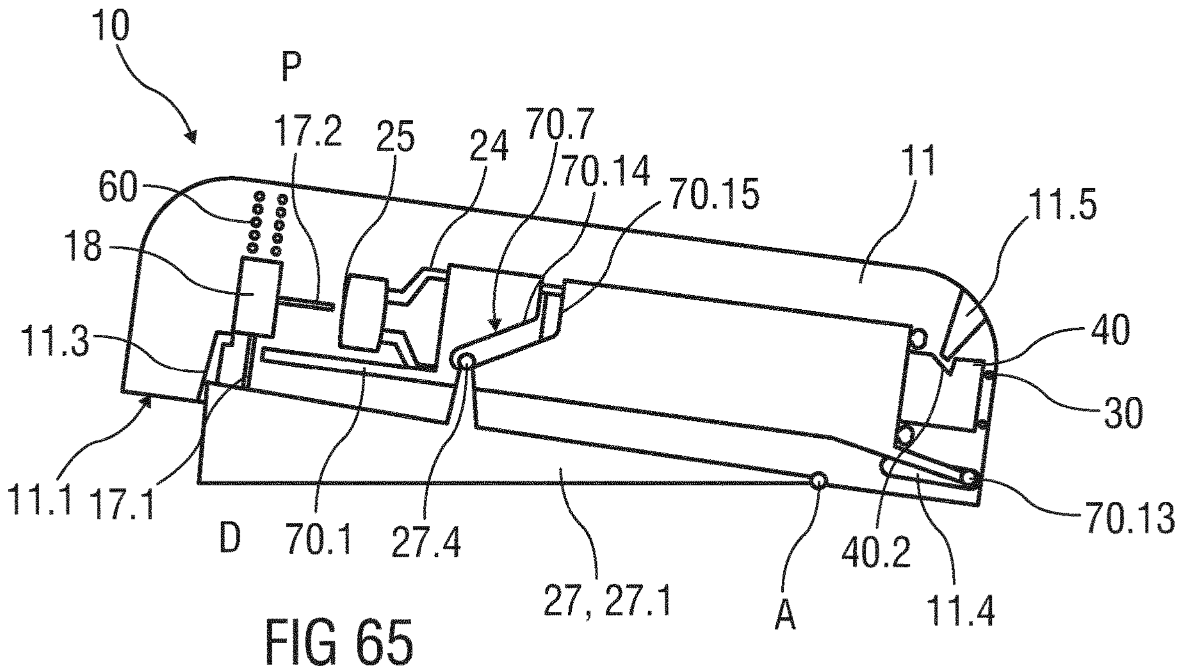
FIG. 65 is a schematic view of an exemplary embodiment of a drug delivery device.

FIG. 65 is a schematic view of another exemplary embodiment of a drug delivery device 10 configured essentially like the one shown in FIG. 2 or one of the other embodiments described herein.

The drug delivery device 10 comprises a housing 11. The primary package 24 is retained within a carrier 70 which is slidable with in the housing 11 essentially in parallel with the distal surface 11.1 and pivotable at a rear end of the carrier 70 within the housing 11. This may be achieved by an axle 70.13 of the carrier 70 engaging in one or more slot holes 11.4 in the housing 11.

A drive spring 30 is arranged to bias the plunger 40 to displace the piston 23 within the primary package 24 to deliver a dose. In an exemplary embodiment, the drive spring 30 is arranged within the plunger 40.

A body contact sensor 27 is pivoted about an axis A in the housing 11, e.g. a transversal axis, such that a contact part 27.1 of the body contact sensor 27 may extend from the distal surface 11.1 and pivot about the axis A to be depressed into the housing 11 behind or flush with the distal surface 11.1. The body contact sensor 27 may be configured as a shroud 13 for covering an extended needle 17. A needle module 18 having a needle 17 with a first tip 17.1 and a second tip 17.2 is provided, the first tip 17.1 adapted to be extended from the distal surface 11.1 and the second tip adapted to point towards the primary package 24 to pierce a septum 25 thereof. The needle module 18 is movable between a retracted position with the first tip 17.1 hidden behind the distal surface 11.1 and an extended position in which the first tip 17.1 protrudes from the distal surface 11.1. A needle spring 60 is arranged to bias the needle module 18 in the distal direction D.

The carrier 70 comprises a guide channel 70.7 and the body contact sensor 27 comprises a cam follower 27.4 adapted to be received and guided within the guide channel 70.7. The guide channel 70.7 may comprise a an inclined section 70.14 generally pointing in the rearward direction and the proximal direction P at an angle relative to the distal surface 11.1, the inclined section 70.14 adapted to engage the cam follower 27.4 when the contact part 27.1 of the body contact sensor 27 extends from the distal surface 11.1. The cam follower 27.4 is adapted to move up the inclined section 70.14 upon depression of the contact part 27.1 until reaching a proximal section 70.15 of the guide channel 70.7 directed essentially in the proximal direction P.

A resilient clip 11.3 is disposed on the housing 11 so as to abut the needle module 18 when the needle module 18 is in the retracted position preventing movement of the needle module 18 in the distal direction D. The carrier 70 may comprise one or two resilient forward arms 70.1 adapted to engage the resilient clip 11.3 to deflect it away from the needle module 18 to release the needle module 18 allowing it to move in the distal direction D.

A locking pin 11.5 is arranged in the housing 11 adapted to engage in an aperture 40.2 in the plunger 40 preventing the plunger 40 from advancing forward.

In FIG. 65 the carrier 70 is shown in a rearward position in which the septum 25 of the primary package 24 is spaced from the second tip 17.2 of the needle 17 and the forward arm 70.1 is spaced from the resilient clip 11.3. The aperture 40.2 in the plunger 40 is engaged by the locking pin 11.5. The contact part 27.1 extends from the housing 11. The needle module 18 is in the retracted position.

Figure 66:
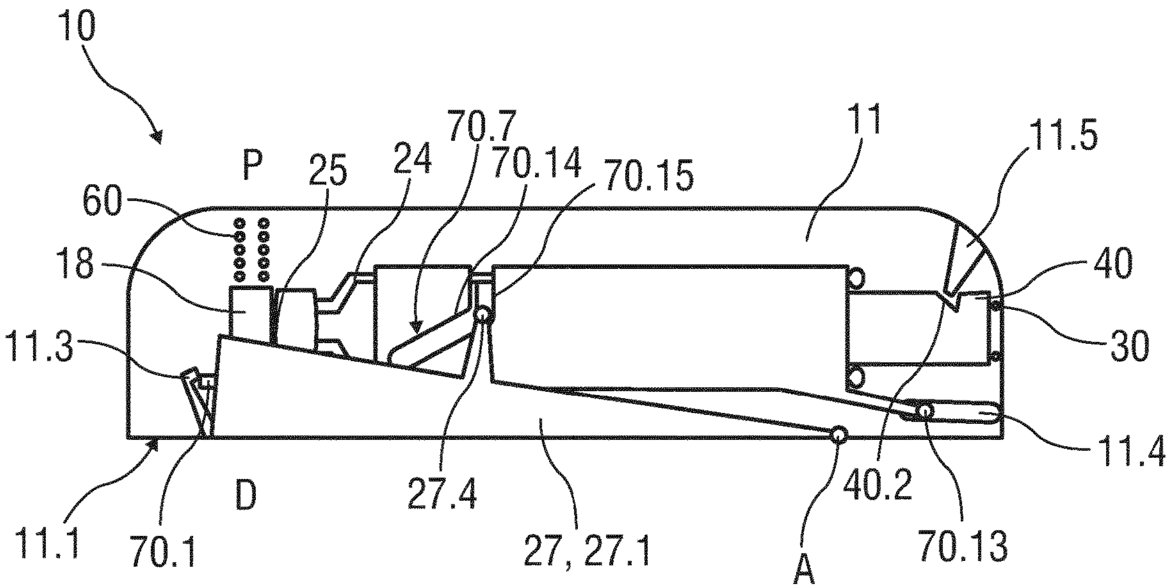
FIG. 66 is a schematic view of the drug delivery device with a contact part of a body contact sensor depressed.

In FIG. 66, the contact part 27.1 of the of the body contact sensor 27 is depressed in the proximal direction P into the housing 11, e.g. by pushing the distal surface 11.1 against an injection site. This causes the cam follower 27.4 to travel up the inclined section 70.14 of the guide channel 70.7 forcing the carrier 70 and the primary package 24 forwards facilitated by the slot hole 11.4. Due to the movement of the carrier 70, the second tip 17.2 pierces the septum 25. As the cam follower 27.4 arrives at the proximal section 70.15 of the guide slot 70.7, forward movement of the carrier 70 ends.

Figure 67:
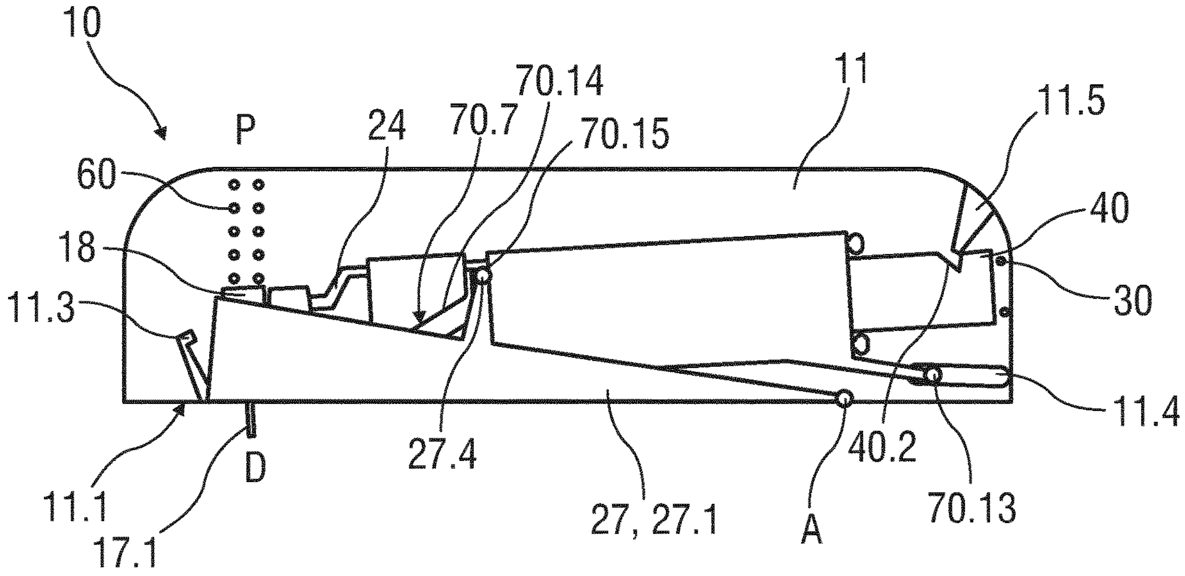
FIG. 67 is a schematic view of the drug delivery device with the carrier moved forward.

FIG. 67 shows that due to the forward movement of the carrier 70, the forward arm 70.1 deflects the resilient clip 11.3 out of abutment with the needle module 18 which is thus released and moved in the distal direction D by the needle spring 60 such that the first tip 17.1 extends from the distal surface 11.1. Movement of the needle module 18 tilts the primary package 24 and the carrier 70 about the axle 70.13 facilitated by the cam follower 27.4 moving up the proximal section 70.15. As the plunger 40 is guided within the primary package 24, the plunger is also tilted thus disengaging the locking pin 11.5 from the aperture 40.2 to release the plunger 40.

Figure 68:
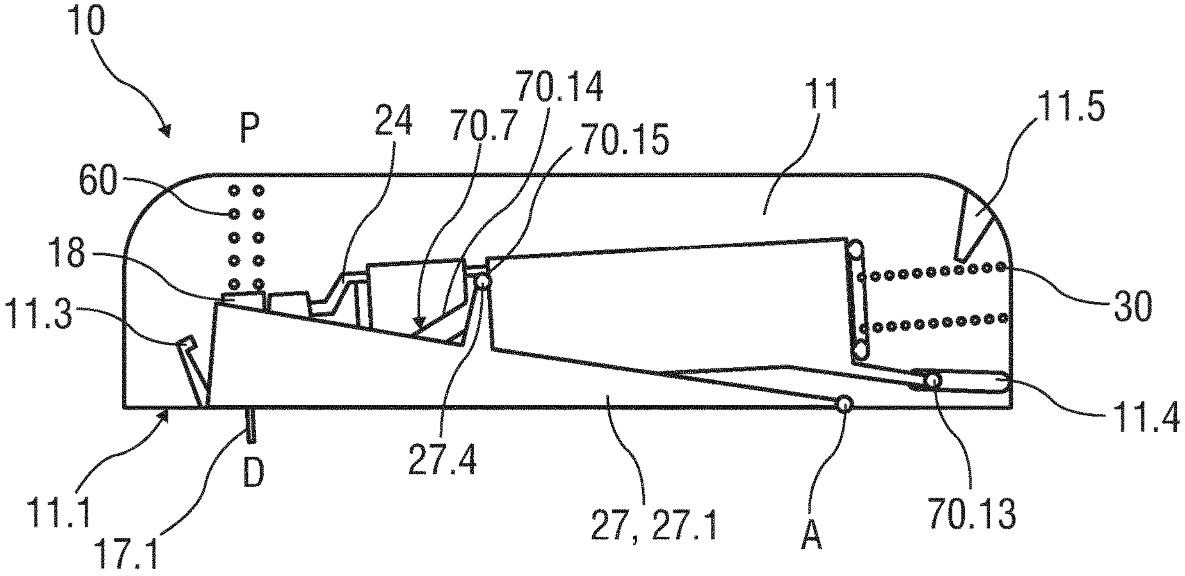
FIG. 68 is a schematic view of the drug delivery device with the plunger advanced.

FIG. 68 shows that, subsequently, the plunger 40 is advanced forward by the drive spring 30 to dispense the dose. A spring element (not shown) may be provided to re-extend the body contact sensor 27 upon removal of the drug delivery device 10 from the injection site to prevent access to the extended first tip 17.1 of the needle 17. The body contact sensor 27 can be locked in this position, e.g. as shown in one of the other embodiments described herein for locking the shroud.

The terms "drug" or "medicament" are used herein to describe one or more pharmaceutically active compounds. As described below, a drug or medicament can include at least one small or large molecule, or combinations thereof, in various types of formulations, for the treatment of one or more diseases. Exemplary pharmaceutically active compounds may include small molecules; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more of these drugs are also contemplated.

The term "drug delivery device" shall encompass any type of device or system configured to dispense a drug into a human or animal body. Without limitation, a drug delivery device may be an injection device (e.g., syringe, pen injector, auto injector, large-volume device, pump, perfusion system, or other device configured for intraocular, subcutaneous, intramuscular, or intravascular delivery), skin patch (e.g., osmotic, chemical, micro-needle), inhaler (e.g., nasal or pulmonary), implantable (e.g., coated stent, capsule), or feeding systems for the gastro-intestinal tract. The presently described drugs may be particularly useful with injection devices that include a needle, e.g., a small gauge needle.

The drug or medicament may be contained in a primary package or "drug container" adapted for use with a drug delivery device. The drug container may be, e.g., a cartridge, syringe, reservoir, or other vessel configured to provide a suitable chamber for storage (e.g., short- or long-term storage) of one or more pharmaceutically active compounds. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of a drug formulation (e.g., a drug and a diluent, or two different types of drugs) separately, one in each chamber. In such instances, the two chambers of the dual-chamber cartridge may be configured to allow mixing between the two or more components of the drug or medicament prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drug delivery devices and drugs described herein can be used for the treatment and/or prophylaxis of many different types of disorders. Exemplary disorders include, e.g., diabetes mellitus or complications associated with diabetes mellitus such as diabetic retinopathy, thromboembolism disorders such as deep vein or pulmonary thromboembolism. Further exemplary disorders are acute coronary syndrome (ACS), angina, myocardial infarction, cancer, macular degeneration, inflammation, hay fever, atherosclerosis and/or rheumatoid arthritis.

Exemplary drugs for the treatment and/or prophylaxis of diabetes mellitus or complications associated with diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4

(DPP4) inhibitor, or a pharmaceutically acceptable salt or solvate thereof, or any mixture thereof. As used herein, the term "derivative" refers to any substance which is sufficiently structurally similar to the original substance so as to have substantially similar functionality or activity (e.g., therapeutic effectiveness).

Exemplary insulin analogues are Gly(A21), Arg(B31), Arg(B32) human insulin(insulin glargine); Lys(B3), Glu (B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Exemplary insulin derivatives are, for example, B29-N-myristoyl-des(B30) human insulin; B29-N-palmitoyl-des (B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin; B29-N—(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin. Exemplary GLP-1, GLP-1 analogues and GLP-1 receptor agonists are, for example: Lixisenatide/AVE0010/ZP10/Lyxumia, Exenatide/Exendin-4/Byetta/Bydureon/ITCA 650/AC-2993 (a 39 amino acid peptide which is produced by the salivary glands of the Gila monster), Liraglutide/Victoza, Semaglutide, Taspoglutide, Syncria/Albiglutide, Dulaglutide, rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091 March-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An exemplary oligonucleotide is, for example: mipomersen/Kynamro, a cholesterol-reducing antisense therapeutic for the treatment of familial hypercholesterolemia.

Exemplary DPP4 inhibitors are Vildagliptin, Sitagliptin, Denagliptin, Saxagliptin, Berberine.

Exemplary hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Exemplary polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20/Synvisc, a sodium hyaluronate.

The term "antibody", as used herein, refers to an immunoglobulin molecule or an antigen-binding portion thereof. Examples of antigen-binding portions of immunoglobulin molecules include F(ab) and $F(ab')_2$ fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region.

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, $F(ab')_2$ fragments, scFv (single-chain Fv) fragments, linear antibodies, monospecific or multispecific antibody fragments such as bispecific, trispecific, and multispecific antibodies (e.g., diabodies, triabodies, tetrabodies), minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Exemplary antibodies are anti PCSK-9 mAb (e.g., Alirocumab), anti IL-6 mAb (e.g., Sarilumab), and anti IL-4 mAb (e.g., Dupilumab).

The compounds described herein may be used in pharmaceutical formulations comprising (a) the compound(s) or pharmaceutically acceptable salts thereof, and (b) a pharmaceutically acceptable carrier. The compounds may also be used in pharmaceutical formulations that include one or more other active pharmaceutical ingredients or in pharmaceutical formulations in which the present compound or a pharmaceutically acceptable salt thereof is the only active ingredient. Accordingly, the pharmaceutical formulations of the present disclosure encompass any formulation made by admixing a compound described herein and a pharmaceutically acceptable carrier.

Pharmaceutically acceptable salts of any drug described herein are also contemplated for use in drug delivery devices. Pharmaceutically acceptable salts are for example acid addition salts and basic salts. Acid addition salts are e.g. HCl or HBr salts. Basic salts are e.g. salts having a cation selected from an alkali or alkaline earth metal, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are known to those of skill in the arts.

Pharmaceutically acceptable solvates are for example hydrates or alkanolates such as methanolates or ethanolates.

Those of skill in the art will understand that modifications (additions and/or removals) of various components of the substances, formulations, apparatuses, methods, systems and embodiments described herein may be made without departing from the full scope and spirit of the present disclosure, which encompass such modifications and any and all equivalents thereof.

Further embodiments are described in the following:

Embodiment 1. A drug delivery device (10), comprising a housing (11) adapted to receive a primary package (24), the housing (11) comprising a distal surface (11.1) adapted to be placed against an injection site and a proximal surface (11.2) opposite the distal surface (11.1), the proximal surface (11.2) adapted to be held in the palm of a user's hand during drug delivery, the housing (11) having a flat form-factor in such a manner that a first extension of the housing (11) between the distal surface (11.1) and the proximal surface (11.2) is less than at least one extension at right angles to the first extension.

Embodiment 2. The drug delivery device (10) of embodiment 1, comprising an injection needle (17) configured to be connected or connectable to a primary package (24) received within the housing (11), wherein the needle (17) comprises a first tip (17.1) automatically movable between a retracted position hidden within the housing (11) and an extended position extending through the distal surface (11.1).

Embodiment 3. The drug delivery device (10) of embodiment 1 or 2, wherein a mounting axis of the primary package (24) is essentially at right angles with respect to the first extension.

Embodiment 4. The drug delivery device (10) of any one of the preceding embodiments, wherein the distal surface (11.1) is non-adhesive.

Embodiment 5. The drug delivery device (10) according to any one of the preceding embodiments, wherein the distal surface (11.1) is rigid.

Embodiment 6. The drug delivery device (10) according to any one of the preceding embodiments, wherein the housing (11) comprises at least one window (11*a*) through which the primary package (24) can be monitored.

Embodiment 7. The drug delivery device (10) of embodiment 6, wherein the window (11*a*) is arranged in the proximal surface (11.2) and/or in a lateral surface of the housing (11).

Embodiment 8. The drug delivery device (10) according to any one of embodiments 2 to 7, wherein the needle (17) is part of a needle module (18) and has a first tip (17.1) adapted to extend through the distal surface (11.1) and a second tip (17.2) adapted to pierce a septum (25) on a primary package (24) received within the housing (11).

Embodiment 9. The drug delivery device (10) of embodiment 8, wherein the needle (17) is a single needle bent at approximately 90 degrees or wherein the first tip (17.1) and the second tip (17.2) are separate from each other and arranged at approximately 90 degrees to each other and connected within a solid block (19) or via a flexible tube (28).

Embodiment 10. The drug delivery device (10) according to any one of embodiments 2 to 9, comprising a trigger adapted to cause the needle (17) to be moved from the retracted position to the extended position upon operation of the trigger.

Embodiment 11. The drug delivery device (10) according to embodiment 10, wherein the trigger comprises at least one of a shroud (13), at least one button (22) and a body contact sensor (27).

Embodiment 12. The drug delivery device (10) according to embodiment 11, wherein the at least one button (22) is disposed at the proximal surface (11.2) or at at least one lateral surface of the housing (11).

Embodiment 13. The drug delivery device (10) according to embodiment 11 or 12, wherein body contact sensor (27) or the shroud (13) is disposed at the distal surface (11.1), wherein the shroud (13) is adapted to cover the needle (17) when the needle (17) is in the extended position.

Embodiment 14. The drug delivery device (10) according to any one of the embodiments 9 to 13, wherein the needle (17) is adapted to be retracted from the extended position into the retracted position upon removal of the distal surface (11.1) from an injection site.

Embodiment 15. The drug delivery device (10) according to any one of embodiments 8 to 14, comprising a carrier (70) adapted to mount a primary package (24) and movable substantially in parallel with the distal surface (11.1) between a rearward position, in which the second tip (17.2) is spaced from the septum (25) and a forward position, in which the second tip (17.2) pierces the septum (25).

Embodiment 16. The drug delivery device (10) according to embodiment 15, wherein the trigger is configured to initiate movement of the carrier (70) from the rearward position to the forward position.

Embodiment 17. The drug delivery device (10) according to any one of embodiments 11 to 16, wherein the button (22) is adapted to be locked prior to operation of the shroud (13) or body contact sensor (27) preventing operation of the button (22), wherein the button (22) is adapted to be unlocked upon operation of the shroud (13) or body contact sensor (27) allowing operation of the button (22).

Embodiment 18. The drug delivery device (10) according to any one of the preceding embodiments, comprising a drive spring (30) adapted to apply a force in a forward direction to a piston (23) of the primary package (24).

Embodiment 19. The drug delivery device (10) of embodiment 19, comprising a plunger (40) adapted to propagate the force from the drive spring (30) to the piston (23).

Embodiment 20. The drug delivery device (10) according to any one of the preceding embodiments, comprising a primary package (24) containing a medicament.

Embodiment 21. The drug delivery device (10) according to any one of embodiments 15 to 20, wherein the carrier (70) is guided within a trigger chassis (26) which is slidable in a forward direction from a locking position to a release position.

Embodiment 22. The drug delivery device (10) according to any one of embodiments 11 to 21, wherein the body contact sensor (27) is pivoted about an axis (A) in the housing (11) such that a contact part (27.1) of the body contact sensor (27) may extend from the distal surface (11.1) and pivot about the axis (A) to be depressed into the housing (11) behind or flush with the distal surface (11.1).

Embodiment 23. The drug delivery device (10) according to any one of embodiments 8 to 22, wherein the needle module (18) comprises a first sub-module (18.1) holding the first tip (17.1) and a second sub-module (18.2) holding the second tip (17.2), wherein the second sub-module (18.2) is fixed in position within the housing (11) whereas the first sub-module (18.1) is movable from the retracted position in the distal direction into the extended position.

Embodiment 24. The drug delivery device (10) according to any one of embodiments 8 to 23, wherein a needle return spring (29) is arranged to bias the first tip (17.1) towards the retracted position.

Embodiment 25. The drug delivery device (10) according to embodiment 23 or 24, wherein the first sub-module (18.1) comprises at least one pin-shaped protrusion (18.3) adapted to be engaged by a resilient arm (27.2) of the body contact sensor (27) such that, when the contact part (27.1) of the body contact sensor (27) is depressed in the proximal direction (P), the arm (27.2) is resiliently deformed to bias the first sub-module (18.1) in the distal direction (D).

Embodiment 26. The drug delivery device (10) according to any one of embodiments 23 to 25, wherein a hook (26.2) on the trigger chassis (26) is adapted to engage a rib (18.4) on the first sub-module (18.1) preventing movement of the first sub-module (18.1) out of the retracted position when the trigger chassis (26) is in the locking position.

Embodiment 27. The drug delivery device (10) according to any one of embodiments 20 to 26, wherein a button (22) is coupled to the trigger chassis (26) in such a manner that depression of the button (22) in the distal direction (D) moves the trigger chassis (26) from the locking position to the release position.

Embodiment 28. The drug delivery device (10) according to embodiment 27, wherein the button (22) comprises at least one angled cam surface (22.1) engaging a respective button pin (26.3) on the trigger chassis (26).

Embodiment 29. The drug delivery device (10) according to any one of embodiments 20 to 28, wherein the trigger chassis (26) comprises an interlock pin (26.4) engaging a U-shaped slot (27.3) in the body contact sensor (27) in such a manner that movement of the trigger chassis (26) from the locking position to the release position is only possible upon prior depression of the contact part (27.1) in the proximal direction (P).

Embodiment 30. The drug delivery device (10) according to any one of embodiments 20 to 29, wherein a spring element (26.5) is provided to bias the trigger chassis (26) rearward toward the locking position.

Embodiment 31. The drug delivery device (10) according to any one of embodiments 20 to 30, wherein the retracted position of the first sub-module (18.1) is defined by the first sub-module (18.1) abutting a proximal stop (26.6) on the trigger chassis (26) when the trigger chassis (26) is in the locking position.

Embodiment 32. The drug delivery device (10) of embodiment 31, wherein the proximal stop (26.6) is removed when the trigger chassis (26) is in the release position thus allowing the first sub-module (18.1) to move into a second retracted position proximal from the retracted position.

Embodiment 33. The drug delivery device (10) of embodiment 32, wherein in the second retracted position, the protrusion (18.3) on the first sub-module (18.1) disengages the arm (27.2).

Embodiment 34. The drug delivery device (10) according to any one of the preceding embodiments, wherein the housing (11) comprises a distal region (20) and a proximal region (21), the distal region (20) having the distal surface (11.1).

Embodiment 35. The drug delivery device (10) of embodiment 34, wherein mutually complementary snap-lock connectors (20.1) are provided on the distal region (20) and the proximal region (21).

Embodiment 36. The drug delivery device (10) according to any one of embodiments 10 to 35, wherein a shroud spring (50) is arranged to bias the shroud (13) in the distal direction (D) against the housing (11) or against the needle module (18).

Embodiment 37. The drug delivery device (10) according to any one of embodiments 8 to 36, wherein a needle spring (60) is arranged to bias the needle module (18) in the distal direction (D) against the housing (11).

Embodiment 38. The drug delivery device (10) according to any one of embodiments 10 to 37, wherein the needle module (18) comprises one or more guide protrusions (18.3) adapted to be received in slots (13.1) of the shroud (13).

Embodiment 39. The drug delivery device (10) according to any one of embodiments 14 to 38, wherein the carrier (70) comprises at least one forward arm (70.1).

Embodiment 40. The drug delivery device (10) of embodiment 39, wherein a respective retention shelf (70.6) is provided on each forward arm (70.1) adapted to engage one of the guide protrusions (18.3) to prevent movement of the needle module (18) in the distal direction (D) when the carrier (70) is in the rearward position and adapted to disengage the guide protrusion (18.3) when the carrier (70) is moved to the forward position.

Embodiment 41. The drug delivery device (10) of embodiment 38 or 39, wherein each forward arm (70.1) comprises an essentially L-shaped guide channel (70.7) adapted to guide the movement of the guide protrusion (18.3) after having been released from the retention shelf (70.6) upon forward movement of the carrier (70).

Embodiment 42. The drug delivery device (10) of embodiment 41, wherein the guide channel (70.7) has a longitudinal section (70.8) essentially in parallel with the distal surface (11.1) to prevent the needle module (18) from returning in the proximal direction (P) after having been advanced in the distal direction (D).

Embodiment 43. The drug delivery device (10) of embodiment 41 or 42, wherein the guide channel (70.7) comprises a proximal section (70.9) essentially pointing in the proximal direction (P).

Embodiment 44. The drug delivery device (10) of embodiment 43, wherein the proximal section (70.9) deviates from the proximal direction (P) in the forward direction.

Embodiment 45. The drug delivery device (10) according to any one of embodiments 17 to 44, wherein the drive spring (30) is arranged within the plunger (40).

Embodiment 46. The drug delivery device (10) according to any one of embodiments 14 to 45, wherein a carrier spring (80) is arranged to bias the carrier (70) towards the needle module (18).

Embodiment 47. The drug delivery device (10) according to any one of the preceding embodiments, wherein a noise component (90) is arranged to provide an audible feedback when the drug has been at least nearly fully expelled from the primary package (24).

Embodiment 48. The drug delivery device (10) of embodiment 47, wherein the noise component (90) comprises a rod adapted to be received within the drive spring (30).

Embodiment 49. The drug delivery device (10) according to any one of embodiments 14 to 48, wherein one or more retention arms (70.5) are provided on the carrier (70) biased outwards toward the housing (11) and adapted to engage a locking shoulder (20.2) on the housing (11) to prevent forward movement of the carrier (70).

Embodiment 50. The drug delivery device (10) according to any one of embodiments 14 to 49, wherein the carrier (70) comprises a pair of clamps (70.2) adapted to engage a neck (24.3) of the primary package (24) near its forward end (24.1).

Embodiment 51. The drug delivery device (10) of embodiment 49 or 50, wherein the proximal region (21) of the housing (11) comprises at least one rib (21.2) adapted to release the one or more retention arms (70.5) from the locking shoulder (20.2) displacing the retention arm (70.5) inwards out of engagement with the locking shoulder (20.2) when the distal region (20) and the proximal region (21) are assembled to each other.

Embodiment 52. The drug delivery device (10) according to any one of embodiments 14 to 51, wherein the shroud (13) comprises a hook (13.2) adapted to engage the carrier (70) to prevent forward movement of the carrier (70) prior to depression of the shroud (13) and adapted to disengage the carrier (70) upon depression of the shroud (13) allowing movement of the carrier (70).

Embodiment 53. The drug delivery device (10) according to any one of embodiments 17 to 52, wherein the plunger (40) comprises an outer sleeve (40.3) and an inner sleeve (40.4), wherein the drive spring (30) is disposed within the outer sleeve (40.3) but outside the inner sleeve (40.4) and bears against an internal plunger face (40.1) in the forward direction.

Embodiment 54. The drug delivery device (10) of embodiment 53, wherein the noise component (90) is received within the inner sleeve (40.4) and comprises a flange (90.1) against which the drive spring (30) bears in the rearward direction.

Embodiment 55. The drug delivery device (10) according to any one of embodiments 18 to 54, wherein one or more resilient carrier clips (70.3) are provided on the carrier (70) adapted to engage respective apertures (40.2) in the plunger (40) preventing the plunger (40) from advancing forward.

Embodiment 56. The drug delivery device (10) of embodiment 55, wherein the housing (11) comprises casework (20.3) positioned to outwardly support the one or more resilient carrier clips (70.3) preventing them from disengaging the apertures (40.2) when the carrier (70) is in the rearward position, wherein upon movement of the carrier (70) towards the forward position, the carrier clips (70.3) are no longer supported be the casework (20.3).

Embodiment 57. The drug delivery device (10) of embodiment 55 or 56, wherein the carrier clips (70.3) are angled such that the load from the drive spring (30) creates a slight lateral force on the carrier clips (70.3) biasing them outward to disengage the aperture (40.2).

Embodiment 58. The drug delivery device (10) according to any one of embodiments 54 to 57, wherein the carrier clips (70.3) are adapted to engage the flange (90.1) through the apertures (40.2) preventing the flange (90.1) from moving rearward.

Embodiment 59. The drug delivery device (10) according to any one of embodiments 54 to 58, wherein the noise component (90) comprises a hollow noise rod (90.2) adapted to be arranged within the inner sleeve (40.4).

Embodiment 60. The drug delivery device (10) of embodiment 59, wherein a carrier rod (70.4) is provided on the rear end of the carrier (70) directed in the forward direction into the hollow noise rod (90.2).

Embodiment 61. The drug delivery device (10) of embodiment 60, wherein the noise rod (90.2) is split along its length forming two or more resilient arms (90.3) biased outwards and prevented from moving outwards when within the inner sleeve (40.4), wherein forward ends (90.4) of the arms (90.3) comprise an inwardly directed protrusion engaging the carrier rod (70.4) such that the noise rod (90.2) cannot move in the rearward direction relative to the carrier (70) prior to outward deflection of the arms (90.3), wherein when the plunger (40) has been at least nearly fully advanced forward to expel the drug, the inner sleeve (40.4) is removed from the arms (90.3) so they deflect outward and their forward ends (90.4) disengage the carrier rod (70.4) so that the noise component (90) is released to be moved in the rearward direction driven by the residual force of the drive spring (30) and impact a rear end of the carrier (70) thus creating a click noise indicating the end of dose.

Embodiment 62. The drug delivery device (10) according to any one of embodiments 37 to 61, wherein the shroud spring (50) acts between the shroud (13) and the needle module (18) so that movement of the needle module (18) in the distal direction (D) compresses the shroud spring (50).

Embodiment 63. The drug delivery device (10) according to any one of embodiments 55 to 62, wherein one or more ramps (20.4, 70.10) are provided on the housing 11 and/or on the carrier (70) configured to deflect the carrier clips (70.3) when the carrier (70) is being moved forward from the rearward position.

Embodiment 64. The drug delivery device (10) according to any one of embodiments 36 to 63, wherein the shroud (13) is moved in the distal direction (D) driven by the shroud spring (50) upon removal of the drug delivery device (10) from the injection site, wherein in this state, the shroud (13) extends further from the distal surface (11.1) than prior to use to cover the still extended needle (17).

Embodiment 65. The drug delivery device (10) according to any one of embodiments 12 to 64, wherein one or more clips (21.3, 13.12) are provided on the housing (11) and/or on the shroud (13) to engage the shroud (13) to the housing (11) when the shroud (13) is extended to cover the needle (17).

Embodiment 66. The drug delivery device (10) according to any one of embodiments 8 to 65, wherein the needle module (18) comprises at least one protrusion (18.3) adapted to engage a ramped surface (21.4) on the housing (11).

Embodiment 67. The drug delivery device (10) of embodiment 66, wherein the ramped surface (21.4) is part of a tube (21.5) extending within the housing (11) in the distal direction (D), the tube (21.5) adapted to retain the needle module (18) which may have a corresponding cylindrical shape such that it can rotate within the tube (21.5), wherein when the needle module (18) is in the retracted position, the bias of the needle spring (60) and the protrusion (18.3) engaging the ramped surface (21.4) subject the needle module (18) to a torque in a first rotational direction (R1) to disengage the protrusion (18.3) from the ramped surface (21.4).

Embodiment 68. The drug delivery device (10) of embodiment 67, wherein the shroud (13) comprises an inner sleeve (13.3) having a cylindrical shape telescoped with the tube (21.5), the inner sleeve (13.3) comprising a slot (13.4) adapted to prevent the needle module (18) to rotate in the first rotational direction (R1) when the shroud (13) is in the extended position and to allow the needle module (18) to rotate in the first rotational direction (R1) when the shroud (13) in the retracted position.

Embodiment 69. The drug delivery device (10) of embodiment 68, wherein the slot (13.4) has a proximal section (13.5) extending in the proximal direction (P) and aligned with the ramped surface (21.4), a circumferential section (13.6) distally adjacent the proximal section (13.5)

and extending in the first rotational direction (R1), and a distal section (13.7) distally adjacent the circumferential section (13.6) extending in the distal direction (D) and not aligned with the proximal section (13.5).

Embodiment 70. The drug delivery device (10) of embodiment 69, wherein the circumferential section (13.6) comprises a ramped surface aligning with the ramped surface (21.4) on the housing (11).

Embodiment 71. The drug delivery device (10) according to any one of embodiments 39 to 71, wherein the at least one forward arm (70.1) is adapted to engage the shroud (13) and adapted to be deflected outwards away from the shroud (13).

Embodiment 72. The drug delivery device (10) according to any one of embodiments 46 to 71, wherein the carrier spring (80) is arranged laterally from the carrier (70) or about the carrier (70).

Embodiment 73. The drug delivery device (10) of embodiment 71 or 72, wherein the forward arms (70.1) of the carrier (70) comprise a front surface (70.11) adapted to abut a stop (20.5) on the housing (11) such that the carrier (70) is prevented from moving forward when in the rearward position.

Embodiment 74. The drug delivery device (10) according to any one of embodiments 71 to 73, wherein at least one proximal protrusion (70.12) is provided on the forward arms (70.1) adapted to abut a respective transversal beam (13.8) on the shroud (13) when the carrier (70) is in the rearward position thus limiting extension of the shroud (13) from the distal surface (11.1). Embodiment 75. The drug delivery device (10) according to embodiment 74, wherein a lateral stop (13.9) is provided on the transversal beam (13.8) adapted to laterally abut the proximal protrusion (70.12) preventing outward deflection of the forward arm (70.1) so the front surface (70.11) cannot disengage the stop (20.5).

Embodiment 76. The drug delivery device (10) according to any one of embodiments 73 to 75, wherein the protrusion (18.3) of the needle module (18) comprise a ramp (18.5) adapted to engage the forward arm (70.1) to deflect it outward upon movement of the needle module (18) in the distal direction (D) to disengage the front surface (70.11) from the stop (20.5).

Embodiment 77. The drug delivery device (10) according to any one of embodiments 10 to 76, wherein a flexible clip (13.10) on the shroud (13) is adapted to abut the needle module (18) to prevent it from moving in the distal direction (D) when in the retracted position, wherein the abutment is removable by outwardly deflecting the flexible clip (13.10) to release the needle module (18).

Embodiment 78. The drug delivery device (10) according to embodiment 77, wherein a button (22) is provided for deflecting the flexible clip (13.10).

Embodiment 79. The drug delivery device (10) of embodiment 78, wherein the button (22) is arranged on the housing (11) such that it only couples with the flexible clip (13.10) when the shroud (13) is in the retracted position such that operation of the button (22) prior to depression of the shroud (13) does not release the needle module (18).

Embodiment 80. The drug delivery device (10) of embodiment 79, wherein a chamfer (13.11) on the flexible clip (13.10) is adapted to allow release of the needle module (18) regardless of a sequence of operation of the shroud (13) and button (22).

Embodiment 81. The drug delivery device (10) according to any one of embodiments 10 to 80, wherein one or two buttons (22) are provided laterally on the housing (11) to release the needle module (18) upon operation.

Embodiment 82. The drug delivery device (10) according to any one of embodiments 10 to 81, wherein a spring element (22.3) is provided to bias the button (22) to extend from the housing (11).

Embodiment 83. The drug delivery device (10) according to any one of embodiments 8 to 82, wherein a needle retainer clip (21.6) is arranged on and within the housing (11) to releasably engage the needle module (18) in the retracted position.

Embodiment 84. The drug delivery device (10) of embodiment 83, wherein the needle retainer clip (21.6) and/or the needle module (18) have/has one or more ramps adapted to outwardly deflect the needle retainer clip (21.6) under a force from the needle spring (60) to disengage the needle module (18) from the needle retainer clip (21.6) to allow the needle module (18) to move in the distal direction (D).

Embodiment 85. The drug delivery device (10) of embodiment 83 or 84, wherein each of the one or two buttons (22) comprises a transversal beam (22.2), one or both of them adapted to outwardly support the needle retainer clip (21.6) when the one or two buttons (22) are not depressed such that the needle retainer clip (21.6) cannot be outwardly deflected, wherein depression of the one or two buttons (22) removes the outward support from the needle retainer clip (21.6) such that the needle module (18) is released.

Embodiment 86. The drug delivery device (10) according to any one of embodiments 38 to 85, wherein at least one resilient catch arm (13.13) is arranged on the shroud (13) to releasably block access of the slot (13.1) so that the guide protrusion (18.3) cannot enter the slot (13.1) and the needle module (18) is prevented from advancing in the distal direction (D), wherein the catch arm (13.13) is adapted to be deflected to allow the protrusion (18.3) to access the slot (13.1).

Embodiment 87. The drug delivery device (10) of embodiment 86, wherein a button (22) is arranged on the housing (11) to engage the catch arm (13.13) when the shroud (13) is moved into the retracted position, wherein, if the button (22) is depressed when the shroud (13) is in the retracted position, the catch arm (13.13) is deflected and unblocks access of the protrusion (18.13) into the slot (13.1).

Embodiment 88. The drug delivery device (10) of embodiment 86 or 87, wherein upon removal of the drug delivery device (10) from the injection site when the needle module (17) is in the extended position, the shroud (13) returns in the distal direction (D) driven by the shroud spring (50) while the needle module (18) remains in position due to distally abutting on the housing (11).

Embodiment 89. The drug delivery device (10) of embodiment 88, wherein due to the shroud's (13) return in the distal direction (D) the catch arm (13.13) disengages the button (22) so that the catch arm (13.13) relaxes and blocks access of the protrusion (18.3) to the slot (13.1).

Embodiment 90. The drug delivery device (10) according to any one of embodiments 37 to 89, wherein the needle spring (60) is charged by depression of the shroud (13) into the retracted position.

Embodiment 91. The drug delivery device (10) according to any one of embodiments 8 to 90, wherein the needle module (18) comprises one or more ramps (18.5) adapted to engage respective resilient clips (11.3) on the housing (11) which are outwardly supported by the shroud (13) when the shroud (13) is in an extended position so that the resilient clips (11.3) cannot deflect preventing the needle module (18) from moving from the retracted position in the distal direction (D), wherein depression of the shroud (13) in the proximal direction (P) removes the outward support of the one or more ramps (18.5) allowing release of the needle module (18).

Embodiment 92. The drug delivery device (10) according to any one of embodiments 10 to 91, wherein one or two laterally arranged buttons (22) are interlocked with the shroud (13) preventing the shroud (13) from moving in the proximal direction (P) from the extended position prior to depression of the buttons (22) and allowing movement of the shroud (13) upon depression of the buttons (22).

Embodiment 93. The drug delivery device (10) according to any one of embodiments 14 to 92, wherein the carrier (70) is slidable with in the housing (11) essentially in parallel with the distal surface (11.1) and pivotable at a rear end of the carrier (70) within the housing (11).

Embodiment 94. The drug delivery device (10) of embodiment 93, wherein an axle (70.13) of the carrier (70) engages in one or more slot holes (11.4) in the housing (11).

Embodiment 95. The drug delivery device (10) according to any one of embodiments 10 to 94, wherein the body contact sensor (27) is configured as a shroud (13) for covering an extended needle (17).

Embodiment 96. The drug delivery device (10) according to any one of embodiments 14 to 95, wherein the carrier (70) comprises a guide channel (70.7) and the body contact sensor (27) comprises a cam follower (27.4) adapted to be received and guided within the guide channel (70.1) to control movement of the carrier (70) depending on movement of the body contact sensor (27).

Embodiment 97. The drug delivery device (10) according to embodiment 96, wherein the guide channel (70.7) comprises a an inclined section (70.14) generally pointing in the rearward direction and the proximal direction (P) at an angle relative to the distal surface (11.1), the inclined section (70.14) adapted to engage the cam follower (27.4) when the contact part (27.1) of the body contact sensor (27) extends from the distal surface (11.1).

Embodiment 98. The drug delivery device (10) according to embodiment 97, wherein the cam follower (27.4) is adapted to move up the inclined section (70.14) upon depression of the contact part (27.1) thereby moving the carrier (70) forward, until the cam follower (27.4) reaches a proximal section (70.15) of the guide channel (70.7) directed essentially in the proximal direction (P).

Embodiment 99. The drug delivery device (10) according to any one of embodiments 39 to 98, wherein a resilient clip (11.3) is disposed on the housing (11) so as to abut the needle module (18) when the needle module (18) is in the retracted position preventing movement of the needle module (18) in the distal direction (D), wherein the one or two resilient forward arms (70.1) are adapted to engage the resilient clip (11.3) to deflect it away from the needle module (18) to release the needle module (18) allowing it to move in the distal direction (D) upon forward movement of the carrier (70).

Embodiment 100. The drug delivery device (10) according to any one of embodiments 18 to 99, wherein a locking pin (11.5) is arranged in the housing (11) adapted to releasably engage in an aperture (40.2) in the plunger (40) preventing the plunger (40) from advancing forward.

Embodiment 101. The drug delivery device (10) according to any one of embodiments 98 to 100, wherein upon movement of the needle module (18) in the distal direction (D) the primary package (24) and the carrier (70) are tilted about the axle (70.13) while the cam follower (27.4) moves up the proximal section (70.15).

Embodiment 102. The drug delivery device (10) according to embodiment 101, wherein the plunger is also tilted upon movement of the needle module (18) in the distal direction (D) thus disengaging the locking pin (11.5) from the aperture (40.2) to release the plunger (40).

Embodiment 103. The drug delivery device (10) according to any one of the embodiments 21 to 102, wherein the primary package (24) is held within the carrier (70) by two or more resilient clamps (70.2) on the carrier (70) engaging a neck (24.3) of the primary package (24) near its forward end (24.1), wherein the clamps (70.2) may be located within and outwardly supported by the collar (26.1) in the locking position of the trigger chassis (26) such that the clamps (70.2) are prevented from being deflected away from the primary package (24) so the primary package (24) cannot move forward relative to the carrier (70), wherein the collar (26.1) is moved forward relative to the carrier (70) when the trigger chassis (26) is moved into its release position such that the collar (26.1) does no longer outwardly support the resilient clamps (70.2) so that the primary package (24) may be moved forward relative to the carrier (70) deflecting the resilient clamps (70.2).

Embodiment 104. The drug delivery device (10) according to any one of the embodiments 84 to 103, wherein the shroud (13) comprises a slot (13.1) having a longitudinal portion (13.1.1) and a transversal portion (13.1.2) being wider than the longitudinal portion (13.1.1), wherein the needle retainer clip (21.6) comprises at least one stepped surface (21.6.1) running along an inner diameter face of the shroud (13) matching the transversal portion (13.1.2) when the shroud (13) is at least almost fully depressed, wherein prior to almost full depression of the shroud (13), the stepped surface (21.6.1) is not aligned with the transversal portion (13.1.2) but located within the longitudinal portion (13.1.1) such that the stepped surface (21.6.1) abuts the inner diameter face of the shroud (13) preventing the retainer clip (21.6) from being deflected outwards thus also preventing release of the needle module (18).

Embodiment 105. A method of using the drug delivery device (10) according to any one of the preceding embodiments, comprising taking the housing (11) with a hand such that the proximal surface (11.2) is located within a palm of the hand, placing the distal surface (11.1) on an injection site, operating the trigger to move the needle (17) to the extended position, holding the drug delivery device (10) on the injection site during an injection time.

In an exemplary embodiment, the second tip 17.2 may have a greater diameter than the first tip 17.1.

In an exemplary embodiment, a soft layer may be arranged on distal surface of the shroud 13 or skin contact button 27 which contacts the skin.

LIST OF REFERENCES

10 drug delivery device
10.1 drive subassembly
10.2 control subassembly
11 housing
11.1 distal surface
11.2 proximal surface
11.3 resilient clip
11.4 slot hole
11.5 locking pin
**11*a*** window
12 cap assembly
13 shroud
13.1 slot

13.1.1 longitudinal portion
13.1.2 transversal portion
13.2 hook
13.3 inner sleeve
13.4 slot
13.5 proximal section
13.6 circumferential section
13.7 distal section
13.8 transversal beam
13.9 lateral stop
13.10 flexible clip
13.11 chamfer
13.12 shroud lock clip
13.13 catch arm
17 needle
17.1 first tip
17.2 second tip
18 needle module
18.1 first sub-module
18.2 second sub-module
18.3 protrusion
18.4 rib
18.5 ramp
19 solid block
20 distal region
20.1 snap-lock connector
20.2 locking shoulder
20.3 casework
20.4 ramp
20.5 stop
21 proximal region
21.2 rib
21.3 clip
21.4 ramped surface
21.5 tube
21.6 needle retainer clip
21.6.1 stepped surface
22 button
22.1 cam surface
22.2 transversal beam
22.3 spring element
23 piston
24 primary package
24.1 forward end
24.2 rear end
24.3 neck
25 septum
26 trigger chassis
26.1 collar
26.2 hook
26.3 button pin
26.4 interlock pin
26.5 spring element
26.6 proximal stop
27 body contact sensor
27.1 contact part
27.2 arm
27.3 U-shaped slot
27.4 cam follower
28 flexible tube
29 needle return spring
30 drive spring
40 plunger
40.1 internal plunger face
40.2 aperture
40.3 outer sleeve
40.4 inner sleeve
50 shroud spring
60 needle spring
70 carrier
70.1 forward arm
70.2 clamp
70.3 carrier clip
70.4 carrier rod
70.5 retention arm
70.6 retention shelf
70.7 guide channel
70.8 longitudinal section
70.9 proximal section
70.10 ramp
70.11 front surface
70.12 proximal protrusion
70.13 axle
70.14 inclined section
70.15 proximal section
80 carrier spring
90 noise component
90.1 flange
90.2 noise rod
90.3 arm
90.4 forward end
100 collar interface
A axis
D distal direction
P proximal direction
R1 first rotational direction
X longitudinal axis

The invention claimed is:

1. A drug delivery device, comprising:
a primary package and a piston comprised within the primary package, wherein the primary package comprises a dispensing end;
a housing adapted to receive the primary package,
the housing comprising a distal surface adapted to be placed against an injection site and a proximal surface opposite the distal surface, the proximal surface being adapted to be held in a palm of a user's hand during drug delivery,
the housing having a flat form-factor in such a manner that a first dimension of the housing between the distal surface and the proximal surface is less than at least one dimension perpendicular to the first dimension, wherein each dimension is a distance between two respective opposite surfaces of the housing;
a carrier adapted to carry and at least partially surround the primary package, wherein the carrier and the primary package are adapted to be moveable in parallel with the distal surface and with respect to the housing; and
an energy source bearing against the carrier and arranged to bias the carrier towards a needle module,
wherein the carrier comprises a carrier surface facing away from the dispensing end, the carrier surface being configured to engage a package surface of the primary package, the package surface facing the dispensing end.

2. The drug delivery wherein the needle module is configured to be connected or connectable to the primary package received within the housing, wherein the needle module comprises a first tip automatically movable between a retracted position hidden within the housing and an extended position extending through the distal surface.

3. The drug delivery device according to claim 2, wherein the needle module has a second tip adapted to pierce a septum on the primary package received within the housing.

4. The drug delivery device of claim 3, wherein the needle module comprises a single needle bent at approximately 90 degrees or wherein the first tip and the second tip are separate from each other and arranged at approximately 90 degrees to each other and connected within a solid block or via a flexible tube.

5. The drug delivery device according to claim 3, wherein the carrier is movable in parallel with the distal surface between a rearward position, in which the second tip is spaced from the septum and a forward position, in which the second tip pierces the septum.

6. The drug delivery device according to claim 5, wherein the energy source is a carrier spring.

7. The drug delivery device according to claim 2, comprising a trigger adapted to cause the needle module to be moved from the retracted position to the extended position upon operation of the trigger, wherein the trigger comprises at least one of a shroud, at least one button, and a body contact sensor.

8. The drug delivery device according to claim 7, wherein the trigger comprises the at least one button, and the at least one button is disposed at the proximal surface or at least one lateral surface of the housing.

9. The drug delivery device according to claim 7, wherein the button is adapted to be locked prior to an operation of the shroud or an operation of the body contact sensor to prevent an operation of the button, and wherein the button is adapted to be unlocked upon the operation of the shroud or the operation of the body contact sensor to allow the operation of the button.

10. The drug delivery device according to claim 9, further comprising a shroud spring arranged to bias the shroud in a distal direction against the housing or against the needle module and/or a needle spring arranged to bias the needle module in a distal direction against the housing.

11. The drug delivery device according to claim 10, wherein the needle spring is charged by depression of the shroud into the retracted position.

12. The drug delivery device according to claim 2, further comprising a needle return spring arranged to bias the first tip towards the retracted position.

13. The drug delivery device of claim 1, wherein a mounting axis of the primary package is at a right angle with respect to the first dimension.

14. The drug delivery device of claim 1, wherein the distal surface is non-adhesive.

15. The drug delivery device of claim 1, wherein the distal surface is rigid.

16. The drug delivery device according to claim 1, further comprising a drive spring adapted to apply a force in a forward direction to the piston of the primary package.

17. The drug delivery device according to claim 1, wherein the primary package contains a medicament.

18. A method of injecting a medicament, the method comprising:

connecting a needle module of a drug delivery device to a dispensing end of a primary package, wherein the primary package contains the medicament and is mounted on a carrier within a housing of the drug delivery device such that a carrier surface that faces away from the dispensing end engages a package surface of the primary package that faces the dispensing end, wherein the needle module includes a first tip and a second tip, and wherein an energy source bears against the carrier and is arranged to bias the carrier towards the needle module, and wherein a piston is comprised within the primary package;

placing a distal surface of the housing against an injection site while holding a proximal surface, opposite the distal surface, of the housing in a palm of a user's hand; and injecting the medicament through the first tip by causing the carrier, which is carrying and at least partially surrounding the primary package, to move relative to the distal surface between a rearward position, in which the second tip is spaced from a septum on the primary package and a forward position, in which the second tip pierces the septum, wherein the carrier and the primary package move in parallel with the distal surface and with respect to the housing, and wherein the housing has a flat form-factor in such a manner that a first dimension of the housing between the distal surface and the proximal surface is less than at least one dimension perpendicular to the first dimension, wherein each dimension is a distance between two respective opposite surfaces of the housing.

19. The method of claim 18, wherein causing the carrier to move comprises activating a trigger that comprises at least one of a shroud, at least one button, and a body contact sensor.

20. The method of claim 18, further comprising applying a force in a forward direction to the piston of the primary package.

21. A drug delivery device, comprising:

a primary package and a piston comprised within the primary package, the primary package comprising a dispensing end;

a housing adapted to receive the primary package, the housing comprising a distal surface adapted to be placed against an injection site and a proximal surface opposite the distal surface, the proximal surface being adapted to be held in a palm of a user's hand during drug delivery, the housing having a flat form-factor in such a manner that a first dimension of the housing between the distal surface and the proximal surface is less than at least one dimension perpendicular to the first dimension, wherein each dimension is a distance between two respective opposite surfaces of the housing; and a carrier adapted to carry and at least partially surround in a direction along the first dimension a section of the primary package that has a maximal radial extension, wherein the carrier and the primary package are adapted to be moveable in parallel with the distal surface and with respect to the housing, wherein the piston is configured to be moved in a dispensing direction towards the dispensing end into a piston end position, the piston end position being a final position of the piston during operation of the drug delivery device, and wherein the carrier comprises a carrier portion which extends further in the dispensing direction than the piston in its piston end position relative to the housing.

* * * * *